(12) United States Patent
Cottone

(10) Patent No.: US 11,007,345 B2
(45) Date of Patent: May 18, 2021

(54) MODULAR VASCULAR CATHETER

(71) Applicant: OrbusNeich Medical PTE. LTD., Singapore (SG)

(72) Inventor: Robert J. Cottone, Davie, FL (US)

(73) Assignee: OrbusNeich Medical PTE. LTD., Singapore (SG)

( * ) Notice: Subject to any disclaimer, the term of this patent is extended or adjusted under 35 U.S.C. 154(b) by 431 days.

(21) Appl. No.: 15/726,024

(22) Filed: Oct. 5, 2017

(65) Prior Publication Data

US 2018/0093070 A1 Apr. 5, 2018

Related U.S. Application Data

(60) Provisional application No. 62/404,552, filed on Oct. 5, 2016.

(51) Int. Cl.
*A61M 25/00* (2006.01)
*A61M 39/10* (2006.01)
(Continued)

(52) U.S. Cl.
CPC .... *A61M 25/0021* (2013.01); *A61M 25/0041* (2013.01); *A61M 25/0045* (2013.01);
(Continued)

(58) Field of Classification Search
CPC .......... A61M 25/0021; A61M 25/0041; A61M 25/0045; A61M 25/0051; A61M 25/0052;
(Continued)

(56) References Cited

U.S. PATENT DOCUMENTS 3,674,014 A 7/1972 Tillander
5,352,236 A 10/1994 Jung et al.
(Continued)

FOREIGN PATENT DOCUMENTS

EP 0542246 5/1993
EP 0626604 A2 11/1994
(Continued)

OTHER PUBLICATIONS

Haas, Carl; Machine English Translation of EP06266042A2; Original published 1994; Accessed Jan. 5, 2021; (https://worldwide.espacenet.com/patent/search/family/006489209/publication/EP0626604A2?q=0626604).*
(Continued)

*Primary Examiner* — Emily L Schmidt
*Assistant Examiner* — Leah J Swanson
(74) *Attorney, Agent, or Firm* — Leason Ellis LLP

(57) ABSTRACT

A catheter is provided that comprises at least one proximal tubular module and a distal tubular module, each of the tubular modules having at least one section with spiral cuts, each pair of adjacent tubular modules are coupled by a joint, the joint comprising, (a) at least one snap-fit connector on a first tubular module and a snap-fit acceptor positioned on the adjacent tubular module, the snap-fit connector being elastically deformable when engaged, and (b) at least one stabilizing element, including, a tongue element positioned on the first tubular module or the adjacent tubular module, and a groove element positioned on the opposite, first tubular module or the opposite, adjacent tubular module.

25 Claims, 55 Drawing Sheets

(51) Int. Cl.
*A61M 25/01* (2006.01)
*A61M 25/09* (2006.01)

(52) U.S. Cl.
CPC .... *A61M 25/0052* (2013.01); *A61M 25/0054* (2013.01); *A61M 25/0108* (2013.01); *A61M 25/09* (2013.01); *A61M 39/10* (2013.01); *A61M 25/0051* (2013.01); *A61M 25/0102* (2013.01); *A61M 2025/0042* (2013.01); *A61M 2025/0046* (2013.01); *A61M 2025/0059* (2013.01); *A61M 2205/0216* (2013.01); *A61M 2205/0266* (2013.01)

(58) Field of Classification Search
CPC ............ A61M 25/0054; A61M 25/001; A61M 25/0067–0069; A61M 25/008; A61M 25/0082; A61M 2025/0081; A61M 2025/0096; A61M 25/0194; A61M 2025/0197
See application file for complete search history.

(56) References Cited

U.S. PATENT DOCUMENTS

| | | |
|---|---|---|
| 5,507,731 A | 4/1996 | Hernandez et al. |
| 5,656,011 A * | 8/1997 | Uihlein .................. A61B 1/008 600/143 |
| 5,685,878 A | 11/1997 | Falwell et al. |
| 5,695,506 A * | 12/1997 | Pike ............... A61B 17/320783 604/22 |
| 5,749,828 A * | 5/1998 | Solomon ............... A61B 1/0055 600/139 |
| 5,772,668 A * | 6/1998 | Summers ................... A61F 2/88 606/191 |
| 5,876,344 A | 3/1999 | Baker et al. |
| 6,273,876 B1 | 8/2001 | Klima et al. |
| 6,635,047 B2 * | 10/2003 | Forsberg ........... A61M 25/0045 264/211.2 |
| 6,915,169 B2 * | 7/2005 | Flynn ..................... A61N 1/056 439/909 |
| 7,867,219 B2 | 1/2011 | Chambers |
| 7,981,091 B2 | 7/2011 | Root et al. |
| 7,981,148 B2 | 7/2011 | Aguilar et al. |
| 8,419,658 B2 * | 4/2013 | Eskuri ................... A61M 25/09 600/585 |
| 8,500,785 B2 * | 8/2013 | Gunderson ............... A61F 2/95 604/523 |
| 8,974,454 B2 | 3/2015 | de la Rama et al. |
| 2003/0028127 A1 | 2/2003 | Balzum et al. |
| 2005/0075538 A1 | 4/2005 | Banik et al. |
| 2006/0006649 A1 | 1/2006 | Galdonik et al. |
| 2008/0097398 A1 | 4/2008 | Mitelberg et al. |
| 2008/0215008 A1 * | 9/2008 | Nance ............. A61B 17/12022 604/164.03 |
| 2008/0287741 A1 | 11/2008 | Ostrovsky et al. |
| 2009/0157162 A1 * | 6/2009 | Chow ....................... A61F 2/95 623/1.11 |
| 2010/0030217 A1 | 2/2010 | Mitusina et al. |
| 2010/0331776 A1 | 12/2010 | Salahieh et al. |
| 2012/0016367 A1 * | 1/2012 | Chabansky ........ A61B 17/1642 606/79 |
| 2012/0143175 A1 | 6/2012 | Hermann et al. |
| 2014/0025045 A1 * | 1/2014 | Abt ....................... B29C 70/766 606/1 |
| 2014/0058324 A1 | 2/2014 | Salahieh et al. |
| 2014/0235361 A1 | 8/2014 | Forster et al. |
| 2015/0005801 A1 | 1/2015 | Marquis et al. |
| 2015/0025562 A1 | 1/2015 | Dinh et al. |
| 2016/0074627 A1 | 3/2016 | Cottone |
| 2016/0101261 A1 | 4/2016 | Kugler et al. |
| 2016/0101262 A1 | 4/2016 | Root et al. |
| 2016/0121080 A1 | 5/2016 | Cottone |
| 2016/0250443 A1 | 9/2016 | Kornowski et al. |
| 2016/0331928 A1 | 11/2016 | Saphier |
| 2016/0346946 A1 | 12/2016 | Kasen |

FOREIGN PATENT DOCUMENTS

| | | |
|---|---|---|
| EP | 0764423 A1 | 3/1997 |
| EP | 0778040 | 6/1997 |
| EP | 0916359 | 5/1999 |
| EP | 1977781 A1 | 10/2008 |
| EP | 2392430 | 12/2011 |
| WO | 9600099 | 1/1996 |
| WO | 2004105855 | 12/2004 |
| WO | 2006041612 | 4/2006 |
| WO | 2006042043 | 4/2006 |
| WO | 2007149841 | 12/2007 |
| WO | 2009020832 | 2/2009 |
| WO | 2009/100368 A1 | 8/2009 |
| WO | 2011159955 | 12/2011 |
| WO | 2011162853 | 12/2011 |
| WO | 2014014644 | 1/2014 |
| WO | 2014/077881 A1 | 5/2014 |
| WO | 2014066439 | 5/2014 |
| WO | 2016064753 | 4/2016 |

OTHER PUBLICATIONS

Peter Bloss, et al. Investigations of the pushability behavior of cardiovascular angiographic catheters, Bio-Medical Materials and Engineering 13 (2003) 327-343 327 IOS Press; 7 pages.

Burcu Basar, et al., Segmented nitinol guidewires with stiffness-matched connectors for cardiovascular magnetic resonance catheterization: preserved mechanical performance and freedom from heating, Basar et al. Journal of Cardiovascular Magnetic Resonance (2015) 17:105; 9 pages.

International Search Report and Written Opinion corresponding to International Patent Application No. PCT/US17/55351 dated Mar. 7, 2018; 19 pages.

Supplementary European Search Report of EP application EP 17859188, dated Oct. 30, 2020.

* cited by examiner

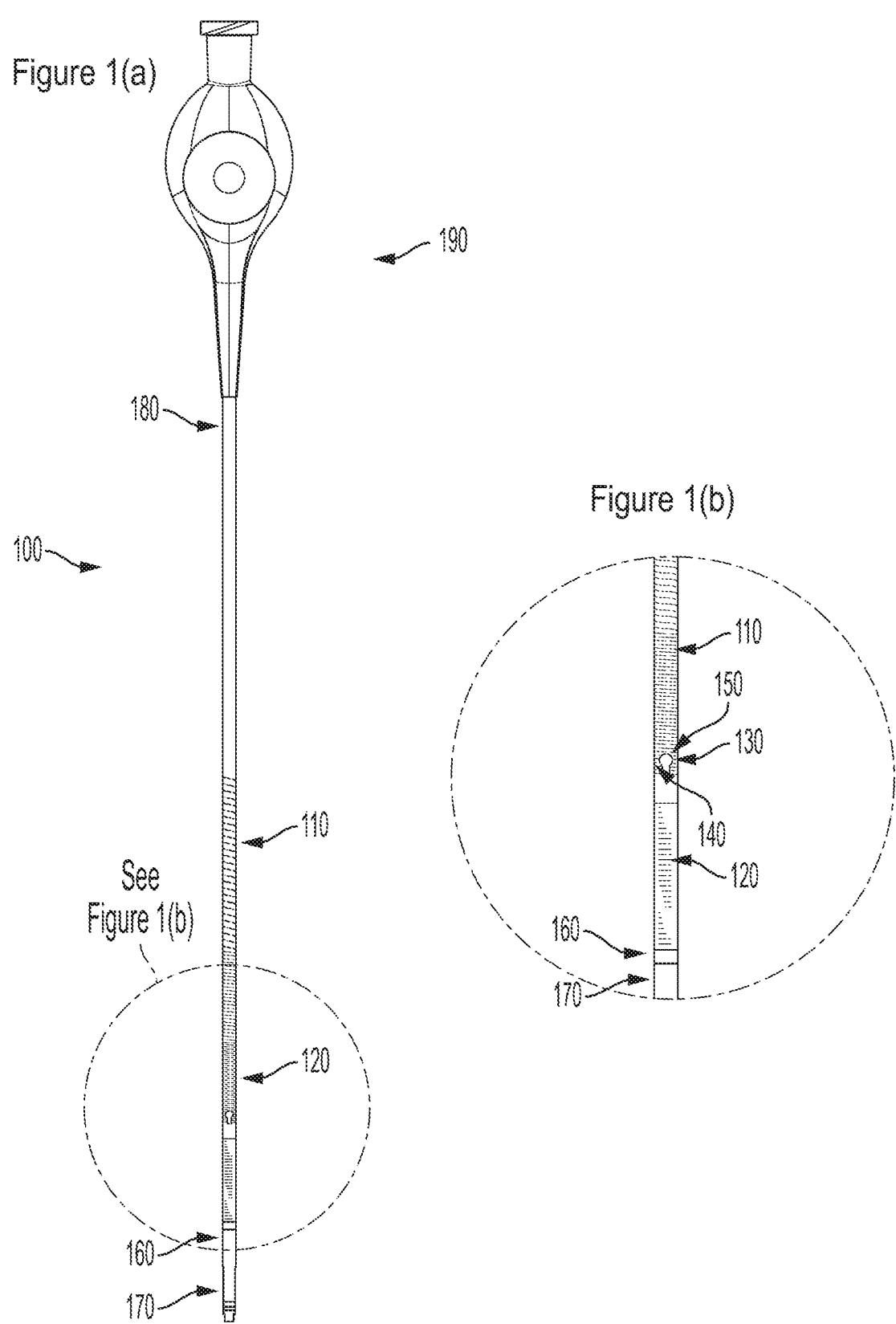

Figure 2(b)  Figure 2(c)  Figure 2(d)  Figure 2(e)
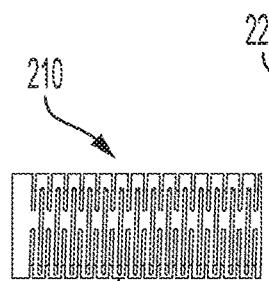 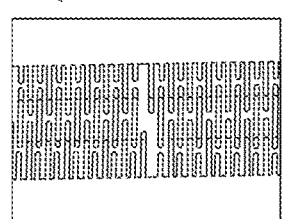 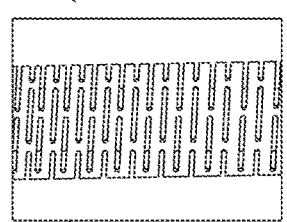 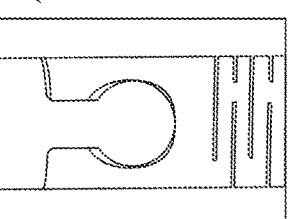
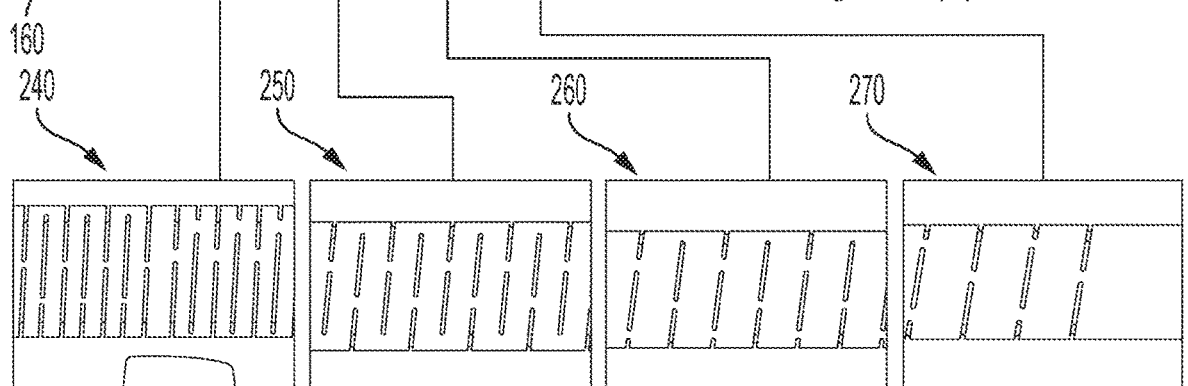
Figure 2(a)
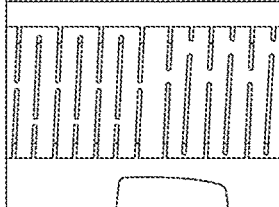 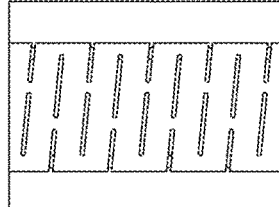 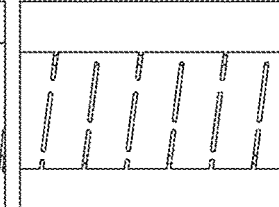 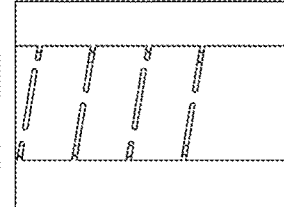
Figure 2(f)  Figure 2(g)  Figure 2(h)  Figure 2(i)

SEE Figure 5(b)

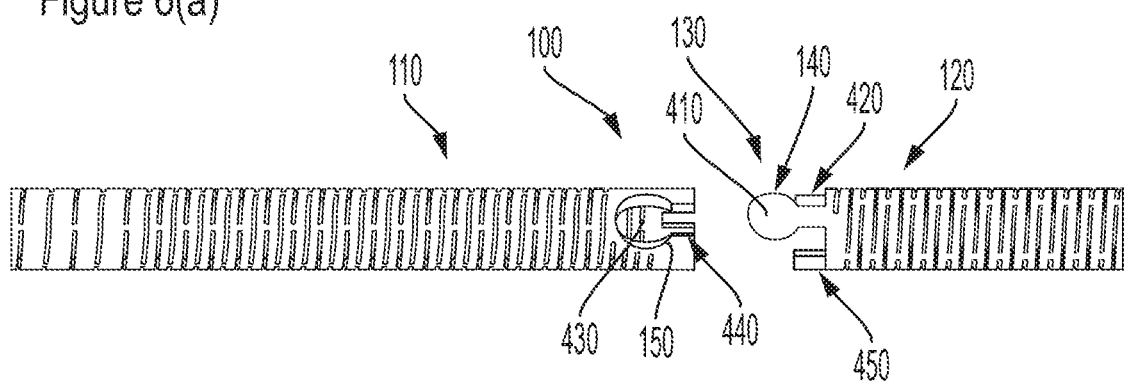
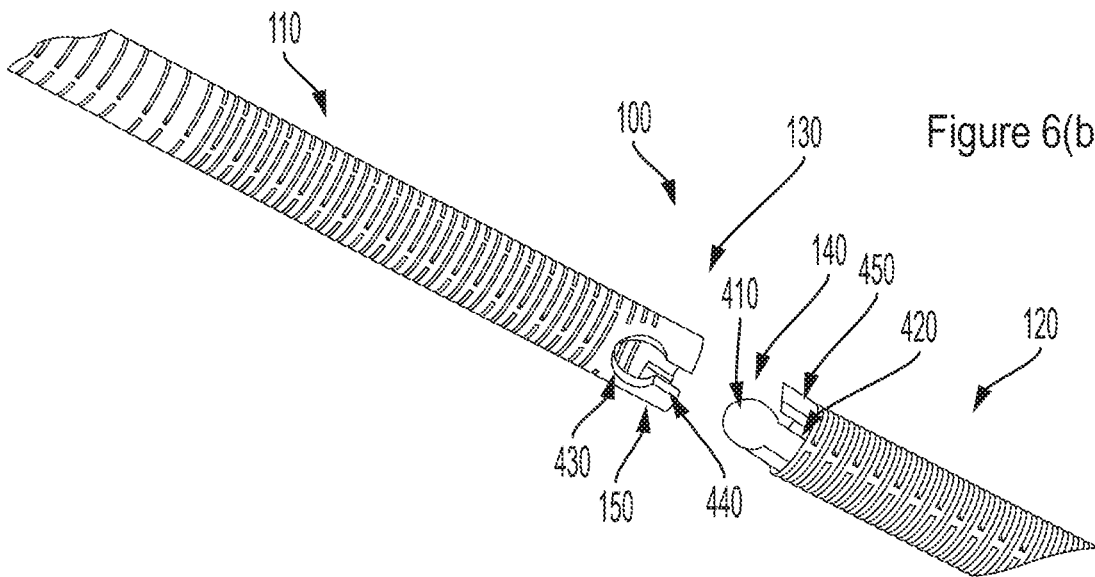

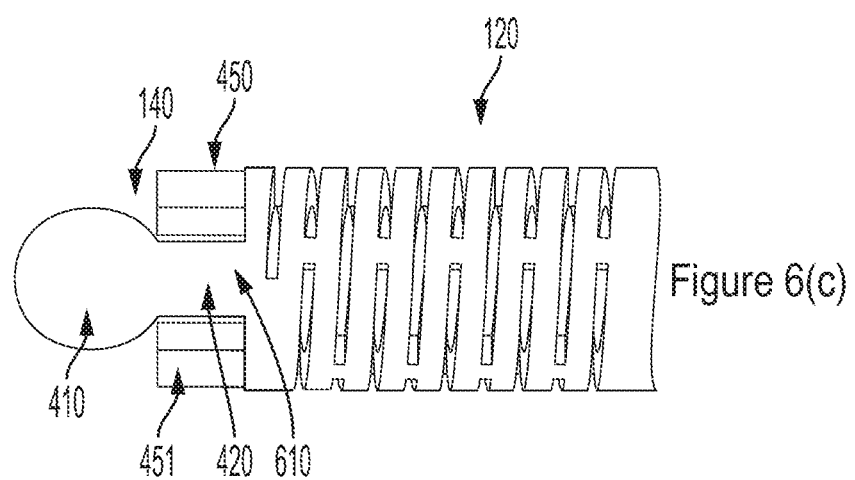

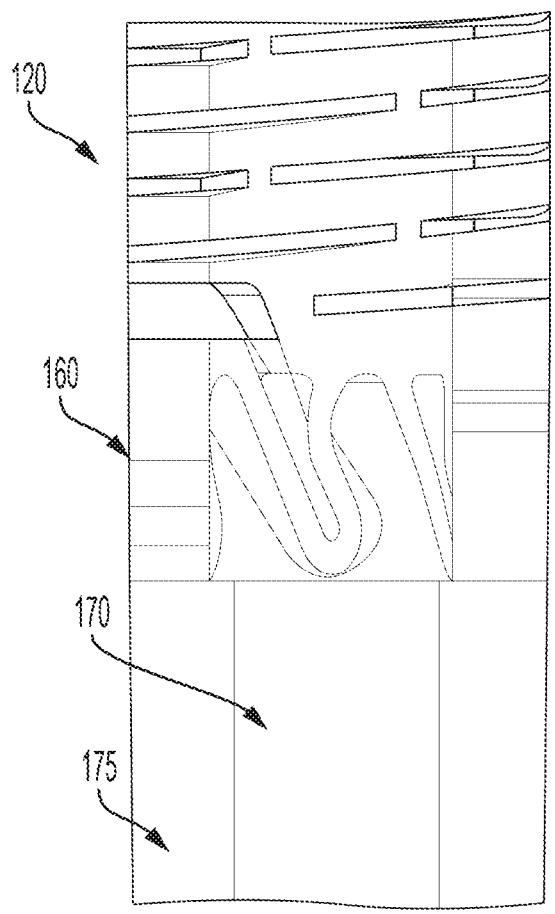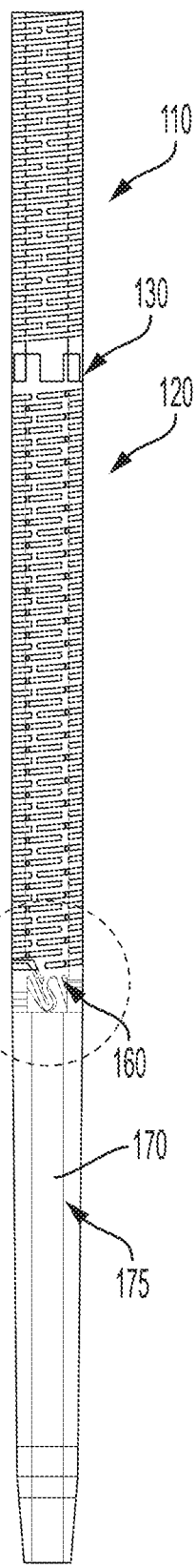
Figure 16(b)
Figure 16(a)

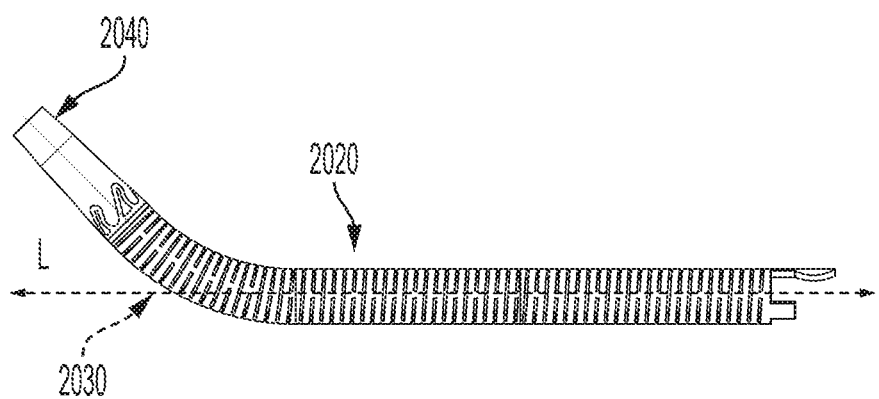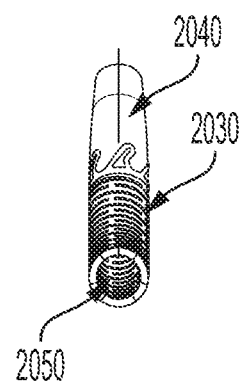
Figure 20(a)         Figure 20(b)
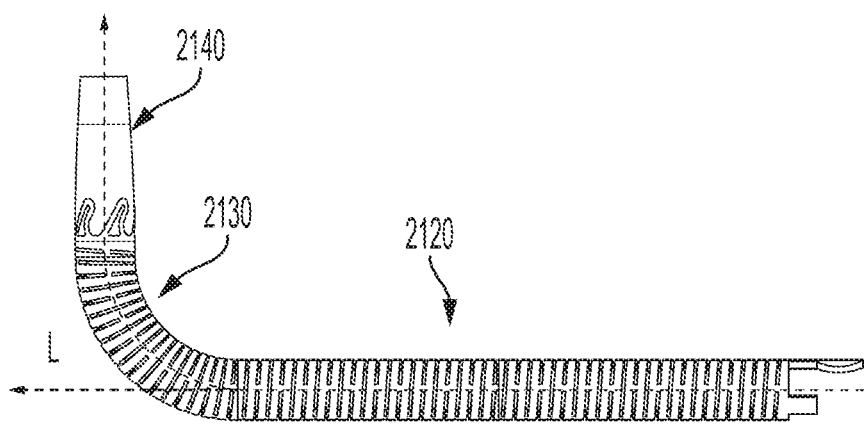
Figure 21(a)         Figure 21(b)
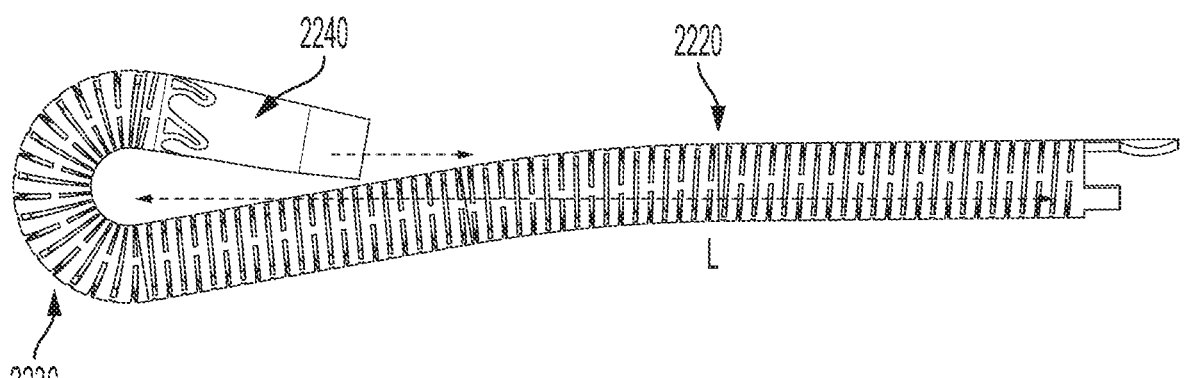
Figure 22

MODULAR VASCULAR CATHETER

CROSS-REFERENCE TO RELATED APPLICATIONS

This application claims the benefit of and priority to U.S. Provisional Application No. 62/404,552, filed Oct. 5, 2016.

BACKGROUND

Currently, there are a large number of different vascular catheters and microcatheters, each designed to enable access to different anatomical locations in the vasculature. A key issue that catheter design faces is controlling pushability and flexibility across the length of the catheter. Controlling pushability and flexibility is important in order to enable the physician to negotiate access through various complex and often tortuous, anatomical vasculature which is often found in the cardiovascular or neurovascular systems. One approach to modulating flexibility is to form the catheter body from different types of materials, e.g., stainless steel and or polymers, each of which has different functional properties. These materials may be combined into a tubular construction via a coiled or braid wire pattern set within a layered polymer composition. Another approach is to vary the cylindrical diameter and wall thickness of the catheter. Alternatively, a variety of different spiral-cuts can be introduced into the wall of the catheter, thereby increasing flexibility; these spiral cuts can either be continuous or discontinuous in nature. However, there are no current catheters which combine both different types of materials as well as different cut patterns in easy-to-assemble modules. Assembling a catheter from multiple modules, each of which is made from a different material, can be difficult because the physical properties of these materials make functional combination problematic, i.e., a stainless steel tube cannot be fused directly to a nitinol tube. However, assembling a catheter from different modules, each of which had different properties, would allow one to tailor the catheter to meet the particular requirements of different types of vascular anatomy.

The present invention provides a way for assembling catheter modules each having different physical properties. The catheter properties can be tailored directly to meet a particular anatomical need. Thus, it is possible to specifically control flexibility, resistance to plastic deformation, axial torque transmission, and column strength of the catheter in an anatomically specific manner. The modular catheters of the present invention are particularly useful for supporting a guidewire and/or delivering an agent through a vessel stenosis or tortuous anatomy as is often encountered in the cardiovascular or neurovascular systems.

SUMMARY OF THE INVENTION

Embodiments of the present invention provide a catheter that comprises at least one proximal tubular module and a distal tubular module, each of the tubular modules having at least one section with spiral cuts, each pair of adjacent tubular modules are coupled by a joint, the joint comprising, (a) at least one snap-fit connector on a first tubular module and a snap-fit acceptor positioned on the adjacent tubular module, the snap-fit connector being elastically deformable when engaged, and (b) at least one stabilizing element, including, a tongue element positioned on the first tubular module or the adjacent tubular module, and a groove element positioned on the opposite, first tubular module or the opposite, adjacent tubular module.

In some implementations, the spiral-cuts comprise a plurality of interrupted spiral cuts.

The snap-fit connector may form a cantilever joint. In further implementations, the snap-fit connectors comprise a stem structure and a locking structure, wherein the width of the locking structure at the widest point as measured between opposite sides of the locking structure is greater than the width of the stem structure, and the snap-fit acceptor comprise a stem void and a locking void and wherein the width of the locking void at the widest point measured between opposite sides of the locking void is greater than width of the stem void. In certain embodiments, the locking structure can be formed in an oval shape and the snap-fit acceptor comprises a locking void formed in a circular shape. The snap-fit connector can bend at the cantilever joint at an angle ranging from about 0.1 to about 90° with respect to a line parallel to a longitudinal axis running parallel with one of the at least one proximal tubular modules or the distal tubular module.

In some embodiments, the snap-fit connector forms a barb structure which when inserted into the snap-fit acceptor, then, after insertion deploys laterally and remains parallel during and after insertion with respect to a line parallel to the longitudinal axis of one of the at least one proximal tubular modules or the distal tubular module. In some implementations, the barb structure comprises an arrow shaped structure formed from two shafts.

In some embodiments, the distal tubular module is formed from Nitinol. Alternatively, the distal module can be formed from stainless steel of SAE grade selected from 304, 316, 402, and 440, 17-7 precipitation hardened stainless steel (PH), or Nickel Cobalt Alloy (MP35N).

To protect the joint between adjacent tubular modules, at least a portion of the joint can be enclosed with a tubular cover.

The catheter can comprise at least two cut openings, a first and a second cut opening that are positioned on the at least one proximal tubular modules or the distal tubular module. In some implementations, both cut openings are positioned on the distal tubular module. In other implementations, one cut opening is positioned on the distal tubular module and the second cut opening is positioned on one of the at least one proximal tubular modules. In some implementations, a filament is threaded in a spiral configuration around the outside of a tubular module. One end of the filament is positioned in the first cut opening and the other end of the filament is positioned in the second cut opening.

The filament can be fixed in position at the first and second openings. The filament can also be threaded in either clockwise or counterclockwise configuration around the one or more tubular modules on which is included. The filament can be fixed on one or more of the proximal tubular modules or the distal tubular module by at least one ring. In addition, the cross-sectional area of the filament can be circular, square, triangular, rectangular, half-circle or trapezoidal in shape.

In some embodiments, the catheter comprises between 2 and 20 tubular modules.

In some implementations, a polymer forming a jacket may be used to cover at least a portion of one or more of the at least one proximal tubular modules or the distal tubular module. In some implementations, the polymer jacket may be formed from nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone).

In some embodiment of the catheter according to the present invention, the at least one proximal tubular module and the distal tubular module include an inner lumen and wherein at least a portion of the inner lumen of the proximal or distal tubular modules is coated with an inner lining. In some implementations, the inner lining may be formed from nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone).

There are a number of ways in way the snap-fit connector and snap-fit acceptor can be secured to ensure a robust connection between adjacent tubular modules. For instance, the snap-fit connector and snap-fit acceptor can be glued together, welded together, and soldered to each other.

The at least one proximal tubular module and the distal tubular module can be formed from the same material or alternatively, from different materials. In certain embodiments, one or more of the at least one proximal tubular module is formed from stainless steel and the distal tubular module is formed from Nitinol. In some embodiments, one or more of the at least one tubular module and the distal tubular module is formed from a polymer. In some implementations, one or more of the at least one proximal tubular module and the distal tubular module is formed from a braided composite of metal and polymer.

In some embodiments, the outer diameter of a proximal tubular module adjacent to the distal tubular is the same as the outer diameter of the distal tubular module. In alternative embodiments, the outer diameter of the adjacent proximal tubular module is greater than the outer diameter of the distal tubular module.

In some implementations, the inner diameter of the distal tubular module is smaller than the inner diameter of the adjacent proximal tubular module. Alternatively, the inner diameter of the adjacent proximal tubular module can be equal to the inner diameter of the distal tubular module.

One or more of the at least one proximal tubular modules can have the same flexibility as the distal tubular module. Alternatively, the distal tubular module can have a greater flexibility than the flexibility of one or more of the at least one proximal tubular modules.

In some embodiments, the distal end of the distal tubular module has a crown. In some implementations, the crown comprises a plurality of curvilinear elements. In particular implementations, the crown comprises 5-20 curvilinear elements. The curvilinear elements may be sinusoidal in shape.

In embodiments of the catheter of the present invention, the catheter further comprises a tip that is attached to the crown of the distal tubular module. In some embodiments, the tip is tapered and further comprises radiopaque material impregnated within the tip material. The tip may be from a metal, such as, but not limited to, gold. The tip can be implemented as a hollow tubular body that is conically tapered. A filament may be spirally wound around a distal portion of the distal tubular module and the tip, and both the filament and tip can be covered with a jacket.

In some embodiments, the catheter is coated a hydrophilic lubricating polymer.

Embodiments of the catheter of the present invention also provide a catheter that comprises at least one proximal tubular module and a distal tubular module, each of the tubular modules having at least one section with spiral cuts, each pair of adjacent tubular modules being coupled by a joint, the joint comprising an interlocking shape having a plurality of protruding sections and receiving sections that mate with the protruding sections, each of the adjacent tubular modules in the pair having one or more of the plurality of protruding sections and the plurality of receiving sections.

In some implementations, the interlocking shape of the joint comprises a pattern of zig-zags. Alternatively, the interlocking shape of the joint comprises a wave form. The catheter joint may be covered with a jacket.

In some embodiments of the catheter of the present invention, the distal tubular module comprises at least one least one section having a spiral-cut, distal tubular module is formed from a shape-memory metal, wherein a segment or section of the distal tubular module is set in a curvilinear shape along a central luminal axis of the tubular module such that a constant cross-sectional lumen is maintained around the central luminal axis when the curvilinear shape is assumed by the distal tubular module. In some embodiments, At least a portion of the distal tubular module may be formed from Nitinol. In other embodiments, the distal tubular module is formed from a stainless steel material selected from the group of consisting of a stainless steel of SAE grade selected from 304, 316, 402, and 440, 17-7 precipitation hardened stainless steel (PH), Nickel Cobalt Alloy (MP35N) and mixtures thereof. Alternatively, the distal tubular module can be formed from a polymer. In some implementations, the section of the distal tubular module set in a curvilinear shape along maintains an angle ranging from about 0° to about 90° with respect with a segment of the distal tubular module not set in a curvilinear shape. In other embodiments the section of the distal tubular module set in a curvilinear shape along maintains an angle ranging from about 0° to about 180° with respect with a segment of the distal tubular module not set in a curvilinear shape. The curvilinear section be straightened using a guidewire. In some embodiments, the guidewire employed is tapered. In some implementations, section of the distal tubular module preset in a curvilinear shape converts to an angle of about 45° with respect with a segment of the distal tubular module not set in a curvilinear shape when the guidewire is withdrawn from the tubular module. In other implementations, the section of the distal tubular module preset in a curvilinear shape converts to an angle of about 180° with respect with a segment of the distal tubular module not set in a curvilinear shape when the guidewire is withdrawn from the tubular module.

BRIEF DESCRIPTION OF THE DRAWINGS

FIG. 1(a) shows a front view of one embodiment of modular catheter the present invention.

FIG. 1(b) shows a blown up view of a portion of the embodiment shown in FIG. 1(a).

FIG. 2(a) shows side view of the embodiment shown in FIG. 1(a).

FIG. 2(b) shows an embodiment of an interrupted spiral cut pattern incorporated in one or both of the proximal and distal tubular modular according to the present invention.

FIG. 2(c) shows another embodiment of an interrupted spiral cut pattern according to the present invention.

FIG. 2(d) shows another embodiment of an interrupted spiral cut pattern according to the present invention.

FIG. 2(e) shows a plan view of a snap-fit joint used to couple tubular modules according to the present invention.

FIG. 2(f) shows another embodiment of an interrupted spiral cut pattern according to the present invention.

FIG. 2(g) shows another embodiment of an interrupted spiral cut pattern according to the present invention.

FIG. 2(h) shows another embodiment of an interrupted spiral cut pattern according to the present invention.

FIG. 2(i) shows another embodiment of an interrupted spiral cut pattern according to the present invention.

FIG. 10(e) shows a joint covered with crimped metal and FIG. 10(f) shows a joint 137 covered with crimped metal 1036.

FIG. 16(a) shows a cross-sectional view of a modular catheter having an elongated tip attached to a distal tubular module according to an embodiment of the present invention.

FIG. 16(b) is an enlarged view of the section of FIG. 16(a) outlined in dashed line.

FIG. 20(a) shows a side view of a distal tubular module having a flexible hooking section with shape memory according an embodiment of the present invention.

FIG. 20(b) shows an end view of the distal tubular module of FIG. 20(a).

FIG. 21(a) shows a side view of a distal module having a flexible, curvilinear section using material shape memory according to another embodiment of the present invention.

FIG. 21(b) shows an end view of the distal tubular module of FIG. 21(a).

FIG. 22 shows a side view of a portion of a distal tubular module having a flexible curvilinear section using material shape memory according to an embodiment of the present invention.

DETAILED DESCRIPTION

Figure 3:
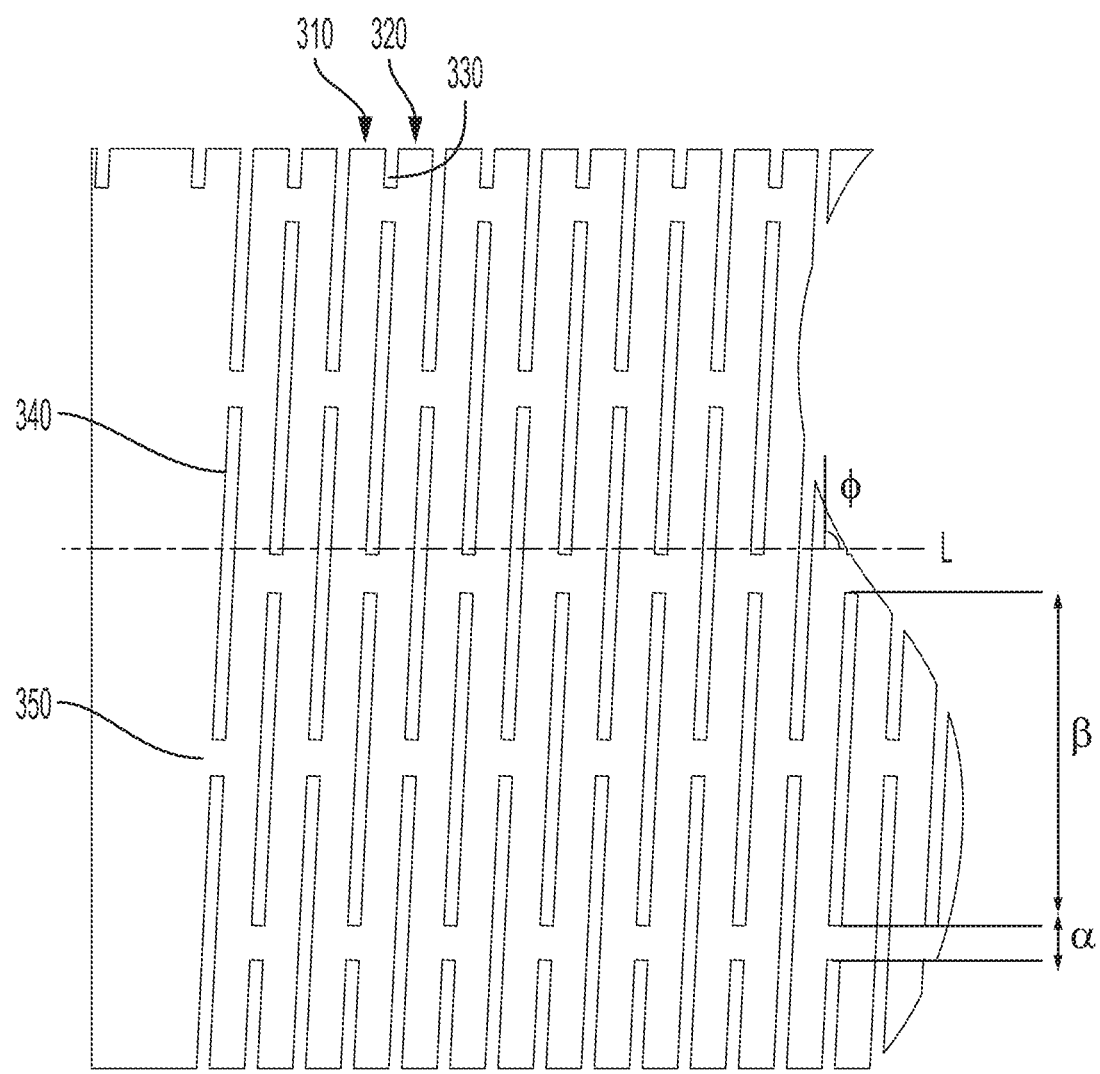
FIG. 3 shows a flattened view of an embodiment of an interrupted spiral-cut pattern according to the present invention.

Referring to FIGS. 1(a) and 1(b), a catheter 100 is formed from at least two tubular modules 110, 120, generally referred to as a proximal 110 and distal 120 tubular modules. Each tubular module has at least one section which can have at least one spiral-cut section. The spiral-cut section may extend along the full length of the tubular module or may be positioned only along one or more portions of the tubular module. The spiral-cut may be continuous or form an interrupted spiral pattern. In certain embodiments, there may be more than two tubular modules, e.g., 2, 3, 4, 5, 6, 7, 8, 9, 10, 11, 12, 13, 14, 15, 16, 17, 18, 19, 20 . . . or up to n, tubular modules linked together. If there are multiple tubular modules, e.g., >2 tubular modules, the additional tubular modules serve or act as extensions of the proximal, tubular module. The tubular modules may be formed from hypotubes, which in certain embodiments may contain patterned cuts positioned on one end of the tubular module. The tubular modules may be formed from the same or different materials and may have the same or different outer or inner diameters. For example, the tubular modules can be made from similar metals (metals having similar physical properties, e.g., ultimate tensile strength (UTS), % elongation, or modulus of elasticity), two different metals, polymers, or formed from a combination of polymers and metals.

In one embodiment, the tubular modules may be joined together by a plurality of snap-fit connectors and snap-fit acceptors which are positioned on one end of either the same or different adjacent tubular modules.

The structure of the snap-fit connectors may vary. For example, in one embodiment, the snap-fit connector comprises a stem structure and a locking structure. The width of the locking structure at the widest point, as measured between opposite sides of the locking structure, is greater than width of the stem structure at its widest point, as measured between opposite sides of the stem. The shape of locking structure can vary. In one embodiment, the locking structure is an oval, while in a second embodiment, the shape is circular or semicircular. Other shapes for the locking structure are encompassed by the invention, including, square, rectangular, trapezoidal, diamond or triangular.

The snap-fit acceptor comprises a stem void and a locking void and, is positioned opposite the snap-fit connector on the opposing or adjacent tubular module. The structure of the snap-fit acceptor is the cut-out image corresponding to the geometric structure of the snap-fit connector.

FIGS. 1(a) and (b) show an overview of the structure of the catheter 100. In the embodiment shown, there are two tubular modules, a proximal tubular module 110 and a distal tubular module 120. As used herein, the terms "proximal" and "distal" refer to the proximity of the tubular module to the hub 190 or the proximity to the cardiovascular system. In other words, the proximal tubular module is positioned closer to the hub 190 and more distant, as measured along the length of the catheter, from the heart, while the distal module is positioned closer to the heart and, thus, the coronary arteries. However, these terms only denote relative position and are not limiting with respect to the structure, length, shape or number of the tubular modules.

The proximal and distal tubular modules can be made from similar metals, different metals, polymers, or a combination of polymers and metals. Examples of materials that may be used include stainless steel (SST), nickel titanium (Nitinol), or polymers. Examples of other metals which may be used include, super elastic nickel titanium, shape memory nickel titanium, Ti—Ni, nickel titanium, approximately, 55-60 wt. % Ni, Ni—Ti—Hf, Ni—Ti—Pd, Ni—Mn—Ga, Stainless Steel (SST) of SAE grade in the 300 to 400 series e.g., 304, 316, 402, 440, MP35N, and 17-7 precipitation hardened (PH) stainless steel, other spring steel or other high tensile strength material or other biocompatible metal material. In one preferred embodiment, the material is superelastic or shape memory, nickel titanium, while in another preferred embodiment, the material is stainless steel.

The proximal and distal modules of present invention can include, in entirety, or in only in selected sections, a superelastic alloy generally referred to as "a shape-memory alloy." Elements made of such shape memory alloys have the ability to resume their original shape after being deformed to such a degree that if they were made from an ordinary metal, they would undergo permanent deformation. Superelastic alloys useful in the invention include: Elgiloy® and Phynox® spring alloys (Elgiloy® alloy is available from Carpenter Technology Corporation of Reading Pa.; Phynox® alloy is available from Metal Imphy of Imphy, France), SAE grade 316 stainless steel and MP35N (Nickel Cobalt) alloys which are available from Carpenter Technology corporation and Latrobe Steel Company of Latrobe, Pa., and superelastic Nitinol which is available from Shape Memory Applications of Santa Clara, Calif. Further information regarding one or more of these alloys is disclosed in U.S. Pat. No. 5,891,191.

The term "superelastic" refers to alloys having superelastic properties that include at least two phases: a martensitic phase, which has a relatively low tensile strength and which is stable at relatively low temperatures; and an austenitic phase, which has a relatively high tensile strength and which is stable at temperatures higher than the martensitic phase. Superelastic characteristics generally allow the metal to be deformed by collapsing and deforming the metal and creating stress which causes the Nitinol to change to the martensitic phase. More precisely, when stress is applied to a specimen of a metal such as Nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation. If the load on the specimen is removed before any permanent deformation has occurred, the martensitic specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity.

As discussed above, suitable superelastic alloys include nickel titanium (Nitinol) consisting essentially of 49 to 53 atom percent of Ni, Cu—Zn alloy consisting essentially of 38.5 to 41.5 wt % of Zn, Cu—Zn—X alloy containing 1 to 10 wt % of X (X=Be, Si, Sn, Al, or Ga), and Ni—Al alloy consisting essentially of 36 to 38 atom percent of Al. Nitinol is especially preferable. The mechanical properties of Nitinol can be changed as desired by replacing part of Ti—Ni alloy with 0.01 to 30.0 atom percent of another element X (X=Cu, Pd, or Zr) or selecting the reduction ratio of cold working and/or the conditions of the final heat treatment. The buckling strength yielding stress when a load is increased) of the super elastic alloy used is 5 to 200 kg/mm$^2$ (22° C.), preferably 8 to 150 kg/mm, and the recovery stress (yielding stress when a load is decreased) is 3 to 180 kg/mm$^2$ (22° C.), preferably 5 to 130 kg/mm$^2$. Alternatively, the tubular modules may be formed from polymers. Examples of polymers include polyimide, PEEK, nylon, polyurethane, polyethylene terephthalate (PET), latex, HDHMWPE (high density, high molecular weight polyethylene) and thermoplastic elastomers.

The tubular modules may be made, for example, by forming a pipe of a super elastic metal and then removing the parts of the pipe where the notches or holes are to be formed. The notches, holes or cuts can be formed in the pipe by laser (YAG laser, for example), electrical discharge, chemical etching, mechanical cutting, or a combined use of any of these techniques. See U.S. Pat. No. 5,879,381 to Moriuchi et al., which is incorporated by reference herein, in its entirety.

After deformation by heating and deformation into a preset shape, e.g., a curvilinear shape, the tubular module can be cooled. The tubular module is then restrained in the deformed condition within a delivery system to facilitate the insertion into an artery. Once the physical restraint on the tubular module is removed, the superelastic tubular module can return to its original undeformed shape, i.e., curvilinear.

In one embodiment, the proximal tubular module 110 may be made of 316 SST and the distal tubular module 120 is made of 17-7 SST. In another embodiment, the proximal tubular module 110 is made of 17-7 SST, while the distal tubular module 120 is made of Nitinol. Either the proximal tubular module 110 or the distal tubular module 120 may be made from a braided composition of materials as well. In other embodiments, either the proximal tubular module 110 or the distal tubular module 120 may be made from a cable or a braided wire.

Each tubular module 110, 120 may have several different types of spiral-cut patterns, including both continuous as well as discontinuous spiral-cut patterns. The different spiral-cut patterns may be distributed on the same or different tubular modules.

The spiral-cut sections provide for a graduated transition in bending flexibility, as measured by pushability, kink resistance, axial torque transmission for rotational response, and/or torque to failure. For example, the spiral-cut pattern may have a pitch that changes to increase flexibility in one or more areas of the tubular module. The pitch of the spiral-cuts can be measured by the distance between points at the same radial position in two adjacent threads. In one embodiment, the pitch may increase as the spiral-cut progresses from a proximal position to the distal end of the catheter. In another embodiment, the pitch may decrease as the spiral-cut progresses from a proximal position on the catheter to the distal end of the catheter. In this case, the distal end of the catheter may be more flexible. By adjusting the pitch and the cut as well as the uncut path of the spiral-cuts, the pushability, kink resistance, torque, flexibility and compression resistance of the catheter, i.e., the tubular modules, may be adjusted. Thus, tubular modules having different rigidity or flexibility can be combined. For example, a comparatively rigid tubular module could be combined with relatively flexible tubular module. This combination could be further combined with a comparatively rigid of comparatively flexible tubular module.

By combining tubular modules with varying rigidity (conversely, flexibility), the catheter can traverse within a wide variety of different vasculature, especially, when the vascular anatomy is torturous or the lumen of the vasculature is compromised or obstructed, partially or completely, such as a Chronic Total Occlusion (CTO). The modular structure also provides for the ability to effectively transmit torque across the length of the catheter without kinking or narrowing or collapse of the lumen of the tubular modules. This combination of tubular modules with varying rigidity or flexibility allows the flexibility of the catheter to be adjusted across its length. In addition, the varying rigidity enables the flexibility of modular sections to go from more rigid to more flexible and then back to rigid again. This modulation of flexibility/rigidity across the length of the catheter allows it to be advanced into and function in various anatomical lumens and across lumen obstructions.

The modulation of flexibility/rigidity across the length of the catheter can be accomplished in a number of ways. For example, by varying the spiral-cut pattern variables (pitch, interruptions) and transitioning between spiral-cut patterns the flexibility/rigidity of a tubular module may be controlled. In addition, the spiral-cut pattern allows the cross-sectional diameter of the lumen to be maintained when the tubular module is bent or curved. Spiral-cut sections having different cut patterns may be distributed along the length of the tubular module. The spiral-cut patterns may be continuous or discontinuous along the length of the module. For example, there may be 1, 2, 3, 4, 5, 6, 7, . . . n spiral-cut sections along the length of the module. The spiral-cut sections may be continuous or interrupted. Within each section a constant cut pattern may be present, but across different sections within a tubular module, the cut patterns may vary, e.g., in terms of pitch. Each section may also contain a variable pitch pattern within the particular section. Each spiral-cut section may have a constant pitch, e.g., in the range of from about 0.05 mm to about 10 mm, e.g., 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, 2.5 mm, 3.0 mm, 3.5 mm, 4.0 mm, etc. The pitch may also vary within each section. The pitches for different spiral-cut sections may be same or different. Alternatively, the catheter may be formed from tubular modules have a continuously changing spiral-cut pattern along the length of the catheter. The orientation or handedness of spiral-cut sections in the modules may also vary within the spiral-cut sections.

The width of the spiral cuts can vary, e.g., from about 1 micron to about 100 microns.

For an interrupted spiral-cut section, the interrupted spiral pattern can be designed such that each turn or rotation of the spiral includes a specific number of cuts, Nc (e.g., 1.5, 2.5, 3.5, 4.5, 5.5, etc.). Nc can also be whole numbers, such as 2, 3, 4, 5, . . . n, as well as other real numbers, such as 2.2, 2.4, 2.7, 3.1, 3.3, etc. At a given Nc, the uncut extent α and the cut extent β can be chosen as α=(360−(β*Nc))/Nc such that each rotation has Nc number of repeat patterns each comprising a cut portion of extent β adjacent an uncut portion of extent α. For example, at Nc=1.5, 2.5, and 3.5, the following table shows example choices of various embodiments for α and β:

| Nc = 1.5 | | Nc = 2.5 | | Nc = 3.5 | |
|---|---|---|---|---|---|
| β (°) | α (°) | β (°) | α (°) | β (°) | α (°) |
| 230 | 10 | 140 | 4 | 90 | 12.13 |
| 229 | 11 | 139 | 5 | 89 | 13.13 |
| 228 | 12 | 138 | 6 | 88 | 14.13 |
| 227 | 13 | 137 | 7 | 87 | 15.13 |
| 226 | 14 | 136 | 8 | 86 | 16.13 |
| 225 | 15 | 135 | 9 | 85 | 17.13 |
| 224 | 16 | 134 | 10 | 84 | 18.13 |
| 223 | 17 | 133 | 11 | 83 | 19.13 |
| 222 | 18 | 132 | 12 | 82 | 20.13 |
| 221 | 19 | 131 | 13 | 81 | 21.13 |
| 220 | 20 | 140 | 14 | 80 | 22.13 |
| 219 | 21 | 129 | 15 | 79 | 23.13 |
| 218 | 22 | 128 | 16 | 78 | 24.13 |
| 217 | 23 | 127 | 17 | 77 | 25.13 |
| 216 | 24 | 126 | 18 | 76 | 26.13 |
| 215 | 25 | 125 | 19 | 75 | 27.33 |
| 214 | 26 | 124 | 20 | 74 | 28.13 |
| 213 | 27 | 123 | 21 | 73 | 29.13 |
| 212 | 28 | 122 | 22 | 72 | 30.13 |
| 211 | 29 | 121 | 23 | 71 | 31.13 |
| 210 | 30 | 120 | 24 | 70 | 32.13 |
| 209 | 31 | 119 | 25 | 69 | 33.13 |
| 208 | 32 | 118 | 26 | 68 | 34.13 |
| 207 | 33 | 117 | 27 | 67 | 35.13 |
| 206 | 34 | 116 | 28 | 66 | 36.13 |
| 205 | 35 | 115 | 29 | 65 | 37.13 |

FIG. 1(a) shows one embodiment of the catheter in which two tubular modules, a proximal tubular module 110 and distal tubular module 120, are joined together. In the embodiment, shown, a tip, 170, is attached to a crown 160 at a distal end of the distal tubular module 120. The two tubular modules are connected together at a joint 130. The joint 130 is formed by snap-fit connector 140 and snap-fit acceptor 150 as illustrated in FIG. 1(b), where the snap-fit connector 140 is locked-in or snapped into the snap-fit acceptor 150; tubular modules are hollow and have an inner lumen as well as an outer wall. A hub 190 can be positioned at one end of the catheter 100, and an intermediate tubular section 180 connects the hub 190 and proximal tubular module 110. Any type of hub can be used with the catheter.

FIGS. 2(b)-(i) show embodiments of spiral-cut sections of a tubular module that may be used on different portions of the proximal and distal tubular modules shown in FIG. 2(a). The distal tubular module, 120 comprises an interrupted spiral-cut sections 210 (shown enlarged in FIG. 2(b)), 220 (shown enlarged in FIG. 2(c)), and 230 (shown enlarged in FIG. 2(d)) The proximal tubular module 110 comprises interrupted spiral-cut sections 240 (shown enlarged in FIG. 2(f)), 250 (shown enlarged in FIG. 2(g)), 260 (shown enlarged in FIG. 2(h)) and 270 (shown enlarged in FIG. 2(i)). The joint 130 between the proximal and distal tubular modules is shown in FIG. 2(e). Note, in the embodiment shown, the snap-fit connector and span-fit acceptor are flush with the outer surface of the tubular modules, i.e., the outer portions of the snap-fit connector and acceptor do not protrude beyond the outer diameter of the tubular modules.

In the embodiments shown in FIGS. 2(a)-2(i), the interrupted spiral-cuts are represented as being discontinuous. A detailed view of one embodiment of these spiral-cuts is shown in FIG. 3, which depicts a portion of an unrolled (or flattened) tubular module having an interrupted spiral-cut pattern. The spiral-cut tube section of the tubular module shows a single, spiral ribbon portion having adjacent turns 310, 320 which are substantially defined and separated by an interrupted spiral cut path width 330. The spiral cut path width 330 includes alternating open or cut portions 340 and uncut portions 350. The spiral pathway width 330 is composed of alternating cut and uncut sections 340 and 350 is angled with respect to a circumference of the tubular portion (in other words, the pitch angle φ shown in FIG. 3 of less than 90°).

As illustrated in FIG. 3, each helically-oriented uncut portion 350 has an arcuate extent "α" and each helically-oriented cut portion has an arcuate extent "β." Angles α and β can be expressed in degrees (where each complete helical turn is 360°). The uncut portions can be distributed such that adjacent uncut portions 350 are not in axial alignment (or "staggered") with each other along a direction parallel to the longitudinal axis L. As shown in FIG. 3, the uncut portions 350 on every other turn of the interrupted spiral cut width 330 can be axially aligned.

The spiral-cut patterns of each tubular module can be formed from continuous spiral-cut sections, interrupted spiral-cut sections, or a hybrid of both types of spiral-cut patterns, where the various patterns are arranged in any order. The interrupted cut spiral modules have the ability to maintain a concentric lumen area while in a bent configuration, even in sharp bends of small radii. The ability to maintain a concentric lumen enables smooth wire movement, in either direction within the tubular lumen, without resulting in a deformation of the lumen. Additionally, using superelastic materials such as Nitinol for the spiral cut segments, allows segment to bend in tight curves through various vascular passageways without permanent lumen deformation.

The length of each of the tubular modules can vary. For example, the length of the proximal tubular module 110 can range from about 100 cm to about 140 cm, about 120 cm to about 140 cm, about 125 cm to about 135 cm or about 50 cm to 100 cm. The length of the distal tubular module 120 can range from about 15 cm to about 35 cm, about 10 cm to about 25 cm, about 20 cm to about 45 cm, about 30 cm to about 50 cm, about 5 cm to about 15 cm or about 1-5 cm.

In certain embodiments, the distal tubular module may be formed into a microcatheter. The microcatheter is capable of navigating over a guidewire into remote vasculature. The microcatheter may be capable of crossing a lesion and delivering the guidewire and/or contrast media across the lesion followed by, e.g., deployment of an interventional treatment element across the lesion, immediately restoring blood flow.

Figure 4A:
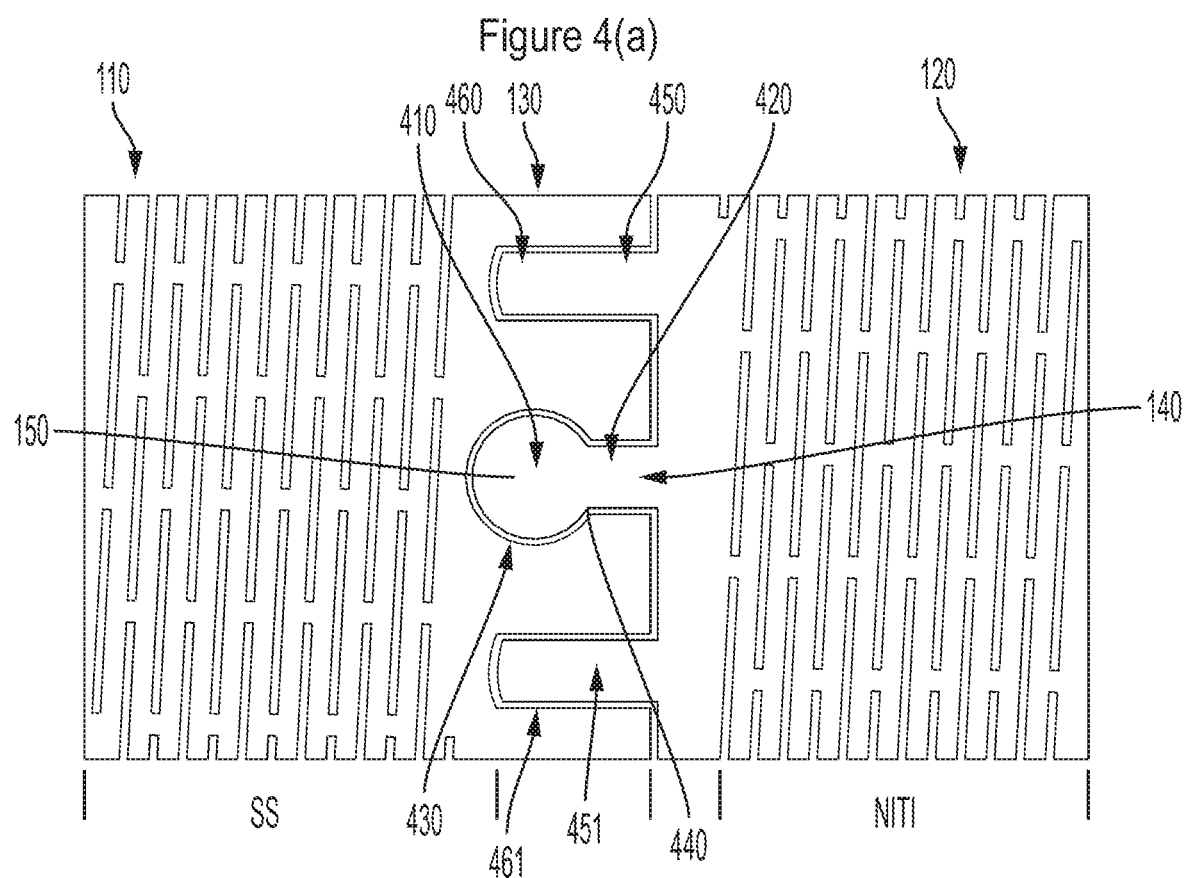
FIG. 4(a) shows an engaged flattened two dimensional view of one embodiment of a snap fit joint having a snap-fit connector and snap-fit acceptor according to an embodiment of the present invention.

The interventional treatment element may be a stent, a coil, a flow diverter, a flow restoration element, a thrombectomy element, a retrieval element, an aspirator or a snare FIGS. 4(a)-(b) and 5(a)-(b) illustrate two different, preferred embodiments of snap-fit connectors and snap-fit acceptors that can be used to couple tubular modules according to the present invention. The embodiments are shown in a two-dimensional representation where the tubular module is flattened in a plane. In FIG. 4(a), the proximal tubular module 110 which in this embodiment is formed from SST, is connected at the joint 130 to the adjacent distal tubular module, which is formed, in this embodiment, from Nitinol, by a snap-fit connector 140 and snap-fit acceptor 150. In addition to the snap-fit connector 140 and snap-fit acceptor 150, two stabilizing elements, 450, 451 may be positioned on either lateral side of the snap-fit connector/snap-fit acceptor 140, 150. In the embodiment shown, the stabilizing elements are rectangular in shape, however, the shape of the stabilizing elements are not limited to a rectangular shape (e.g., trapezoidal, square or triangular).

There may be a plurality of snap-fit connectors and snap-fit acceptors connecting two adjacent tubular modules ranging from 1, 2, 3, 4, 5, 6, 7, 8, 9, 10 . . . n. The snap-fit connector and/or the snap-fit acceptor can be positioned on either the proximal and/or the distal tubular modules. For example, the snap-fit connector can be on the distal tubular module and the snap-fit acceptor can be on the proximal tubular module or, alternatively, the snap-fit connector can be on the proximal tubular module and the snap-fit acceptor can be on the distal tubular module. The snap-fit connector and snap-fit acceptor form a pair on adjacent tubular modules.

The stabilizing elements can prevent the tubular modules from rotating independently, maintain concentric alignment and allow for transmission of torque across the proximal and distal modules along the length of the catheter. The management of torsion and shear stress in the modular catheter is thereby improved. The ratio between the shear stress and strain of a material is an elastic constant of the module (G). When an applied torque is balanced by the internal stress of the material, the torque on the cross-section resulting from sheer stress is:

$$\text{Torque}(T) = G\theta/L * J$$

where θ is the angle of rotation, L is the length of the section and J is known as the "polar second moment of area".

With respect to hollow shafts, such as catheters, the expression for J is:

$$J = \pi(D^4 - d^4)/32$$

where D and d are the outside and inside diameters of the catheter (i.e., tubular modules). These equations yield an indication of the amount of torque that can be safely transferred along a catheter to prevent undue torsion.

Figure 4B:
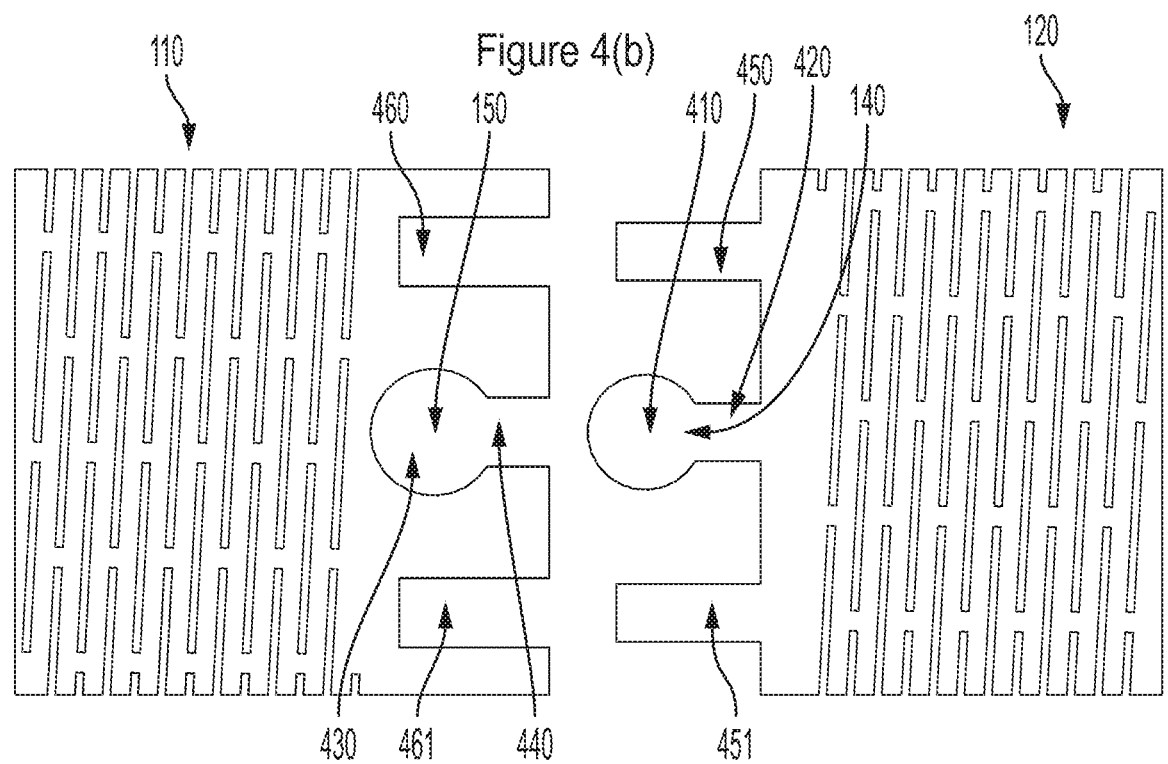
FIG. 4(b) shows the snap-fit joint of FIG. 4(a) separated.

The stabilizing elements can be implemented as tongue elements 450, 451 that fit into corresponding grooves 460, 461 on the opposite tubular module. Also in this embodiment, the snap-fit connector 140 forms a cantilevered joint formed on the distal tubular module 120. In the embodiment shown, the snap-fit connector 140 includes a circular locking section 410 connected to the body of the proximal tubular module by a stem section 420. The proximal tubular module 110 includes a corresponding snap-fit acceptor 150, a space or receptacle, including a circular portion 430 to receive circular section 410 and a rectangular 440 portion to receive the stem section 420. FIG. 4(b) shows the two tubular modules 110, 120, and joint 130 in FIG. 4(a) in an exploded view. The tubular modules are joined together by inserting the snap-fit connector 140 into the snap-fit acceptor 150.

Figure 5A:
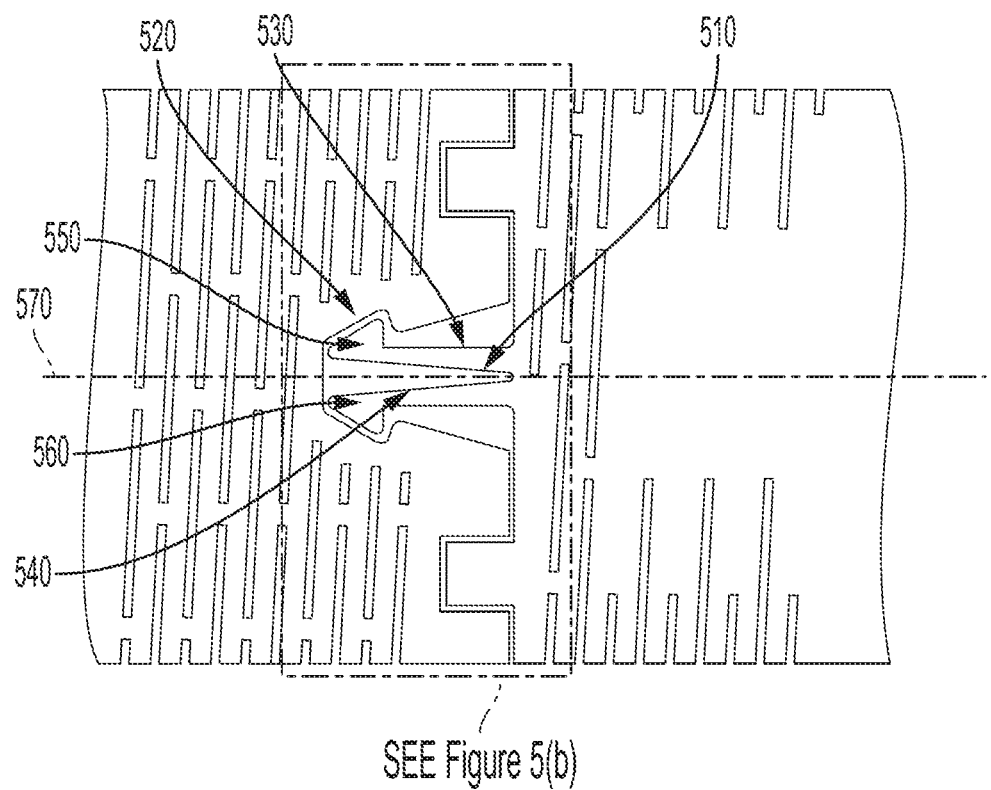
FIG. 5(a) shows a flattened two dimensional view a second embodiment of another embodiment of a snap-fit joint including a snap-fit connector and snap-fit acceptor according to the present invention.
Figure 5B:
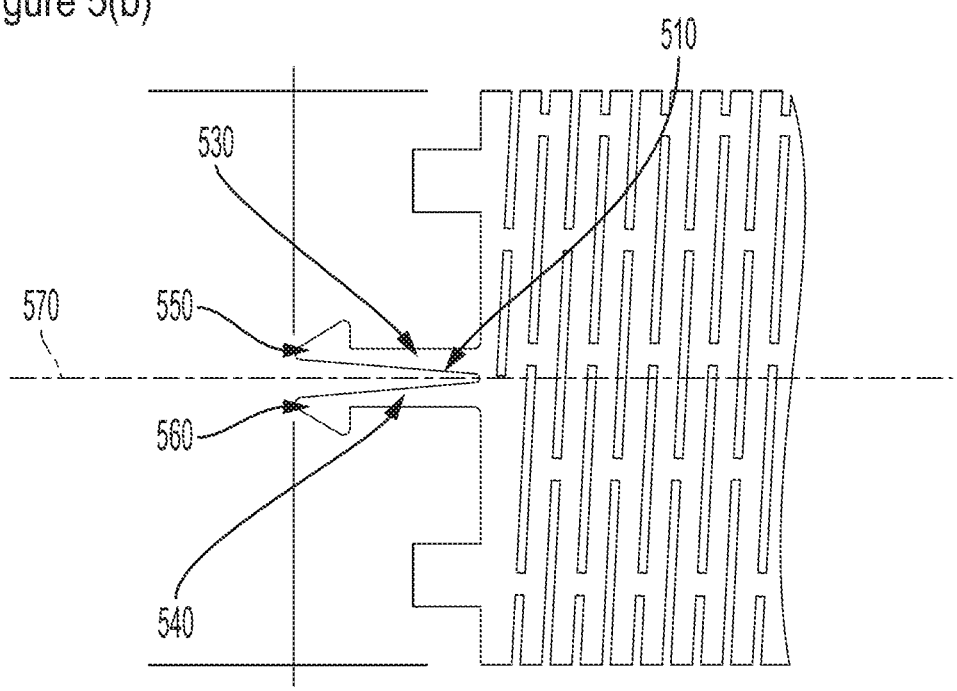
FIG. 5(b) shows a view of the snap-fit connector of the snap-fit joint shown in FIG. 5(a).

FIGS. 5(a) and (b) illustrate another embodiment of a snap-fit joint. In this embodiment, the snap-fit connector, 510, has two arms, 530, 540, each having a respective triangular or trapezoidal shaped head (also referred to as arrow or barb shaped), 550, 560, positioned at one end. The arms 530, 540 have a springiness property and have leeway to pivot laterally with respect to the longitudinal axis, 570, of the tubular module. In FIG. 5(b), the snap-fit connector 510 is shown in the open position in which arms 530, 540, are displaced laterally relative to the longitudinal axis 570 of the tubular module. When inserted into the snap-fit acceptor, 520, the arms 530, 540 pivot inwardly and the angle between the arms and longitudinal axis of the tubular module decreases. After insertion, triangular shaped heads 550, 560 move or flex outwardly again as shown in FIG. 5(a) fixing the snap-fit connector 510 in the snap-fit acceptor 520. In other embodiments, other designs for snap-fit joints can be used including torsion and annular snap joints.

Figure 6D:
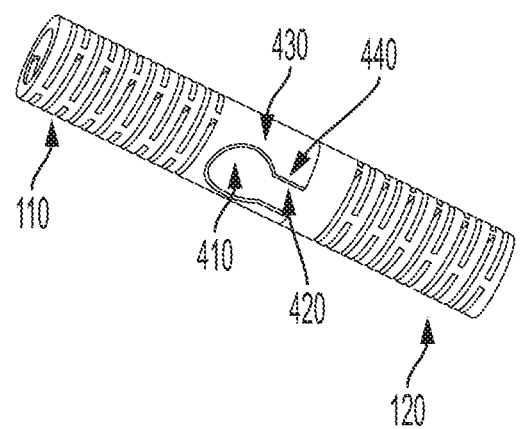
FIG. 6(d) shows a perspective view of the snap-fit joint shown in FIGS. 6(a)-6(c) connecting two tubular modules.
Figure 6E:
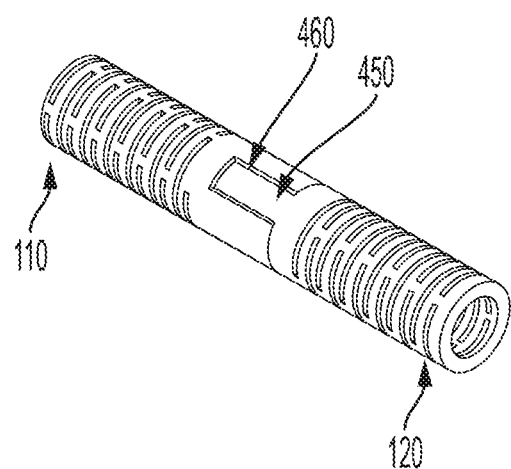
FIG. 6(e) shows a perspective view of a stabilizing element used to secure a snap-fit joint between tubular modules according to an embodiment of the present invention.
Figure 6F:
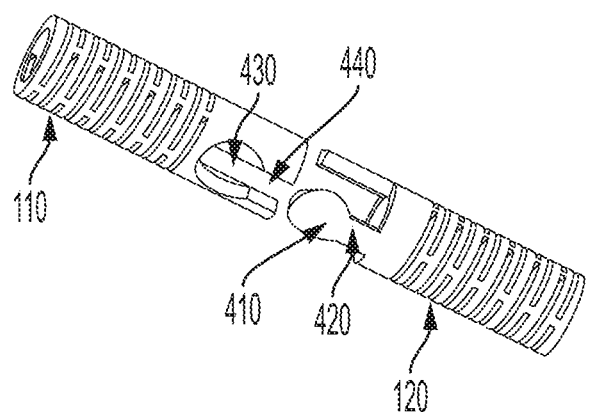
FIG. 6(f) shows a perspective view of the snap-fit joint of FIGS. 6(a)-6(d) in an uncoupled condition.
Figure 6G:
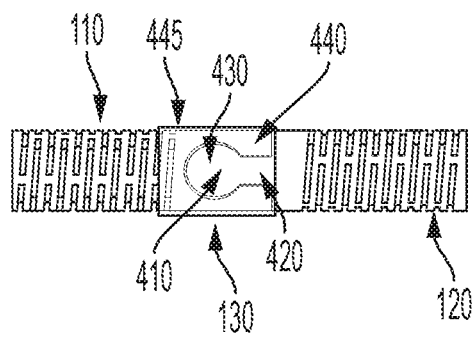
FIG. 6(g) shows another front view of a snap-fit joint according to an embodiment of the present invention.
Figure 6H:
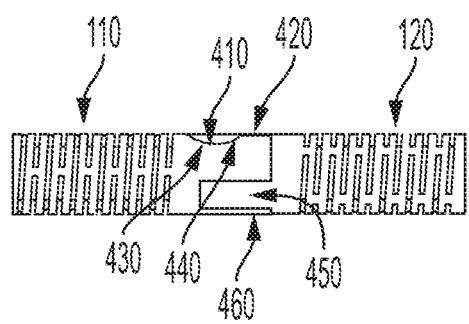
FIG. 6(h) shows a side view (approximately 90° turn) of the snap-fit joint of FIG. 6(g) in which the stabilization element is clearly depicted.
Figure 6I:
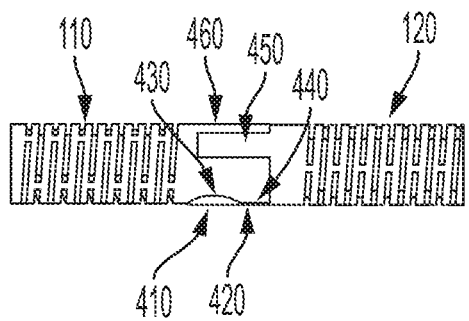
FIG. 6(i) shows another side view (approximately 270° turn) of the snap-fit joint of FIGS. 6(g) and 6(h).
Figure 6J:
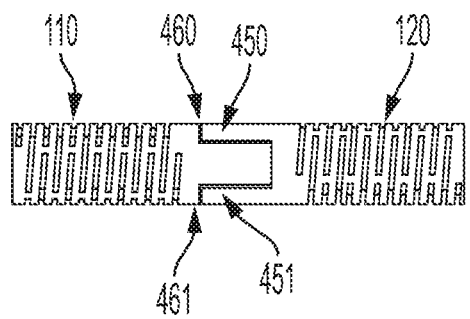
FIG. 6(j) shows a bottom view (approximately 180° turn) of the snap-fit joint of FIG. 6(g) through 6(i).
Figure 6K:
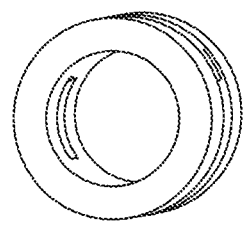
FIG. 6(k) shows a cross sectional view in a plane perpendicular to the longitudinal axis of an embodiment of a tubular module according to the present invention of one embodiment of the present invention.
Figure 6:
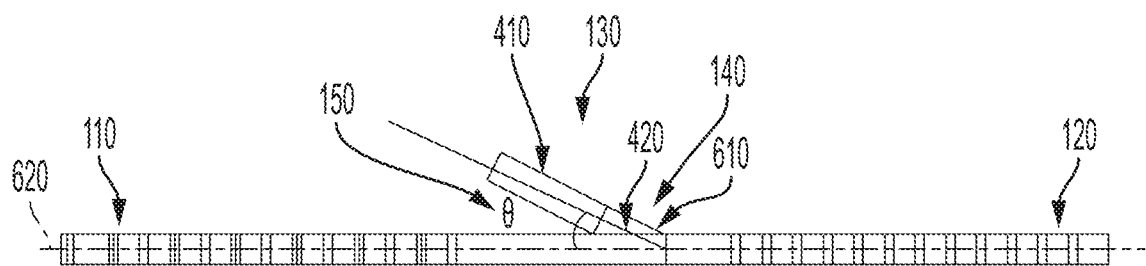
FIG. 6(a) shows a perspective view of an embodiment of a proximal tubular module, distal tubular module and snap-fit joint according to the present invention.
FIG. 6(b) shows another angled perspective view of the embodiment shown in Figure
FIG. 6(c) shows an enlarged plan view of a snap-fit connector at the end of a tubular module according to an embodiment of the present invention.
FIG. 6(l) shows a side, flattened view of a snap-fit joint between tubular modules according to the present invention in which a snap-fit acceptor is cantilevered at an angle to the longitudinal axis of the module according to an embodiment of the present invention in the process of assembly.
FIG. 6(m) shows a perspective, flattened view of the snap-fit joint of FIG. 6(l) shows a bottom, flattened view of the snap-fit joint of FIG. 6(l) in the process of assembly.
FIG. 6(n) shows a top, flattened view of the snap-fit joint of FIGS. 6(l) and 6(m) in the process of assembly.
FIG. 6(o) shows a bottom, reversed view of the snap-fit shown of FIG. 6(l) to 6(n) in the process of assembly.
FIG. 6(p) shows an enlarged side view of a cantilevered snap-fit joint shown in FIG. 6(l) to 6(o) according to an embodiment of the present invention in the process of assembly.
FIG. 6(q) shows an enlarged perspective view of the cantilevered snap-fit joint of FIG. 6(l) to 6(q) in the process of assembly.
FIG. 6(r) shows an exploded perspective view of the cantilevered snap-fit joint of FIG. 6(l) to 6(q) in the process of assembly.
FIG. 6(s) another exploded perspective view of the cantilevered snap-fit joint, as viewed from an angle 90° counterclockwise with respect to the view shown in FIG. 6(r) in the process of assembly.
FIG. 6(t) shows a cross-sectional view of the snap-fit joint in a plane perpendicular to the longitudinal axis of the catheter which illustrates beveling of the snap-fit connector and acceptor in a locked position.

FIGS. 6(a)-6(j) illustrate various perspective views of the embodiment shown in FIGS. 4(a) and (b), where the proximal tubular module 110 and the distal tubular module 120 are linked together using the snap-fit connector 140 and snap-fit acceptor 150, together with stabilizing tongue and groove elements 450, 460. In the embodiment shown in FIGS. 6(a)-6(j), the stabilizing elements 450 and the snap-fit connector 140 are positioned at one end of a single tubular module 120. In other embodiments, the snap-fit connector 140 and the stabilizing elements 450, are positioned and employed on multiple tubular modules. Alternatively, each tubular module can contain a variety of different snap-fit connectors. For example, the snap connector, 140, shown in FIG. 4(a), could be combined with snap connector 510, shown in FIG. 5(b). Additionally, the embodiment shown in FIG. 6(g) shows a tubular cover 445 for the entire joint 130 or only a portion thereof, which can be made of a polymer or other material, e.g., metal.

Figure 6M:
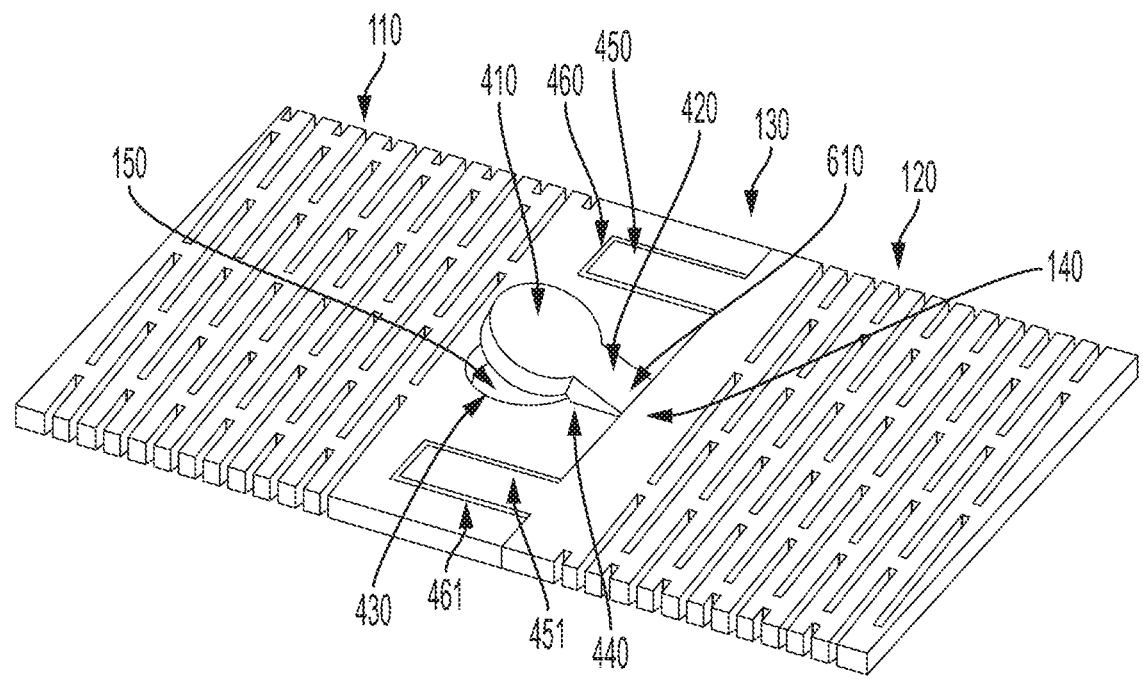
Figure 6N:
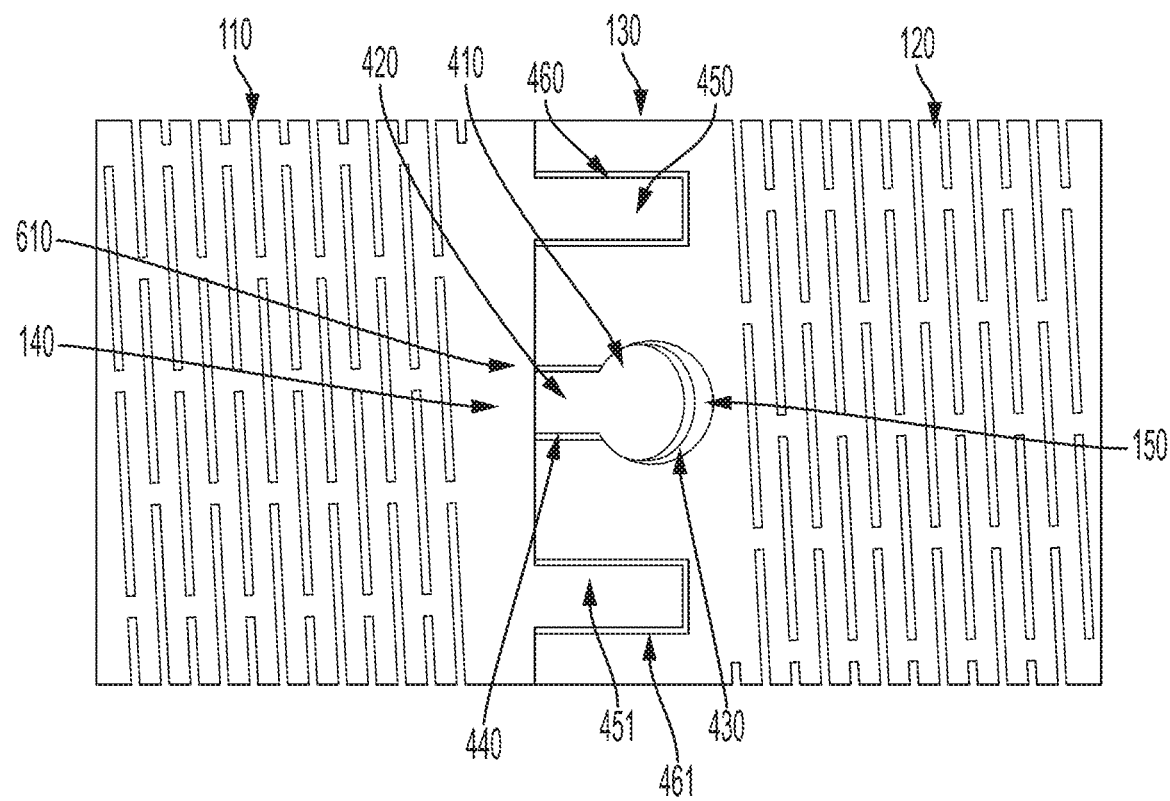
Figure 6O:
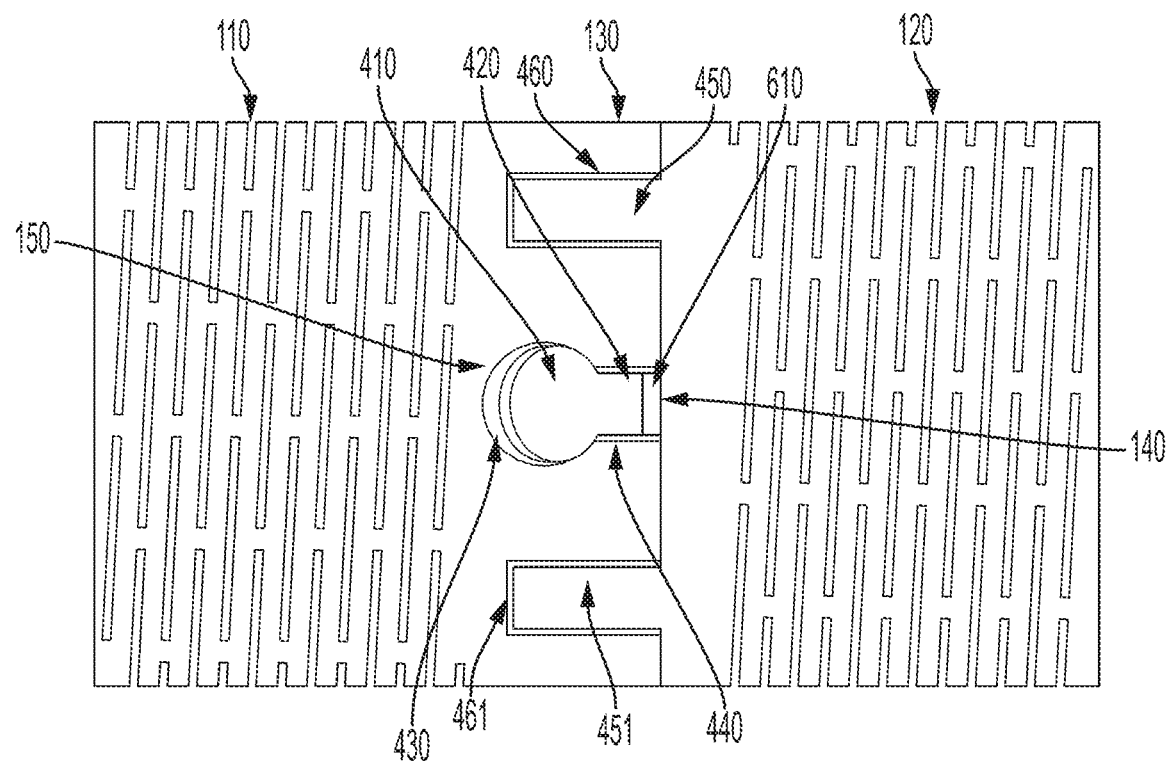
Figure 6P:
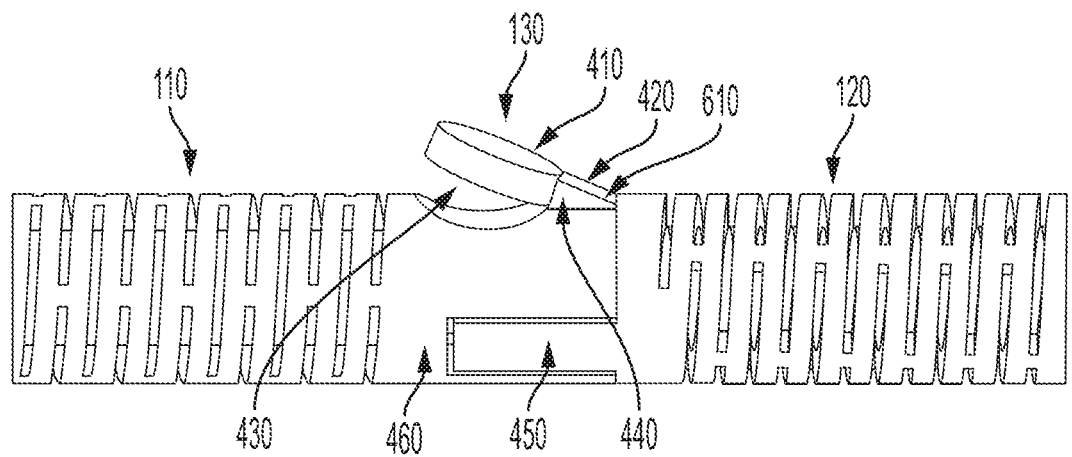
Figure 6Q:
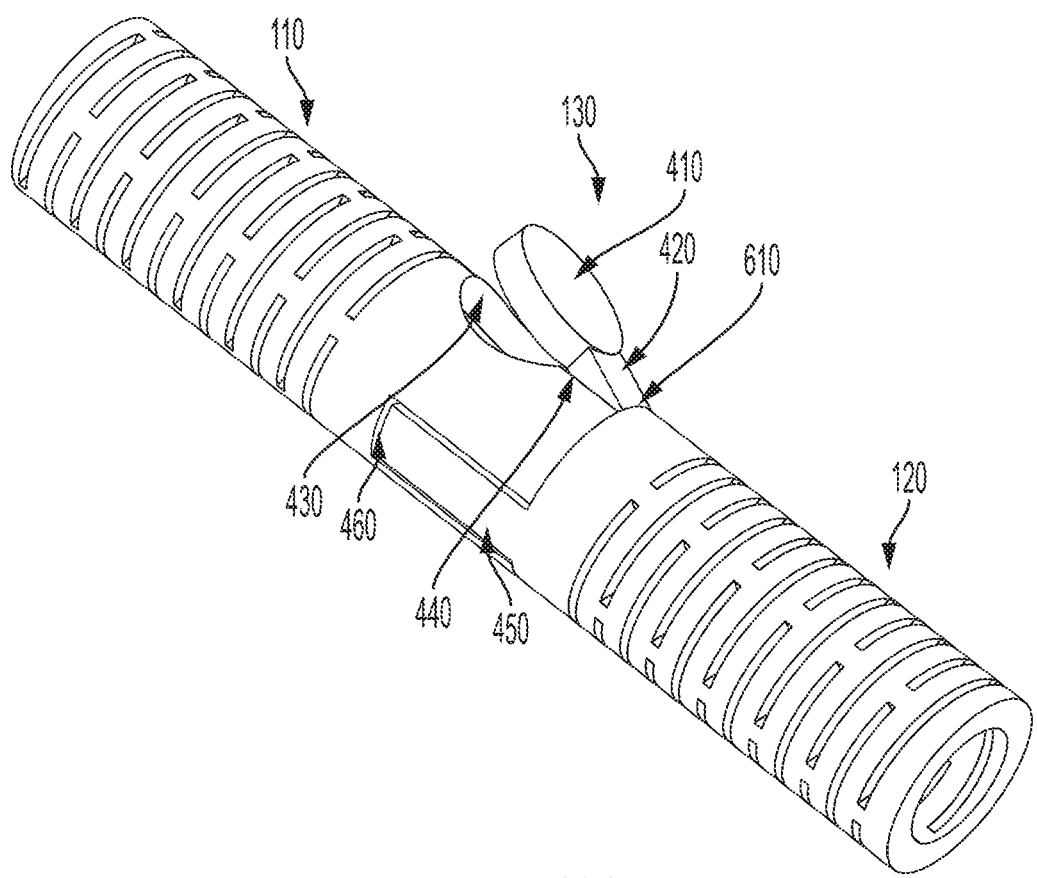
Figure 6R:
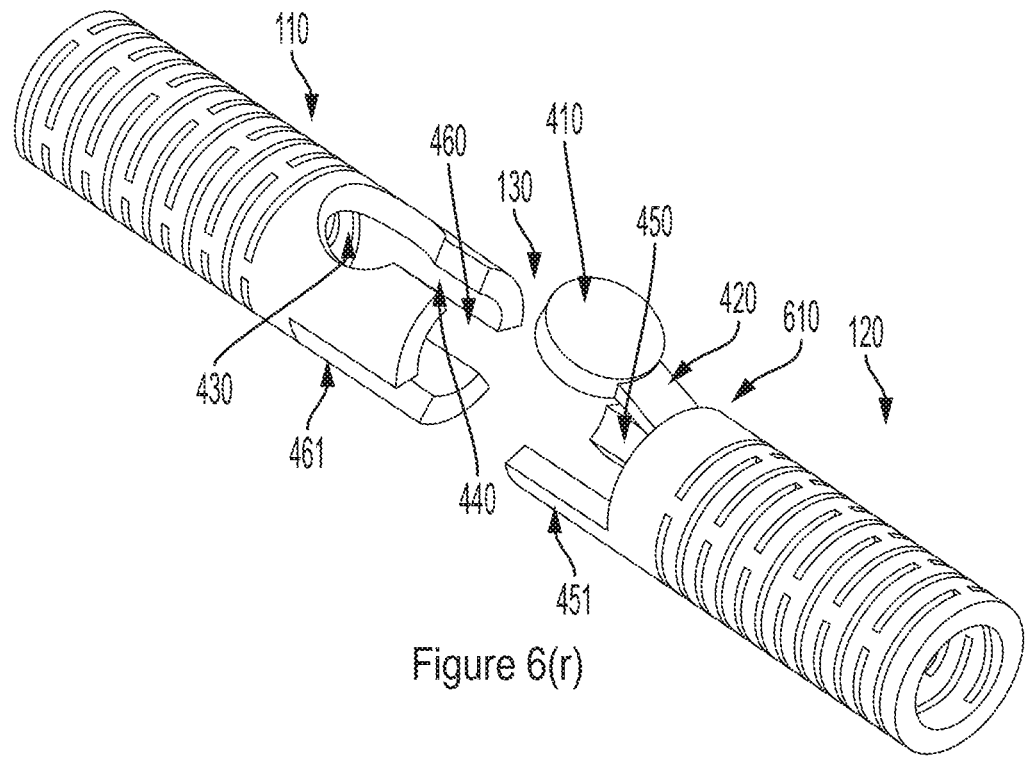
Figure 6S:
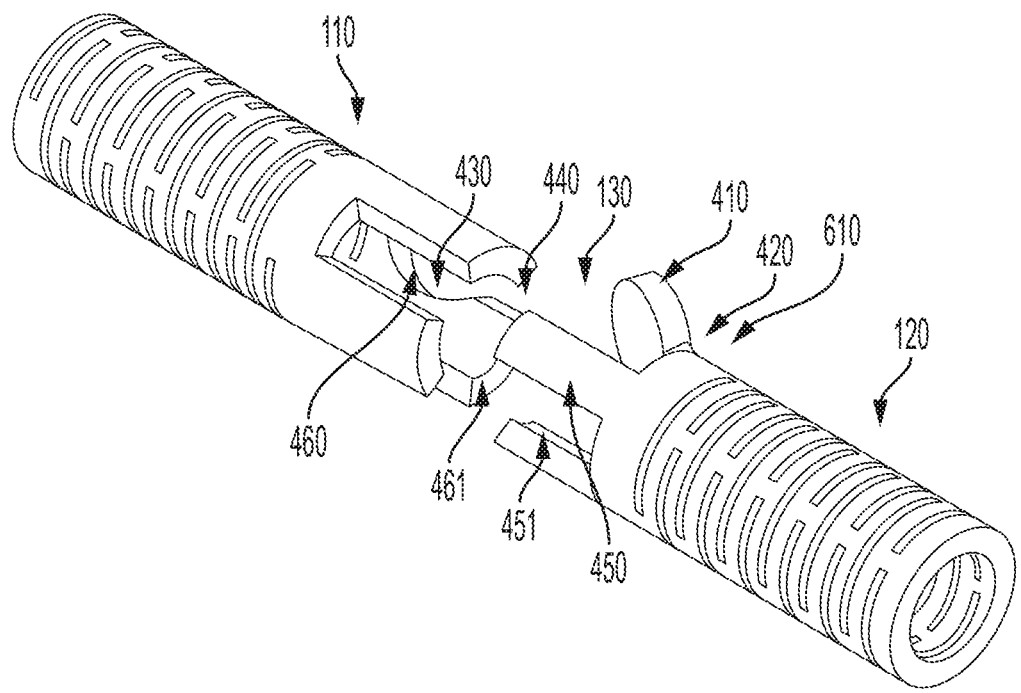

As noted above, the snap-fit connector 140, which can be positioned on either the distal or proximal tubular modules 110, 120 may be formed from a stem structure 420 (FIG. 6(c)) which can be attached at a cantilever joint 610 to one end of either the proximal or distal tubular module. The attachment forms a cantilever joint 610, which is elastically deformable, around which the stem structure 420 and locking structure 410 can bend at an angle θ ranging from of about 0° to about 90° with respect to a line parallel to the longitudinal axis 620 of the first or second tubular module, as further illustrated in FIG. 6(l). FIGS. 6(l)-(o) show flattened views (where the tubular module has been cut, unrolled and laid flat) of the snap-fit connector 410 of cantilever joint 610 in a raised position. FIG. 6(l) is a side or sagittal view of the raised cantilever joint. FIG. 6(m) shows the joint from the perspective of the external surface of the tubular module. FIG. 6(n) shows the join from a top external view, while FIG. 6(o) shows the joint from the perspective of the internal surface of the tubular module. FIGS. 6(p)-(s) show perspective views of the cantilever joint 610 with the snap-fit connector 140 in a raised position.

In addition to the snap-fit connectors, 140, at least one stabilizing element comprises a tongue element e.g., 450 in one of the tubular modules and a groove element e.g., 460 in the connecting module. The stabilizing element 450 may be positioned laterally to the snap connector around the circumference of an end of the proximal or distal tubular module, 110, 120 (a second stabilizing including tongue element 451 and groove element 461 are also shown in some of the figures (e.g., FIG. 6(s)). The stabilizing elements may assume a variety of different shapes, including, but not limited to, rectangular, trapezoidal, square, circular or triangular. Functionally, the role of the stabilizing elements 450 is illustrated in FIGS. 6(d)-(j). When the snap-fit connectors and acceptor 140, 150 are joined together, the stabilizing elements shapes function to prevent the proximal and distal tubular modules 110, 120 from rotating circumferentially at the joint 130 where the tubular modules have been connected. There may be one stabilizing elements (FIG. 6(e)), or alternatively there may be two or more stabilizing elements (FIG. 6(j)), e.g., 3, 4, 5, 6, 7, 8, 9, 10 . . . up to n stabilizing elements. The stabilizing elements allow for the transmission of force (torque) along the longitudinal length of the catheter.

The shape of the snap-fit connectors which are used to secure the two tubular modules together may vary. For example, in one embodiment, the snap-fit connector 150 of the proximal tubular module 110 has an acceptor in the form of an oval 430 with a stem structure 440, while the snap-fit connector 140 has complementary shape in the form of an oval 410 and stem structure 420 which fits directly into the snap-fit acceptor 150. This joining is illustrated in FIGS. 6(d)-6(j) where the tubular modules 110, 120 are connected together, and in 6(a)-6(b) where the two tubular modules are shown in an exploded view or separated from each other. FIGS. 6(d)-(j) illustrate the snap-fit joint from several different views. In FIGS. 6(d)-(j), stabilizing elements 450 and the snap connector 140 are positioned laterally with respect to each other around the distal tubular member.

Other shapes for the snap-fit connectors are encompassed herein, including semi-circular, oblong, triangular, trapezoidal or irregular, either individually or in combination with other shapes. In these designs, the maximum width of the locking structure 410, measured between opposite sides, is greater than the width of the stem structure 420. This configuration secures the snap-fit connector 140 within the snap-fit acceptor, preventing them from pulling apart from each other without first releasing the snap-fit connector.

Figure 6T:
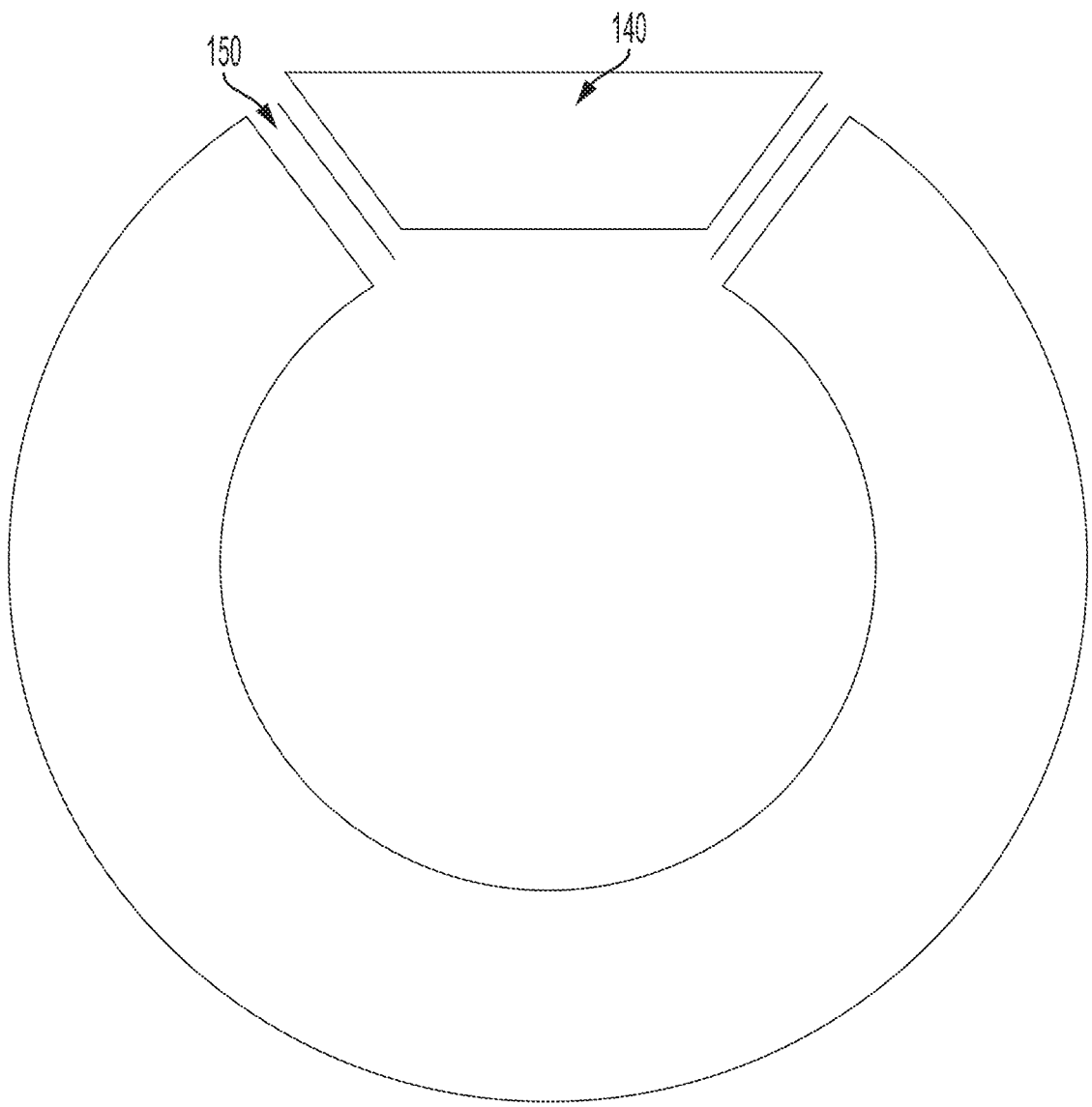
Figure 7A:
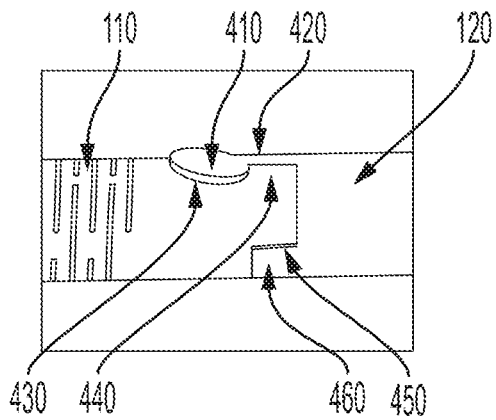
FIG. 7(a) shows a photomicrograph of a side view of a snap-fit joint that couples two tubular modules according to an embodiment of the present invention.
Figure 7D:
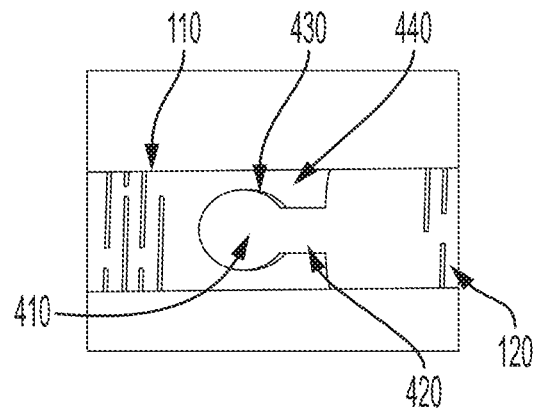
FIG. 7(d) shows a photomicrograph of a top view of the snap-fit joint of FIGS. 7(a) to 7(c).
Figure 7B:
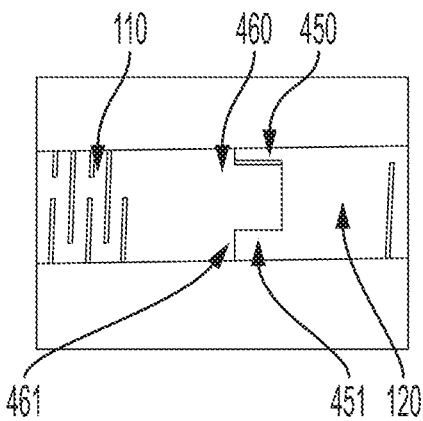
FIG. 7(b) shows a photomicrograph of the snap-fit joint of FIG. 7(a) as rotated approximately 60° about the longitudinal axis with respect to the photograph shown in FIG. 7(a).
Figure 7E:
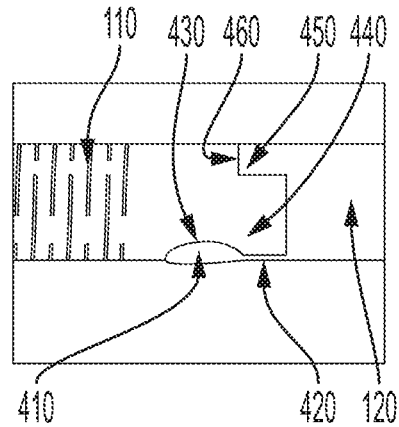
FIG. 7(e) shows a photomicrograph of the snap-fit joint of FIGS. 7(a) to 7(d) as rotated approximately 60° about the longitudinal axis with respect to the photograph shown in FIG. 7(d).
Figure 7C:
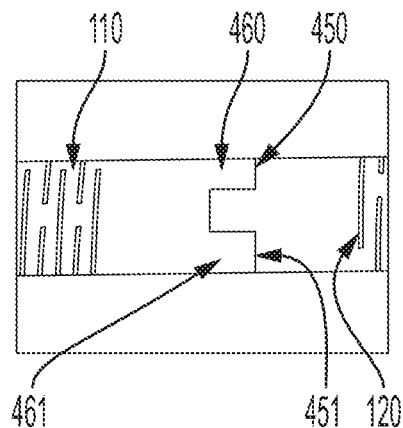
FIG. 7(c) shows a photomicrograph of the snap-fit joint of FIGS. 7(a) and 7(b) as rotated approximately 60° about the longitudinal axis with respect to the photograph shown in FIG. 7(b).
Figure 7F:
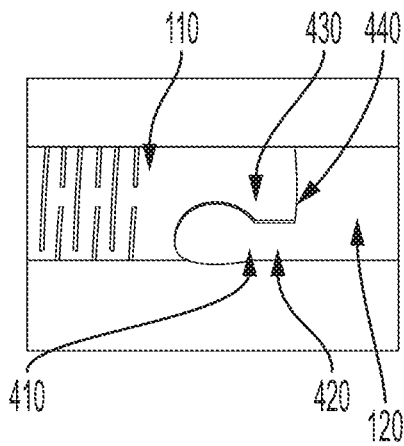
FIG. 7(f) shows a photomicrograph of the snap-fit joint of FIGS. 7(a) to 7(d) as rotated approximately 30° about the longitudinal axis with respect to the photograph shown in FIG. 7(d).
Figure 8A:
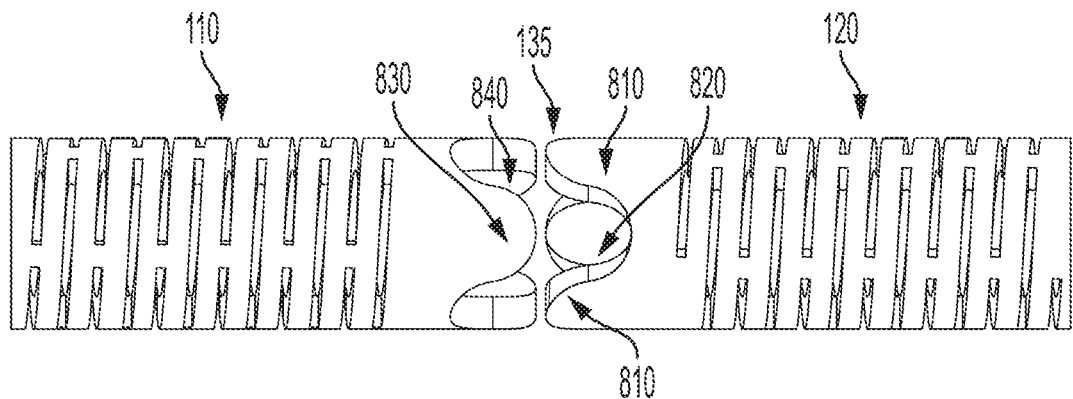
FIG. 8(a) shows one view of another embodiment of a joint (slightly separated) for coupling two tubular modules according to the present invention which employs interlocking sinusoidal shapes.
Figure 8B:
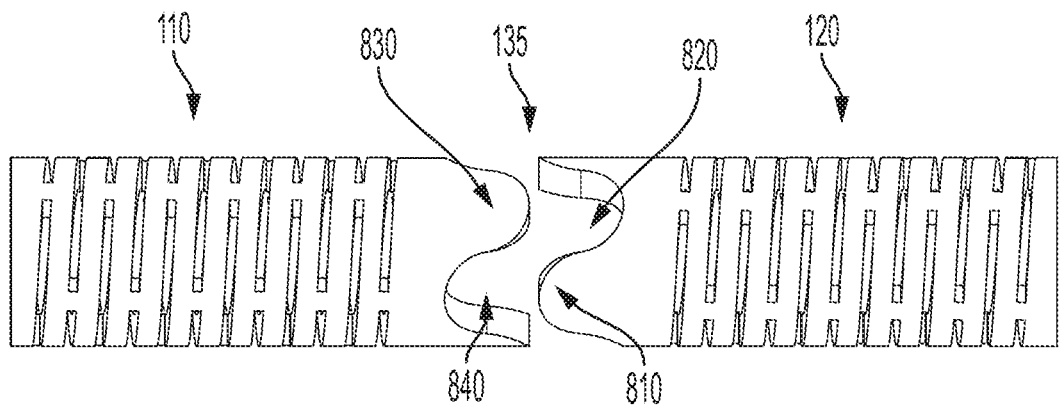
FIG. 8(b) shows another view of the joint shown in FIG. 8(a) as rotated approximately 30° about the longitudinal axis.
Figure 8C:
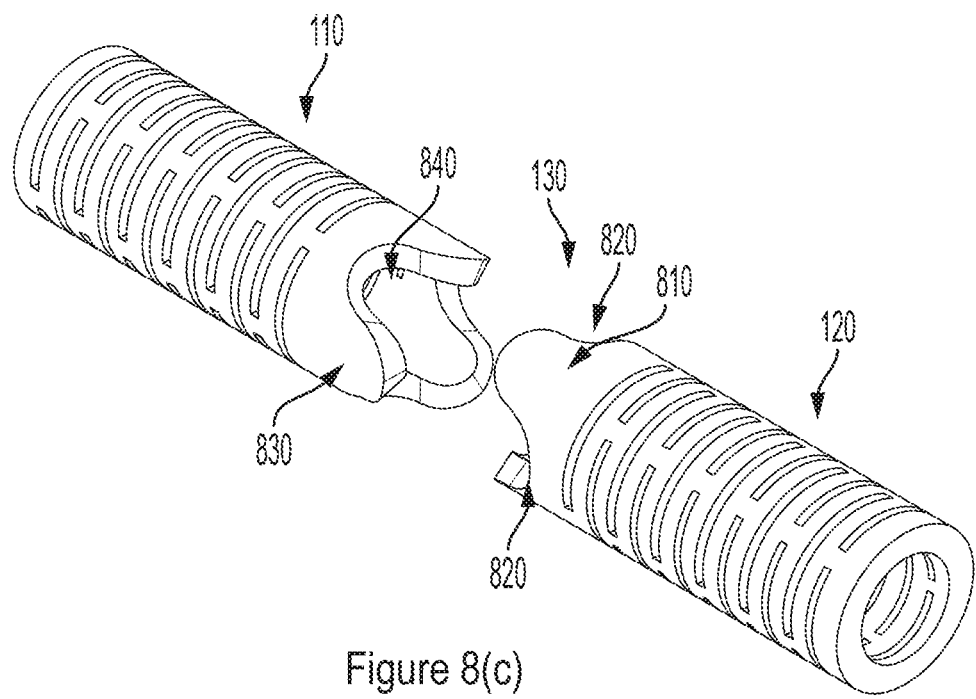
FIG. 8(c) shows a perspective view of the joint (separated) of FIGS. 8(a) and 8(b).
Figure 8D:
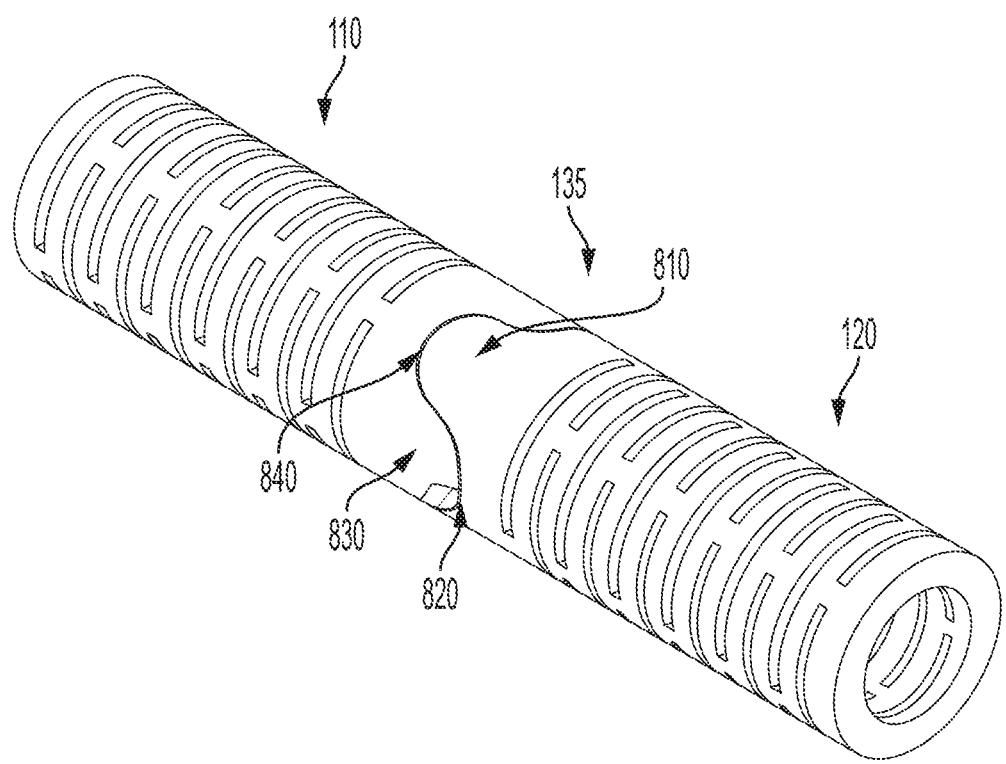
FIG. 8(d) shows a perspective view of the joint shown in FIGS. 8(a) to 8(c) in a coupled state.
Figure 8E:
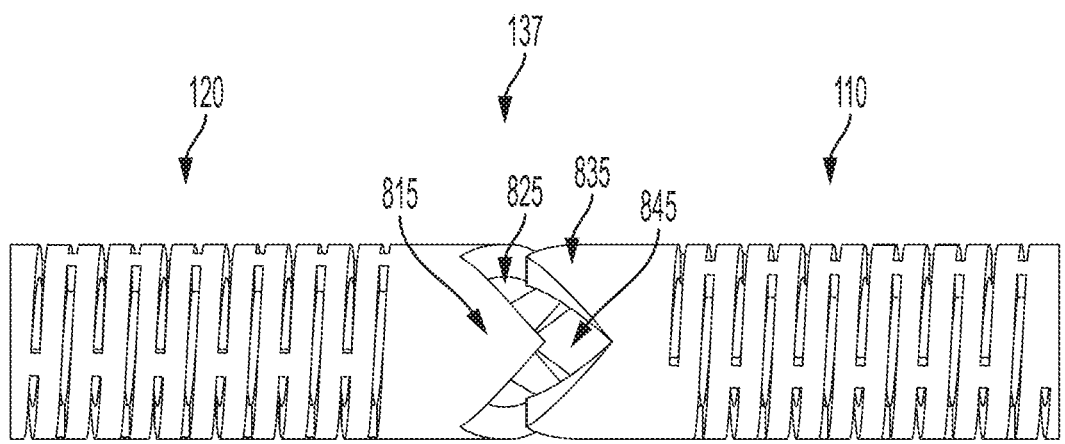
FIG. 8(e) shows a side view of another embodiment of joint (slightly separated) for coupling two tubular modules according to the present invention which using interlocking triangular shapes.
Figure 8F:
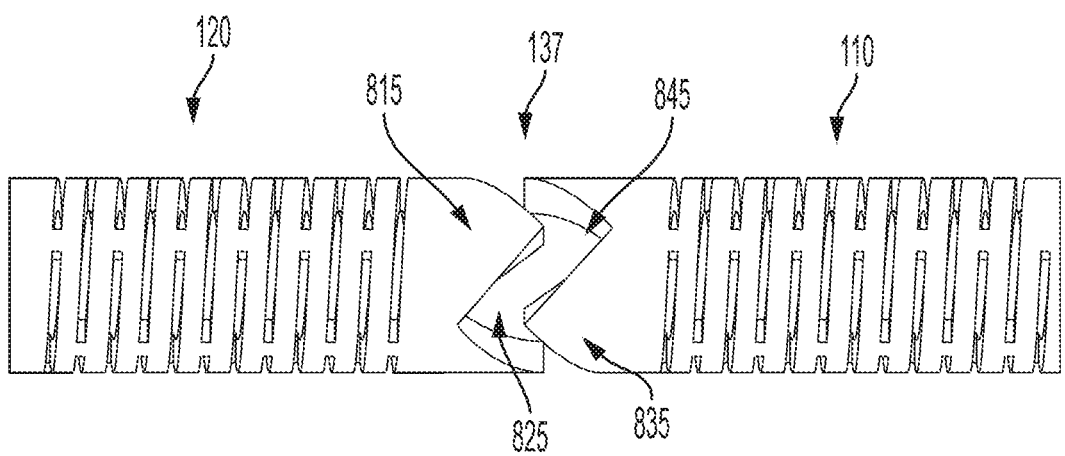
FIG. 8(f) shows another view of the joint shown in FIG. 8(e) as rotated approximately 30° about the longitudinal axis.
Figure 8G:
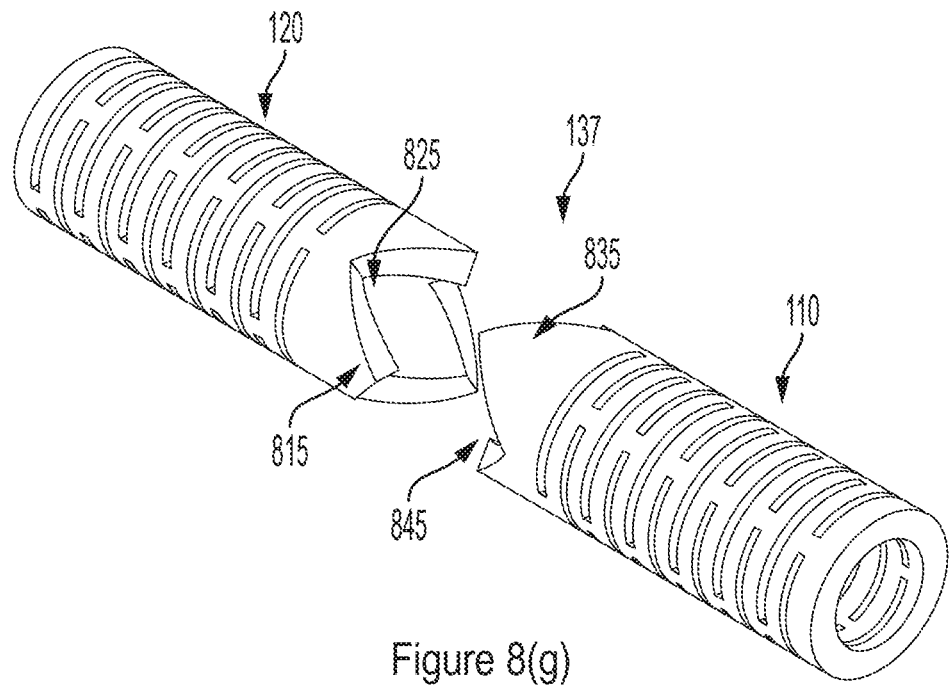
FIG. 8(g) shows a perspective view of the joint (separated) of FIGS. 8(e) and 8(f).
Figure 8H:
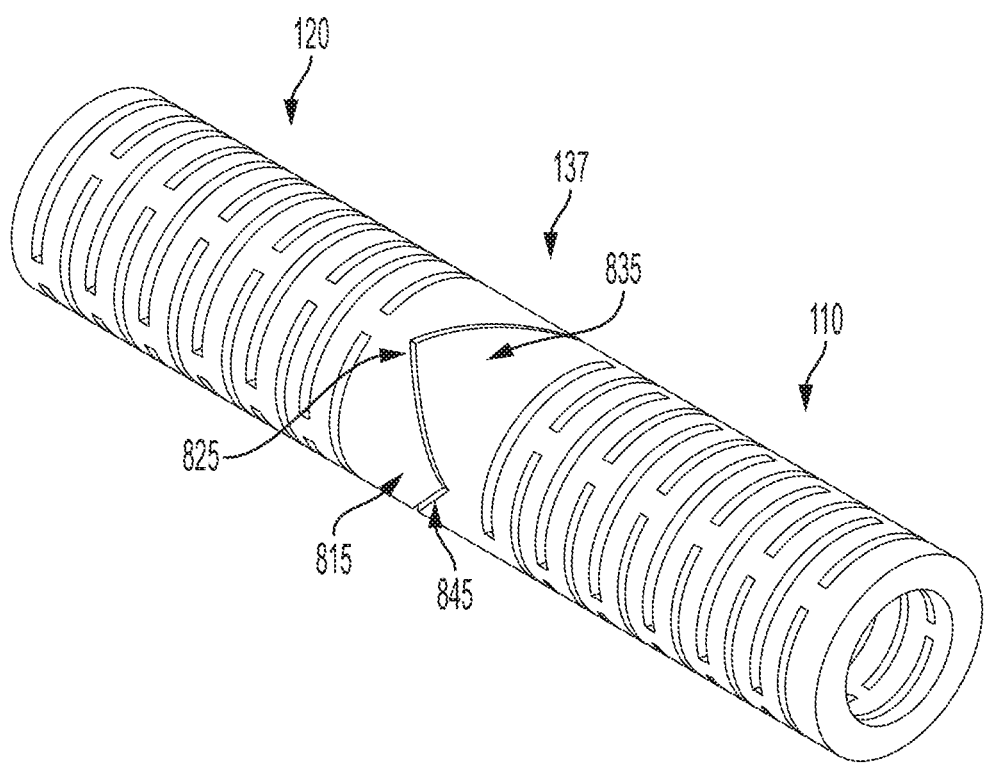
FIG. 8(h) shows a perspective view of the joint shown in FIGS. 8(e) to 8(g) in a coupled state.

The edges of the snap-fit connector 140 of the distal tubular module 120 and the edges of the snap-fit acceptor 150 of the proximal tubular module 110 may be beveled to ensure that the snap-fit connector and snap-fit acceptor are securely connected and will not separate or dislodge after insertion into the patient as illustrated in FIG. 6(t). The angle θ of the bevel may range from about 0° to about 90° with respect to a line formed along the longitudinal axis of the proximal and distal tubular modules. The angle θ can range from about 5° to about 90°, about 20° to about 70°, or 40° to about 60°. The snap-fit connector and snap-fit acceptor can also be joined by gluing, soldering, laser welding, welding or enclosing within a ring or securing a jacket (tubular) over the joint. These modifications prevent the snap-fit from lifting out-of-plane.

As illustrated in FIGS. 7(a)-(f), which depict photomicrographs of the joint between snap-fit connectors and snap-fit acceptors according to embodiments of the present invention, the joint between the snap-fit connector 140 and snap-fit acceptor 150 may be flush, i.e., the surface of the snap-fit connector does not protrude above the outer surface (outer diameter) of the snap-fit acceptor and is level with the outer surface of the tubular modules.

FIGS. 8(a)-(h) illustrate other embodiments of the types of joints between the proximal tubular module 110 and the distal tubular module 120. In these embodiments, the proximal and distal tubular modules 110, 120 have interlocking shapes including protruding sections 810, 830 and receiving sections 820, 840 at the joint 135 which interlock with each other. In the embodiment shown in FIGS. 8(a)-(d), the protruding section 810, 830 and receiving sections 820, 840 take the form of a wave, sinusoid, meandering or curvilinear elements. In another embodiment, FIGS. 8(e)-(h), interlocking shape 137 comprises protruding sections 815, 835 and receiving sections 825, 845 in the form of a triangular or zig-zag pattern. The interlocking shapes of the protruding and receiving sections used can all be the same, or there may be more than one type of protruding and receiving section on either the proximal and/or distal tubular modules.

In general, embodiments can include one or more, 1, 2, 3, 4, 5, 6, 7, 8, 9, 10 . . . n, protruding sections and receiving sections. For example, in the embodiments illustrated in FIGS. 8(a)-(h), there are three protruding sections and corresponding receiving sections. Functionally, the protruding sections e.g., 810, 830 and receiving sections e.g., 820, 840, prevent the proximal and distal tubular modules, 110, 120 from rotating circumferentially at the joints where the tubular modules have been connected. The interlocking shape joints can be covered with a tubular jacket to help secure the joint.

Figure 9A:
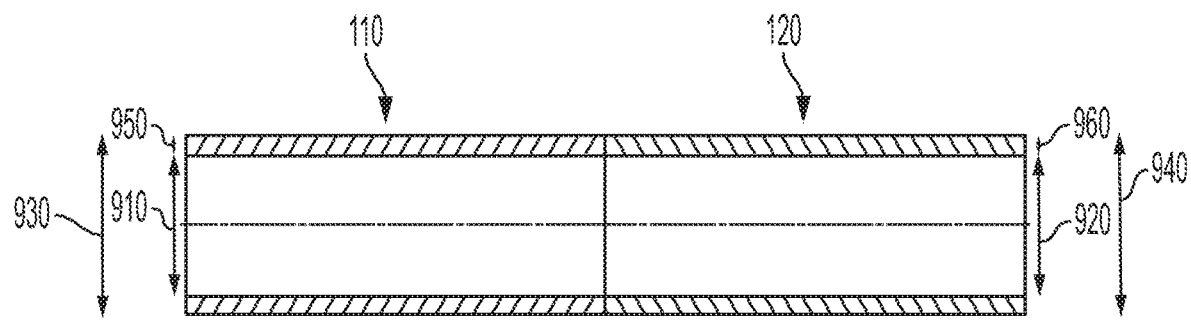
FIG. 9(a) shows a cross-sectional view showing wall thickness of two connecting tubular modules according to the present invention in the plane of the longitudinal axis according to an embodiment of the present invention.
Figure 9B:
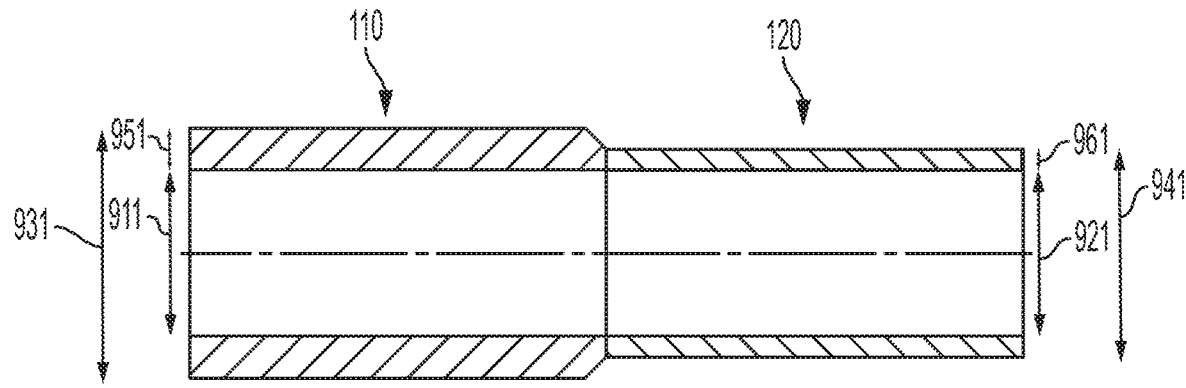
FIG. 9(b) shows a cross-sectional view of another embodiment of wall thickness of two connecting tubular modules according to an embodiment of the present invention.
Figure 9C:
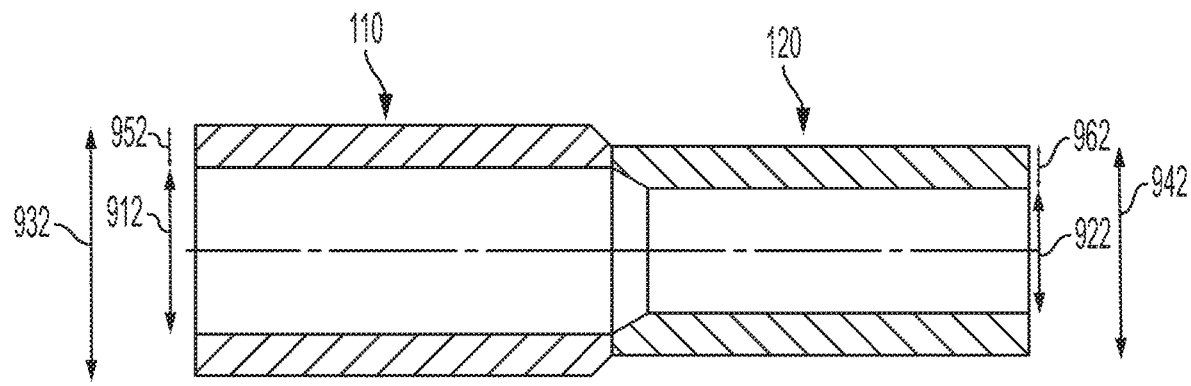
FIG. 9(c) shows a cross-sectional view of yet another embodiment of wall thickness of two connecting tubular modules according to an embodiment of the present invention.

As illustrated in cross-sectional views in FIGS. 9(a)-(c), the proximal and distal tubular modules 110, 120 may have the same or different inner or outer diameters. The outer diameter of the proximal tubular module 110 or the distal tubular module 120 can range from about 0.5 mm to about 1 mm. The inner diameter of the proximal tubular module 110 or the distal tubular module 120 can range from about 0.10 mm to about 3.5 mm.

As shown in FIG. 9(a), the inner diameter 910 of proximal tubular module 110 and the inner diameter 920 of distal tubular module 120 may be the same or approximately the same. In addition, the outer diameter 930 of the proximal tubular module 110 and the outer diameter 940 of the distal tubular module 120 may be the same or approximately the same.

Figure 10A:
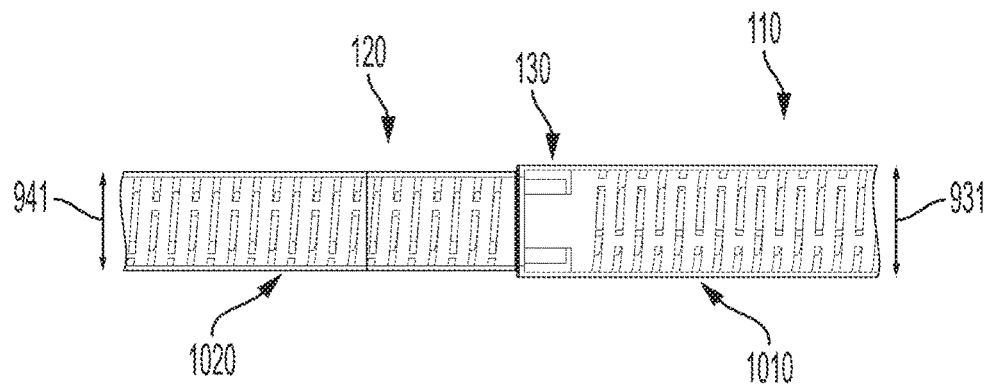
FIG. 10(a) shows a side view of an embodiment in which the outer diameter of one of the tubular modules (proximal) is larger than the outer diameter of a tubular module (distal) to which it is connected.
Figure 10B:
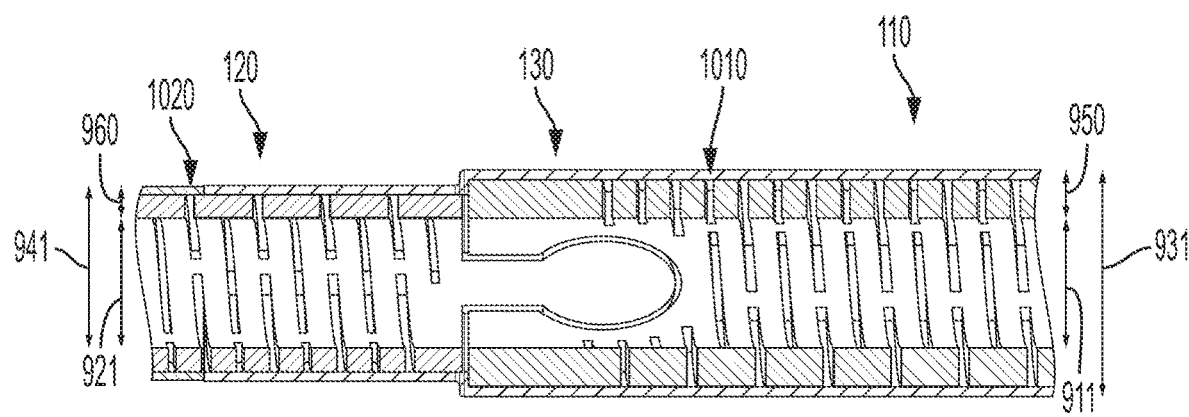
FIG. 10(b) shows a longitudinal cross-sectional view of the embodiment shown in FIG. 10(a).

Alternatively, as shown in FIG. 9(b), the proximal tubular module 110 and the distal tubular module 120 may have the same inner diameter 911, 921, but have different respective outer diameters 931, 941 (FIG. 9(b)). In this particular embodiment, the proximal tubular module 110 has a larger outer diameter 931 than the outer diameter 941 of the distal tubular module 120. This is further illustrated in the embodiments shown in FIGS. 10(a) and 10(b). In this embodiment, at the joint between the proximal tubular member 110 and the distal tubular member 120, the proximal tubular member 110 and the distal tubular member 120 form a 90° angle with respect to each other due to the differences in their outer diameters 931, 941. FIG. 10(a) illustrates the difference in outer diameter 931 of the proximal tubular module 110 as compared to outer diameter 941 of the distal tubular module 120. FIG. 10(b) shows a cross-sectional view of FIG. 10(a). In the embodiment shown here, the inner diameter of both the proximal tubule 911 and distal tubular module 921 are the same.

In yet another embodiment, the proximal tubular module 110 can have both a larger inner diameter 912 and outer diameter 932 than the inner and outer diameters 922, 942, respectively, of the distal tubular module 120 (FIG. 9(c)). This distinction is further illustrated in FIGS. 10(c) and 10(d), which show partial and extended cross-sectional views of the embodiment shown in FIG. 9(c). In this embodiment, at the joint 130 between the proximal tubular member 110 and the distal tubular member 120, the inner diameter 922 and the outer diameter 942 of the distal tubular module 120 at the joint 130 are initially the same as the inner diameter 912 and outer diameter 932 of the proximal tubular module 110. At the joint, the inner diameter 922 and outer diameter 942 of the distal tubular module 120 decreases in size until the inner diameter 922 and the outer diameter 942 of the distal tubular module 120 are smaller than the inner diameter 912 and outer diameter 932 of the proximal tubular module 110. The decreases in size of the inner diameter 922 and outer diameter 942 may be linear or non-linear.

The proximal tubular module 110 or the distal tubular module 120 can have a varying diameter across its length, e.g., a tapered configuration. The tapering can be in any direction or may only be present along a portion of the tubular module.

Figure 10C:
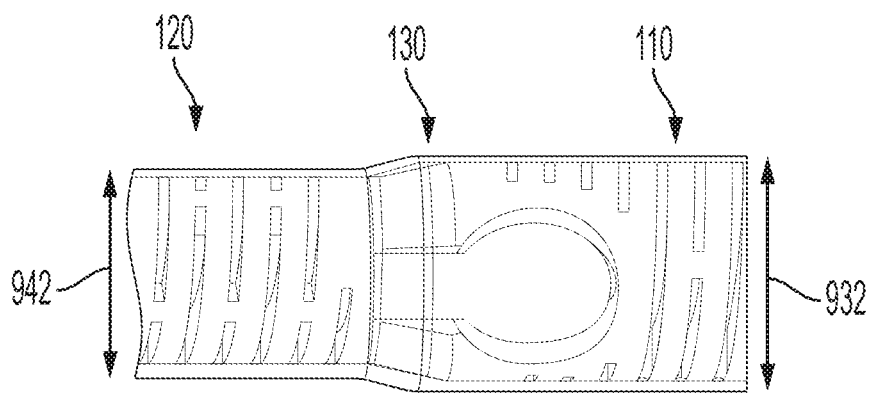
FIG. 10(c) shows a side view of the embodiment of the tubular modules shown in FIG. 9(c).
Figure 10D:
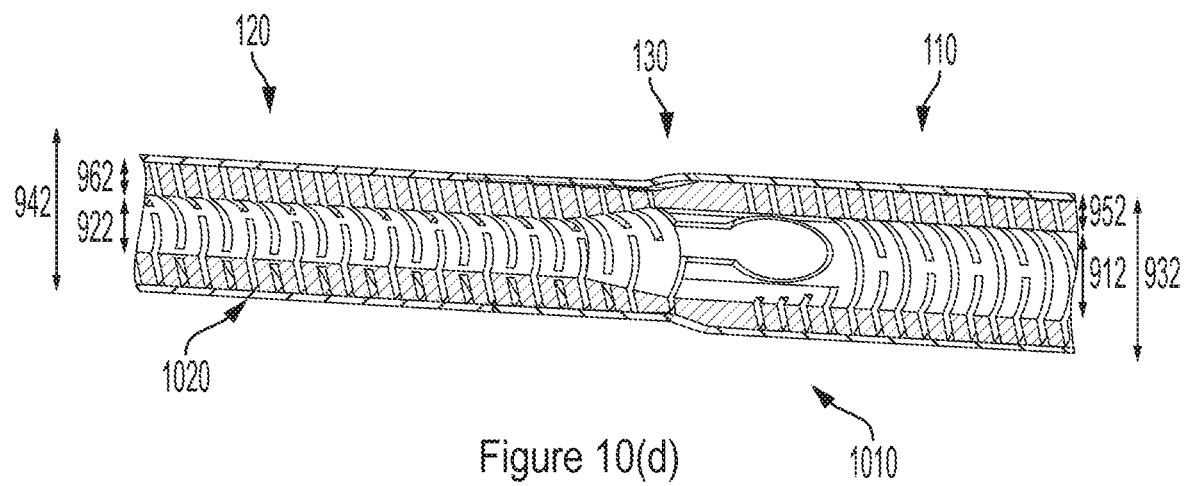
FIG. 10(d) shows a perspective longitudinal cross-sectional view of the embodiment of FIGS. 9(c) and 10(c).

The wall thickness of the proximal tubular module 110 and the distal tubular module 120 may vary, for example to increase flexibility toward the distal tip. In the embodiment shown in FIG. 9(a), the wall thickness 950 of the proximal tubular module 110 may be the same as the wall thickness 960 of the distal tubular module 120. In the embodiment shown in FIGS. 9(b) and 10(b), the wall thickness 951 of the proximal tubular module 110 is greater than the wall thickness 961 of the distal tubular module 120. However, in this embodiment the inner diameters 911, 921 of the proximal and distal tubular modules 110, 120 remain the same while the outer diameters 931, 941 of the proximal and distal tubular modules 110, 120, are different. In FIGS. 9(c), 10(c) and 10(d) the wall thickness of the proximal tubular module 952 tapers at the joint with the distal tubular module. Similarly, the wall thickness 962 of the distal module tapers at the joint with the proximal tubular module. The thickness of the wall can taper. For example, the wall thicknesses 952, 962 are larger away from the joint 130 and can be the same or different with respect to each other. Any changes in inner diameter or outer diameter from one tubular module will incorporate a transition from one tubular module to the next which can be tapered.

Depending on the material as well as the structural requirements in terms of flexibility, the wall thickness of a tubular module at any point can vary, e.g., from about 0.05 mm to 2 mm, e.g., 0.05 mm to about 1 mm, about 0.1 mm, 0.2 mm, 0.3 mm, 0.4 mm, 0.5 mm, 0.6 mm, 0.7 mm, 0.8 mm, 0.9 mm, 1.0 mm, etc. The inner diameter of a tubular module can vary, e.g., from about 0.1 mm to about 2 mm, or from about 0.25 mm to about 1 mm, e.g., about 0.2 mm, about 0.3 mm, about 0.4 mm, about 0.5 mm, about 0.6 mm, about 0.7 mm, about 0.8 mm, about 0.9 mm, about 1 mm, about 2 mm, about 2.5 mm, about 3 mm thickness. The outer diameter a tubular module can also vary, e.g., from about 0.2 mm to about 3 mm, e.g., including about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.5 mm, about 3 mm thickness. The wall thickness of the tubular module wall, the inner diameter and the outer diameter can each be constant throughout the length of the tubular module, or vary along the length of the tubular module.

Figure 10E:
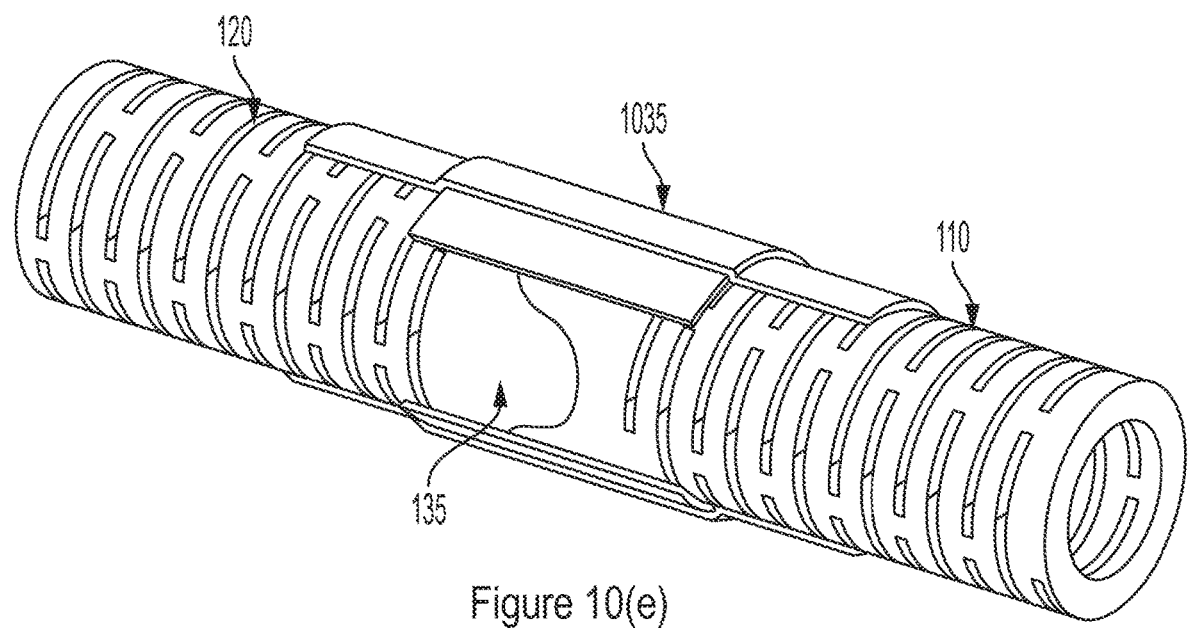
FIGS. 10(e) and 10(f) show that the joint may also be covered with a crimped metal that firmly covers and bonds the connected tubular modules.
Figure 10F:
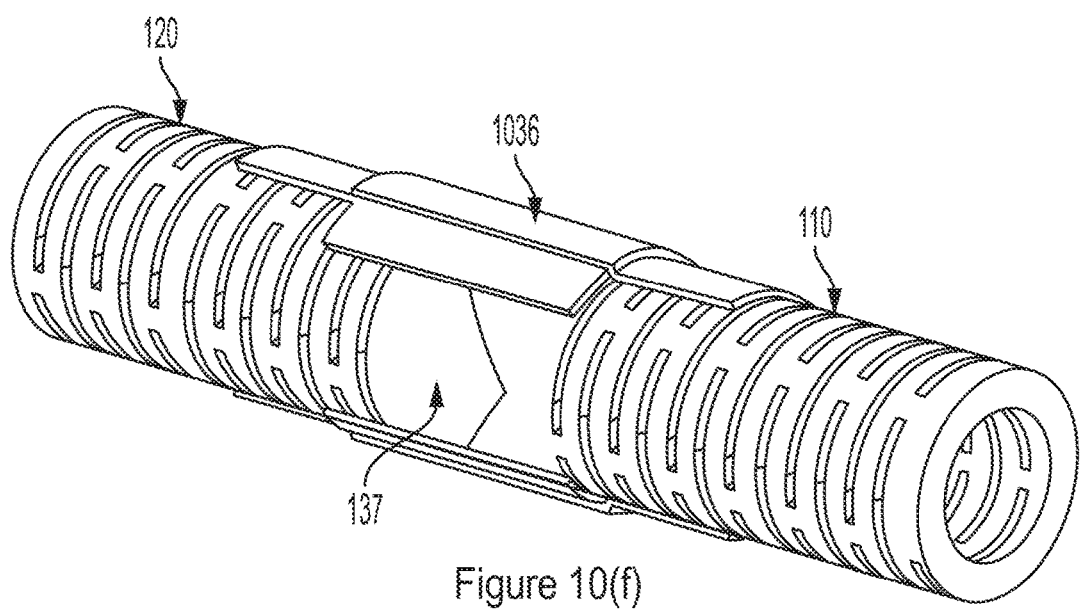
Figure 11A:
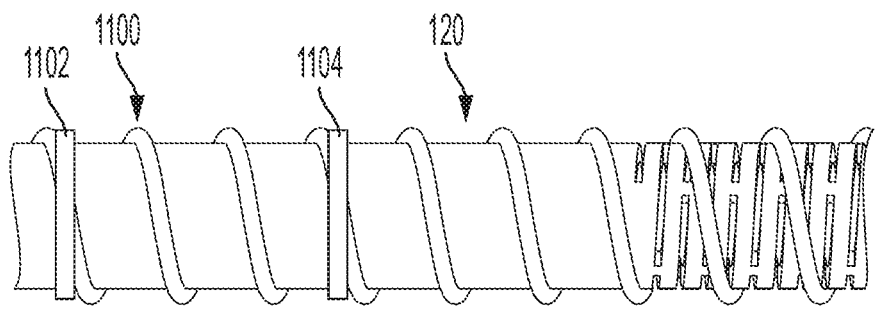
FIG. 11(a) shows a side view in which a filament is wrapped around a tubular module according to an embodiment of the present invention.
Figure 11B:
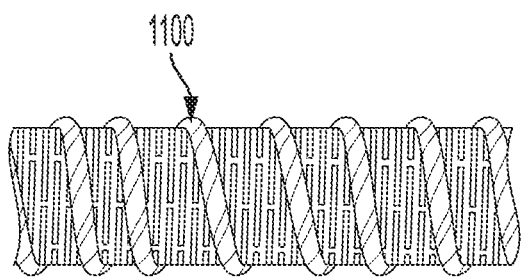
FIG. 11(b) shows a photograph of a side view of a tubular module having a wrapped filament according to an embodiment of the present invention.
Figure 11C:
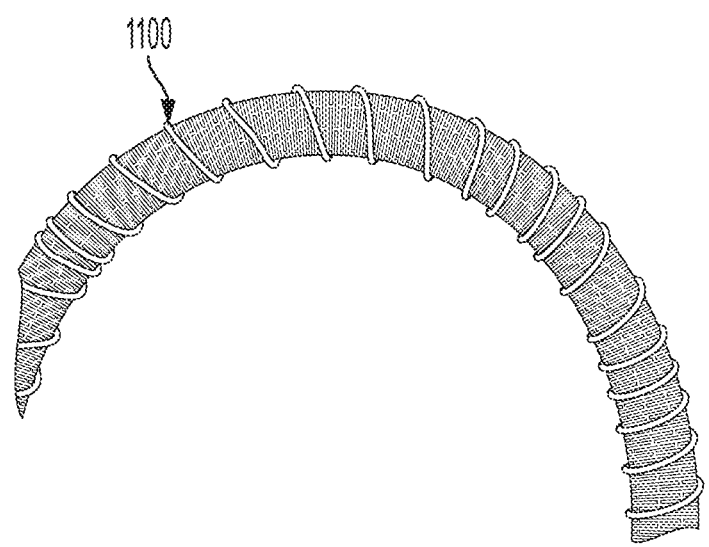
FIG. 11(c) shows a photograph of a curved tubular module having a wrapped filament according to an embodiment of the present invention.
Figure 11D:
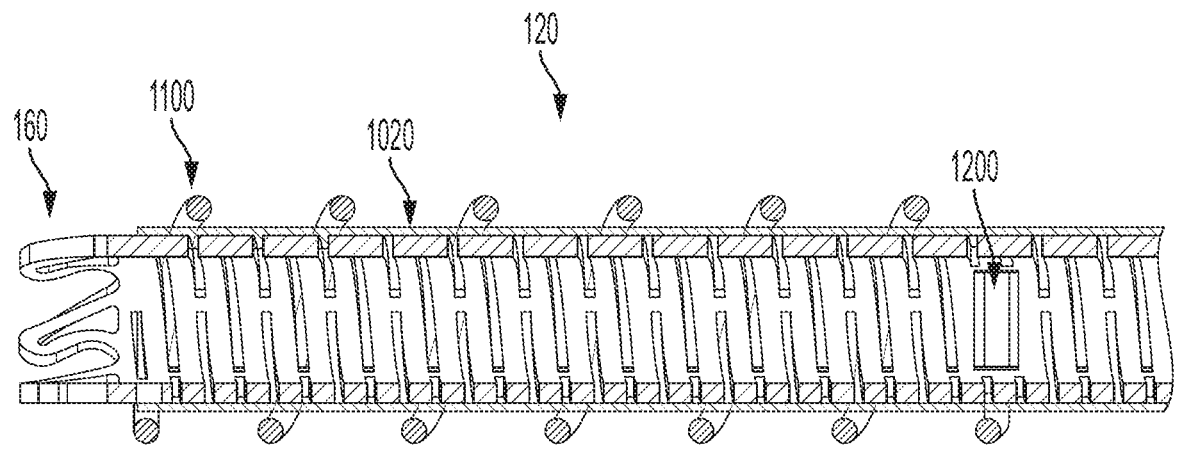
FIG. 11(d) shows a cross-sectional view of the embodiment shown in FIG. 11(a).
Figure 11E:
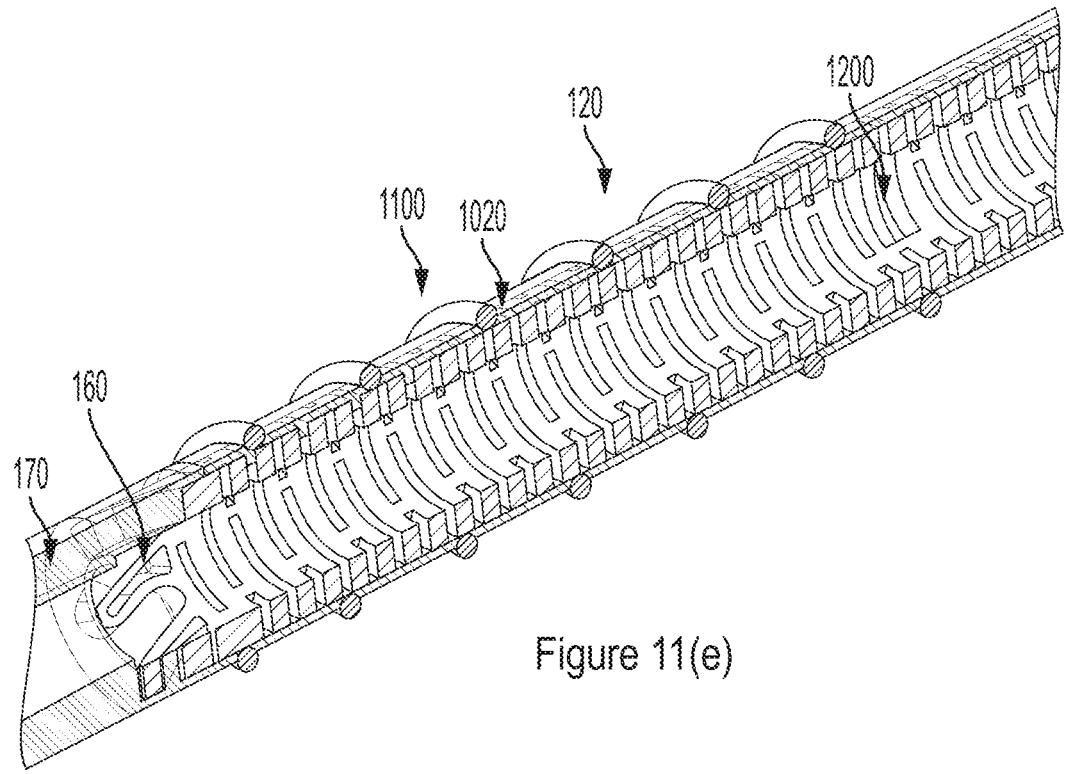
FIG. 11(e) shows a perspective cross-sectional view of the embodiment of FIGS. 11(a) and 11(d).
Figure 12A:
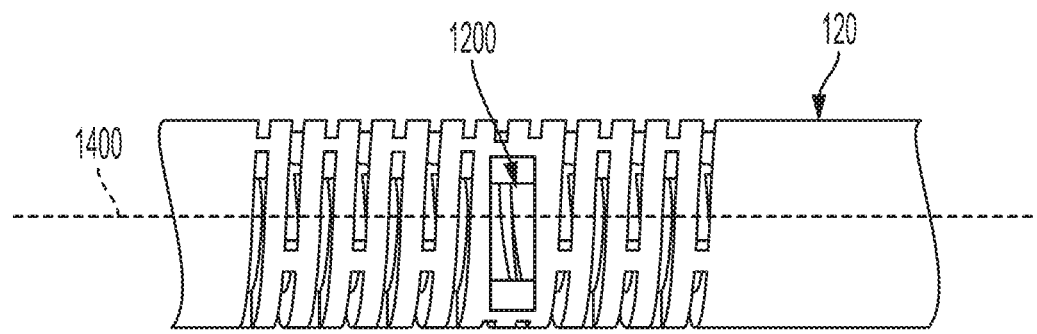
FIG. 12(a) shows a side view of a tubular module including a cut opening according to an embodiment of the present invention.
Figure 12B:
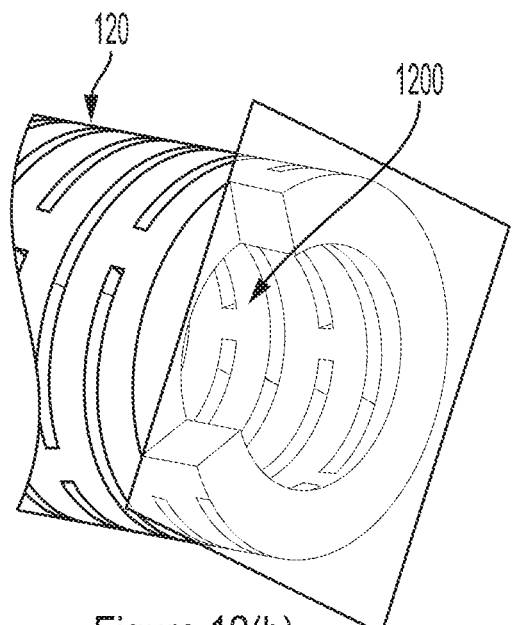
FIG. 12(b) shows a perspective cross-sectional view of the embodiment shown in 12(a) in the perpendicular plan across the cut opening.
Figure 12C:
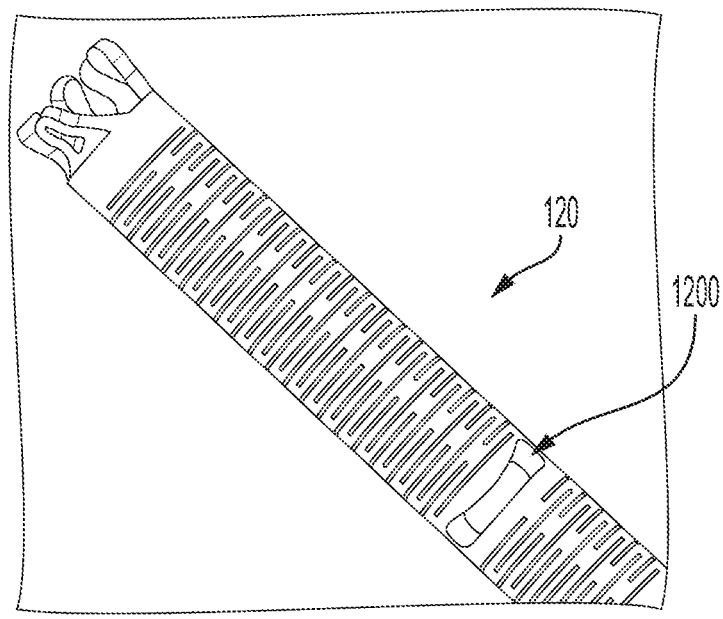
FIG. 12(c) shows a photograph of a tubular module having a cut opening according to an embodiment of the present invention.
Figure 12D:
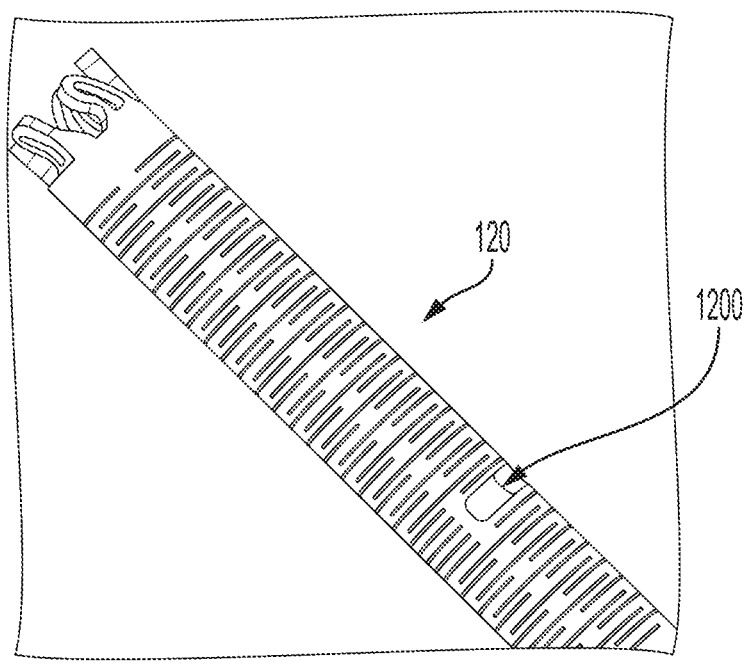
FIG. 12(d) shows a photograph of the tubular module shown in FIG. 12(c) rotated to depict the edge of the cut opening.

The joint between tubular modules may be coated or covered with a jacket or a sleeve such as a polymer. FIGS. 10(a)-10(d) depict an embodiment in which the coating comprises two separate sections, a coating 1010 that covers the distal end of the proximal tubular module 110 as well as the joint 130, and a second coating 1020 that covers or coats a distal portion of the distal tubular module 120; the coatings 1010, 1020, may be the same or different. In other embodiments a single coating (i.e., either a jacket or spray coating) can be used. This jacket or sleeve further bonds the elements of the joint together, preventing the proximal tubular module 110 and distal tubular module 120 from disconnecting from each other. The entire catheter 100 or only a portion of the catheter 100, e.g. the proximal or distal tubular modules, can be coated. The coating or jacket can provide a conduit for fluid along the length of the catheter. The coating may also be limited to cover only the joint 130 where two tubular modules are connected together. Alternatively, the joint can be covered with a ring to secure the joint 130. As depicted schematically in FIGS. 10(e) and 10(f) the joint may also be covered with a crimped metal that firmly covers and bonds the connected tubular modules. FIG. 10(e) shows a joint 135 covered with crimped metal 1035 and FIG. 10(f) shows a joint 137 covered with crimped metal 1036

In addition, the inner walls, i.e., lumen, of the proximal and distal tubular modules can be coated with an inner lining that both protects the tubular modules and facilitates transport of additional tools devices such as guidewires and balloons through the tubes of the catheter to distal locations. The inner lining can extend along a portion of the proximal or distal tubular modules or can extend throughout the entire length of the tubular modules.

The jacket as well as the inner lining can be made from a polymer, e.g., by enclosing the tube wall with a co-extruded polymeric tubular structure of single of multiple layers and heat shrinking the tubular structure, or coating the tube wall via a dip coating process. The polymer jacket material can be nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone). Further, the distal tube portion 120 (or the entire length of catheter 100) may be coated with a hydrophilic polymer coating to enhance lubricity and trackability. Hydrophilic polymer coatings can include, but are not limited to, polyelectrolyte and/or a non-ionic hydrophilic polymer, where the polyelectrolyte polymer can include poly(acrylamide-co-acrylic acid) salts, a poly(methacrylamide-co-acrylic acid) salts, a poly(acrylamide-co-methacrylic acid) salts, etc., and the non-ionic hydrophilic polymer may be poly(lactams), for example polyvinylpyrollidone (PVP), polyurethanes, homo- and copolymers of acrylic and methacrylic acid, polyvinyl alcohol, polyvinylethers, snapic anhydride based copolymers, polyesters, hydroxypropylcellulose, heparin, dextran, polypeptides, etc. See e.g., U.S. Pat. Nos. 6,458,867 and 8,871, 869. The coating can be applied by a dip coating process or by spraying the coating onto the tube outer and inner surfaces.

In the process of spray coating, a coating formulation is applied to the surface of the device using a nozzle apparatus. This apparatus has a chamber for containing the coating formulation and an opening in fluid connection with the chamber through which the coating formulation can be dispensed and deposited on the surface. To apply the coating formulation to the surface of the tubular modules of the catheter, the formulation is placed into the chamber of the nozzle apparatus and charged using a high voltage using a conductor. Once the coating formulation in the chamber is charged, it carries the same charge as the conductor. As a result, the formulation and conductor repel each other. This repulsive force discharges the coating formulation through the opening of the nozzle to create streams of droplets. An additional gas source can be used for atomizing the coating formulation.

One or both of the tubular modules 110, 120 can further include a filament 1100. FIG. 11(*a*) through 11(*e*), depict a filament 1100 wrapped around the distal tubular module 120. In FIGS. 11(*a*)-11(*c*), the filament 1100 is wrapped around the distal tubular module 120 in a spiral manner. FIGS. 11(*a*) and 11(*b*) show the catheter, i.e., the tubular modules, in a straight configuration while FIG. 11(*c*) shows the catheter, the tubular modules, in a curved configuration. In general, the filament 1100 is disposed on the outer surface of the distal tubular module 120 and encircles all or part of the distal tubular module 120. The filament 1100 proceeds in a spiral fashion around the distal tubular module 120 and forms a spiral structure on the outer surface of the tubular module. In certain embodiments, the spiral filament can be wrapped around the proximal tubular module. The filament may be wrapped in a clockwise or counter-clockwise manner around the tubular modules.

The filament 1100 can be adhered to or attached to the tubular modules in variety of different ways. In one embodiment, the filament 1100 is securely coupled to the tubular module fitting one or more bands or cover around it and the tubular module. Other implementations can include wedging, hooking, affixing, bonding or gluing the filament into or onto the tubular module. FIG. 11(*a*) shows bands 1102, 1104 that securely fasten the filament 1100 to the distal tubular module 120. Additionally, in some embodiments, the jacket that covers one or more of the tubular modules also covers the filament 1100 as well. This cover firmly secures the filament in place with respect to the tubular module.

A lubricious coating or film may be added over the jacket to facilitate movement of the catheter through blood vessels. The lubricious coating can be composed of, for example, silicone or hydrogel polymers or the like, such as polymer networks of a vinyl polymer, polyalkylene glycols, alkoxypolyethylene glycols or an uncrosslinked hydrogel, e.g., Polyethylene oxide (PEO).

In other embodiments such as in FIGS. 11(*d*) and 11(*e*), the filament 1100 is threaded over the coating 1020 on one or more of the tubular modules. FIGS. 11(*d*) and 11(*e*) show a cross section view of the filament attached to the outer surface of the distal tubular module 120. The cross-section view of the filament 1100 may be circular, as illustrated in FIGS. 11(*d*) and (*e*). Alternatively, the cross-section of the filament 1100 may have different shapes, for example, square, rectangular, triangular, hexagon, semi-circular, or oblong. The filament 1100 may be used for screwing (or unscrewing) through small tapering diameter vessels or occlusive segments within the arterial wall, for example, such as de novo plaque area and restenotic segment of the target vessel. As the filament 1100 comes into contact with the vessel and/or occlusive segments, and torque is applied to the catheter, the filament facilitates forward motion of the catheter through intermediate vessels and plaque in order to reach the target vessel. For example, when the catheter system 100 is rotated, the filament 1100 can be used to facilitate drilling or boring through a calcified atheromatous plaque. The filament 1100 converts rotational motion into linear motion and torque into a linear force, thereby making it easier for the catheter to proceed through the blood vessels, especially in regions of comparative calcification. The filament 1100 can also be used as a securing mechanism, such as to secure the catheter to a specified location within the blood vessels, by creating a clamping force against the walls of the blood vessels. To remove the catheter, the catheter would have to be backed-out using the same screw-like motion but in the opposite direction in order to prevent stripping the walls of the blood vessel. Because of its rounded surface, a circular cross-section minimizes damage to the arterial walls. The pitch angle of the spiral thread may remain constant. Having the spiral thread segment adherent to the outside of the module allows the pitch angle to remain constant over the length of the spiral segment.

The filament can be the same material or a different material from the tubular modules 110, 120. Alternatively, in some embodiments, the filament 1100 can be made of a polymer.

Figure 14:
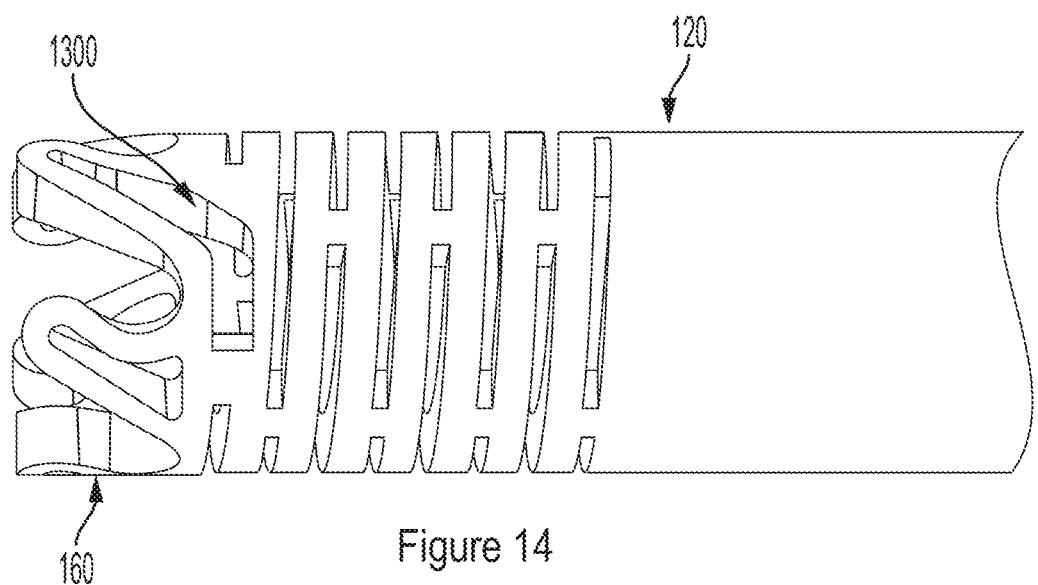
FIG. 14 shows a side view of the end of a distal tubular module having a second cut opening in an general L shaped and a crown.

The proximal tubular module 110 and the distal tubular module 120 can include at least one additional cut opening through the wall, as illustrated in FIGS. 12(*a*)-12(*d*) and FIG. 14. The cut openings may be on the same or different tubular modules.

Figure 13:
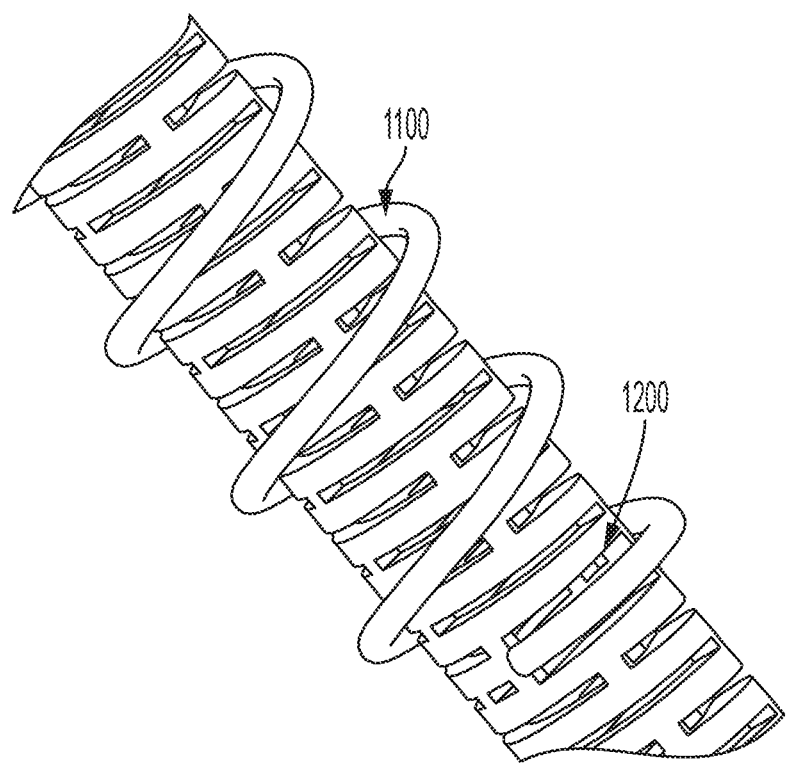
FIG. 13 shows another view of a tubular module having a wrapped filament terminating the cut opening.

A first cut opening 1200, illustrated in FIGS. 12(*a*)-(*d*), can be positioned within the interrupted spiral. The first cut opening 1200 may be oriented orthogonally to the longitudinal axis 1400 of the tubular module or may be positioned at an angle relative to the longitudinal axis 1400. As illustrated in FIG. 13, the filament 1100 can be attached to the tubular module at the first cut opening 1200.

Figure 15A:
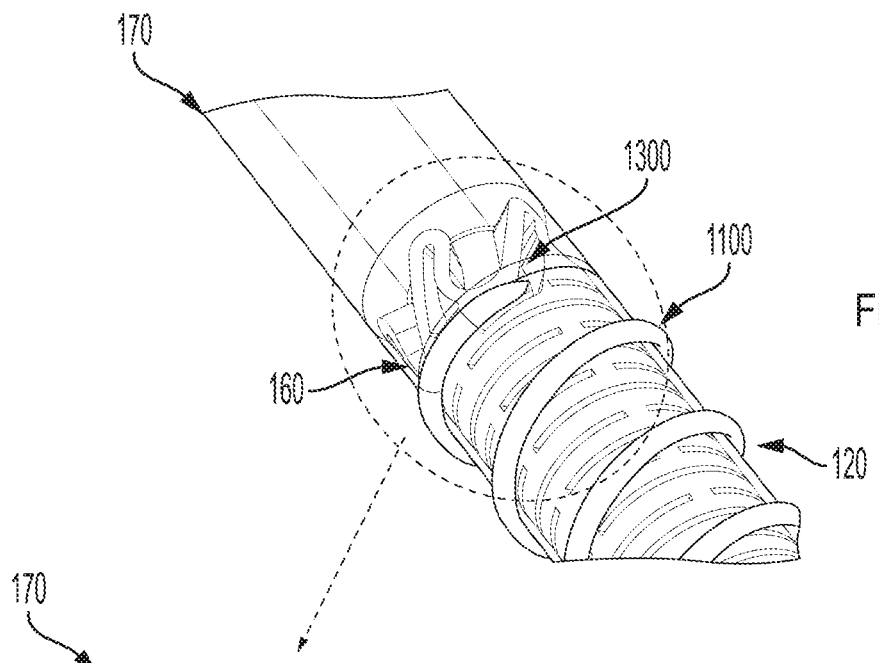
FIG. 15(a) shows a perspective view of the distal tubular module of FIG. 14 and tip having a filament inserted into the second cut opening.
Figure 15B:
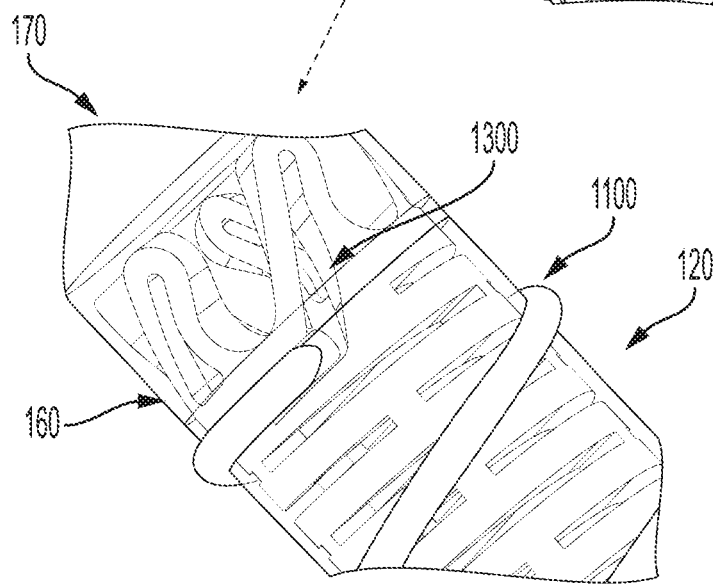
FIG. 15(b) is an enlarged view of the section of FIG. 15(a) outlined in dashed line.
Figure 15C:
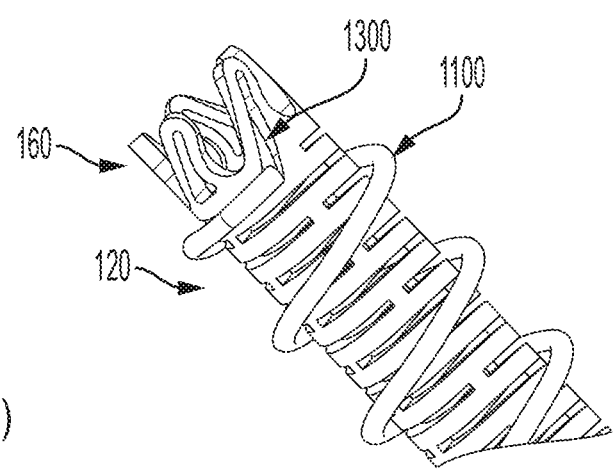
FIG. 15(c) shows another perspective view of the distal tubular module of FIG. 14 having a filament inserted into the second cut opening.

As illustrated in FIG. 14, a second cut opening 1300 may be shaped generally in the form of an "L" which is positioned at the distal end of the tubular module 120 near or adjacent to the crown 160 at which a tip section 170 is secured to the tubular module 120. In one embodiment, the first cut opening 1200 and the second cut opening 1300 are located on the same tubular module. As illustrated in FIGS. 15(a)-(c), the filament 1100 can be attached at the second cut opening 1300.

The walls of the cut openings, 1200, 1300, may be beveled or chamfered. The angle θ of the bevel may range from about 20° to about 70°, or about 40° to about 60° with respect to the long axis 1400 of the tubular module. The shape of the cut openings, 1200, 1300, may vary and may be oval, square, L-shaped (See, 1300, FIG. 14), V-shaped, curvilinear or circular.

FIGS. 14, 15(a)-15(c) and 16(a)-16(f) illustrate one embodiment where the distal end of the distal tubular module 120 has a crown 160. The crown 160 may be made from a plurality of closed, curvilinear elements which can be sinusoidal or generally wave-form (meandering) in shape. In one embodiment, there may be a plurality of curvilinear elements, e.g., ranging from 5-20. FIGS. 15(a)-(c) show an embodiment where the tip 170 is attached to the distal tubular module 120. The filament 1100 is attached to the cut opening 1300 of the distal end 160 of the distal tubular module 120. The distal tubular module 120 and tip 170 may be covered with a jacket 175. The jacket can act to secure the tip 170 to the distal end 160 of the distal tubular module 120.

Figure 16C:
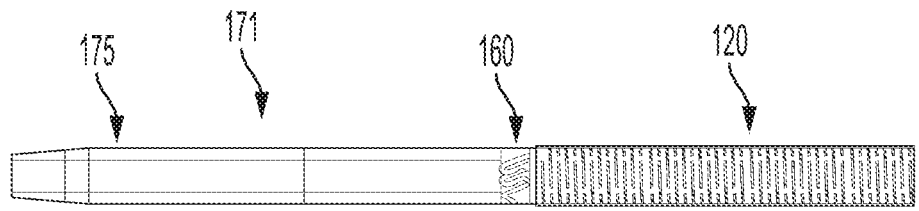
FIG. 16(c) is a side view of the embodiment shown in FIGS. 16(a) and 16(b).
Figure 16D:
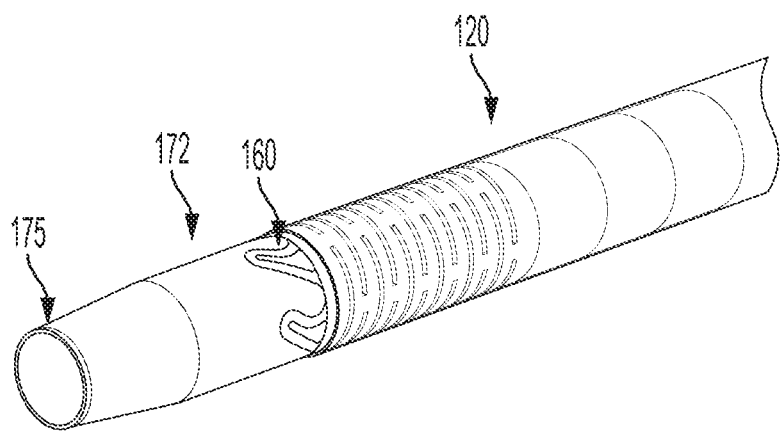
FIG. 16(d) shows perspective a view of another embodiment of a tip that can be used with the modular catheter according to the present invention.

In one embodiment, shown in FIG. 16(a)-(d), the distal end 160 of the distal tubular module 120 can attach to a tip 170. The tip may comprise a hollow tubular body and may be conically tapered as shown in FIGS. 16(a) and 16(b). In addition, the hollow tubular body of the tip can be threaded. The tip 170 may be coated with a jacket 175. FIG. 16(c) shows an illustration of a comparatively elongated tip 171, while FIG. 16(d) shows an illustration of a comparatively shorter tip 172. The tip may be configured with differences in tapering, durometer, rigidity, shape, length, radiopacity, profile, and composition as compared with either the catheter or the proximal or distal tubular modules. The tip can be made of a super-elastic alloy with shape memory. The shape of the tip can be set by heat treatment. For example, the tip may be made from or incorporate radiopaque materials such as gold.

Figure 16E:
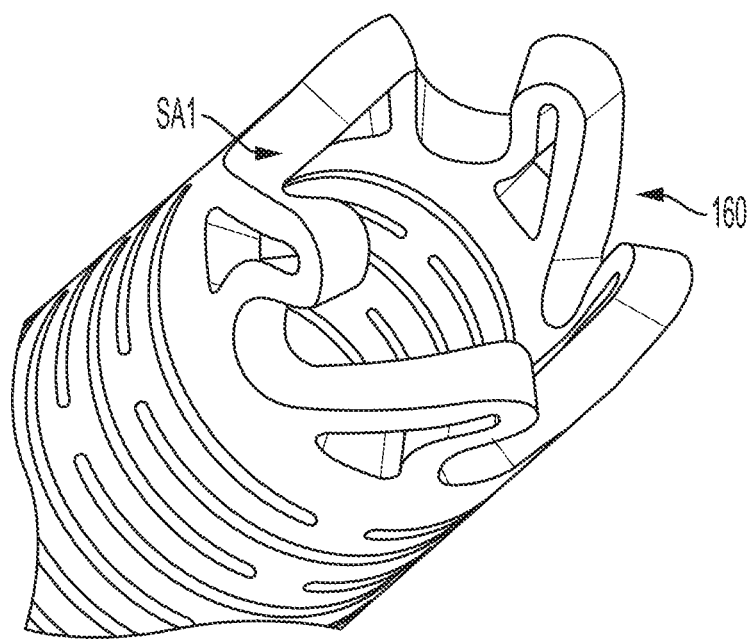
FIG. 16(e) shows a perspective view of a crown face of a distal tubular module.
Figure 16F:
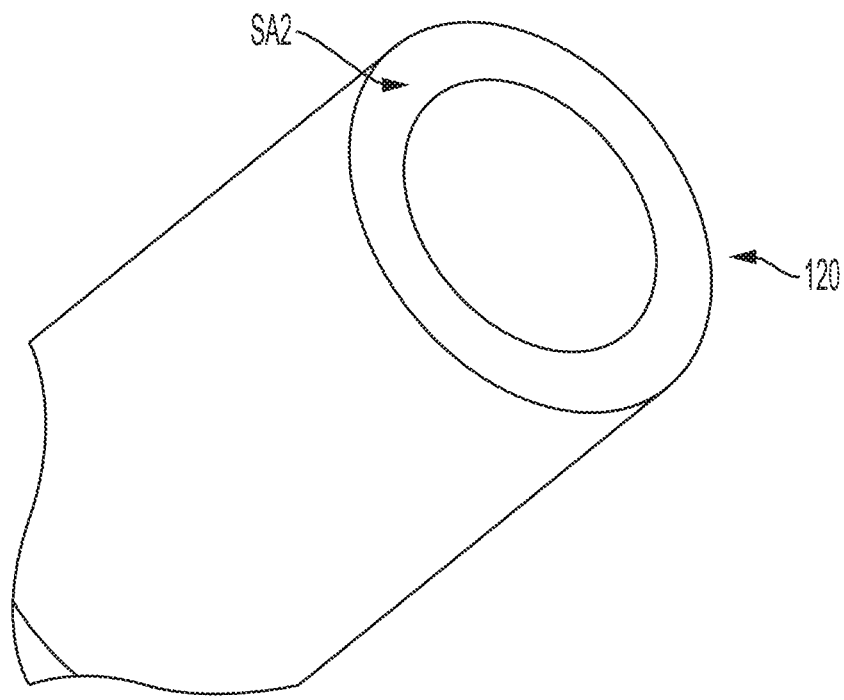
FIG. 16(f) shows a perspective view illustrating the reduced surface area of the attachment portion without additional surface features.

As illustrated in FIGS. 16(e) and (f), due to the curvilinear structure (e.g., prongs) of the crown 160, the surface area of the crown (SA1) can be greater than the surface area of the distal end of the distal tubular module (SA2). The greater surface area of the crown allows for greater surface area contact, and, therefore, binding, between the crown 160 and the tip 170.

Figure 17A:
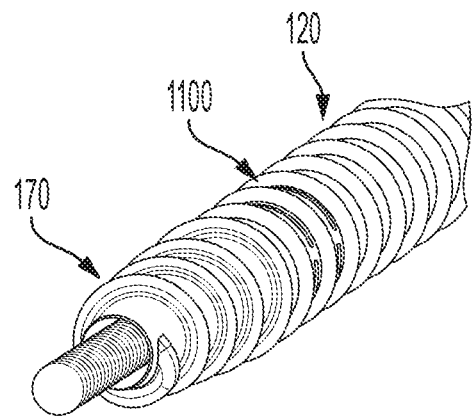
FIG. 17(a) shows a perspective end view of an embodiment in which a filament is wrapper around the tubular module and tip attached to the tubular module is threaded, with a guidewire exiting from the tip.
Figure 17B:
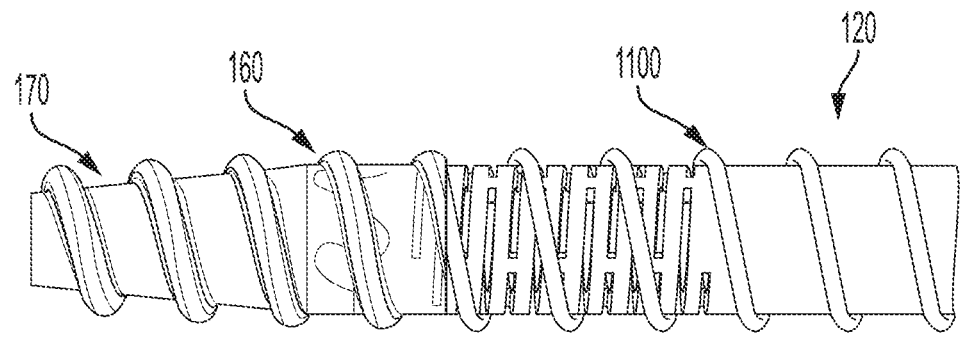
FIG. 17(b) shows a side view of the embodiment shown in FIG. 17(a).
Figure 17C:
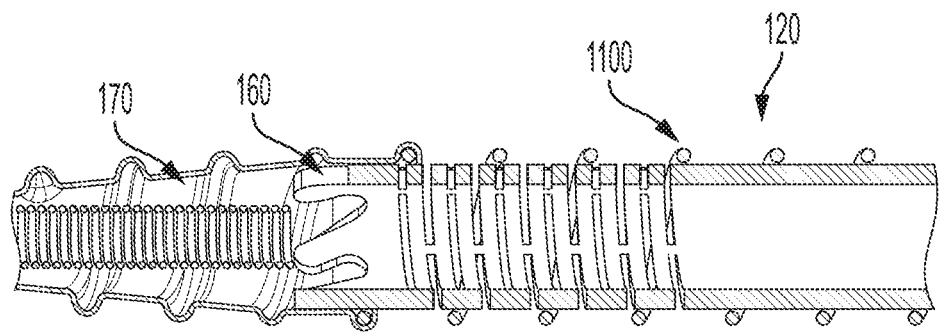
FIG. 17(c) shows a cross-section of the shown in FIG. 17(b).

As depicted in FIGS. 17(a)-(c), a filament 1100 can be wound spirally around both the proximal or distal tubular modules 110, 120, and also can continue to spiral around the tip 170. In embodiments in which the tip is a hollow tube including threads, the filament can be fitted into the threads of the tip as shown in FIG. 17(b). The filament 1100 may proceed around all or only a portion of the tip 170. The filament may be wound around the modules in a clockwise or counter-clockwise spiral manner. In other embodiments, the tip may be fabricated with a threaded structure of its own. The filament of the tip may also be covered with a jacket.

Figure 19A:
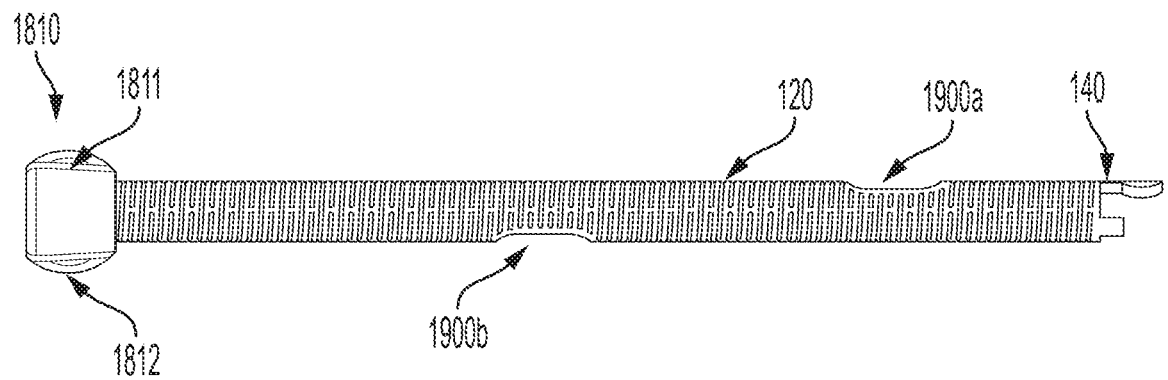
FIG. 19(a) shows a side view of an embodiment of a distal tubular module having side port exits and coupled to a vessel dissection tip having wings in a top-down orientation according to the present invention.
Figure 19B:
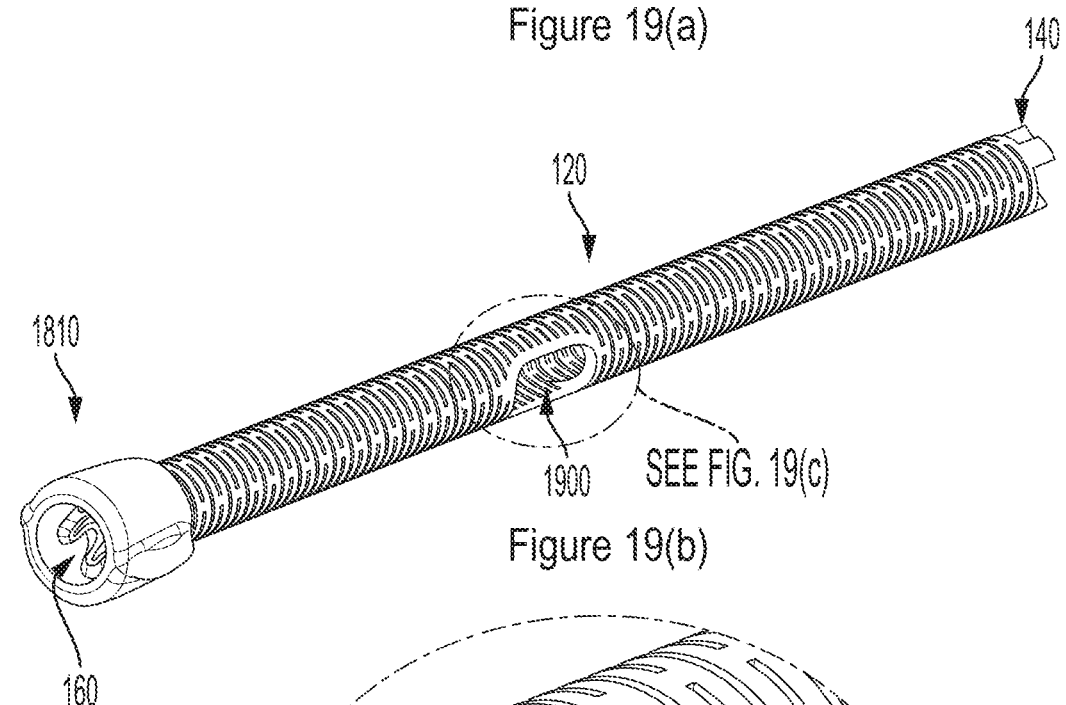
FIG. 19(b) shows a perspective view of the embodiment shown in FIG. 19(a) as rotated by 90°.

In another embodiment, shown in FIGS. 19(a) and 19(b), a re-entry tip can be coupled to the distal end of the distal tubular module with or without directly engaging the prongs of the crown 160. Further description of catheter re-entry is found in commonly owned and assigned U.S. patent application Ser. No. 14/854,242, entitled "Vascular Re-entry Catheter, which is incorporated by reference herein in its entirety. When used with a re-entry tip, the modular catheter can be used in procedures involving re-entry into the true lumen after the creation of a dissection plane.

Figure 18A:
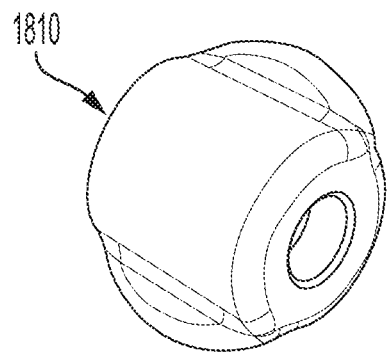
FIG. 18(a) shows a perspective view of an embodiment of a reentry catheter vessel dissection tip according to the present invention.
Figure 18B:
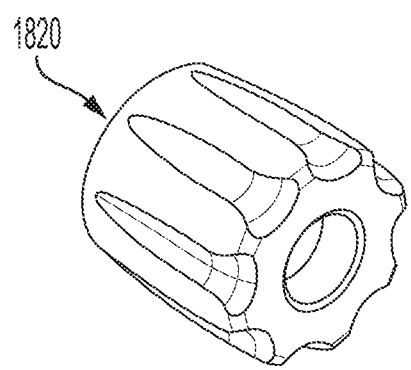
FIG. 18(b) shows a perspective view of another embodiment of a reentry catheter vessel dissection tip according to the present invention.
Figure 18C:
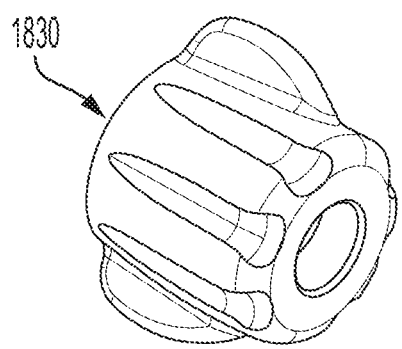
FIG. 18(c) shows a perspective view of another embodiment of a reentry catheter vessel dissection tip according to the present invention.
Figure 18D:
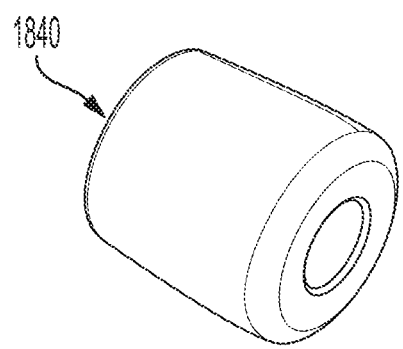
FIG. 18(d) shows a perspective view of another embodiment of a reentry catheter vessel dissection tip according to the present invention.

Examples of re-entry tips are shown in FIGS. 18(a)-18(d). FIG. 18(a) is a re-entry tip 1810 having a smooth surface and two wings disposed on either side of the re-entry tip. FIG. 18(b) is a re-entry tip 1820 having divots in its surface around the entire diameter of the tip. FIG. 18(c) is a re-entry tip 1830 having divots in its surface around the entire diameter of the tip and two wings disposed on either side of the re-entry tip. FIG. 18(d) 1840 is a re-entry tip having a smooth surface and no wings.

Figure 19C:
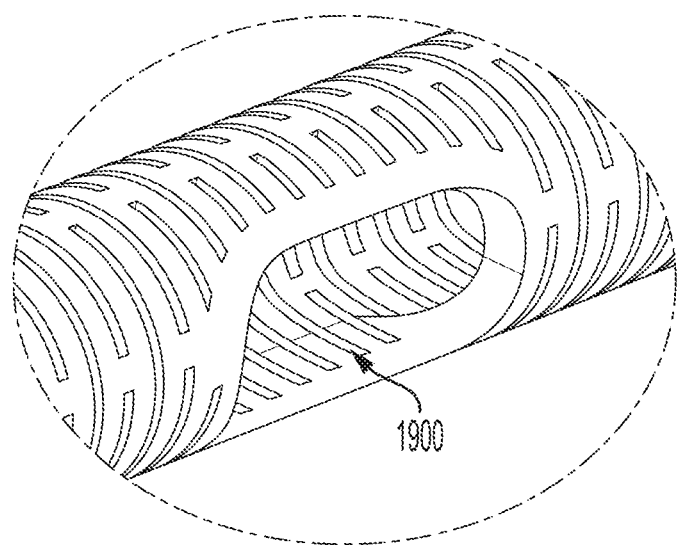
FIG. 19(c) shows an enlarged view of the section of FIG. 19(b) outlined in dashed line.
Figure 19D:
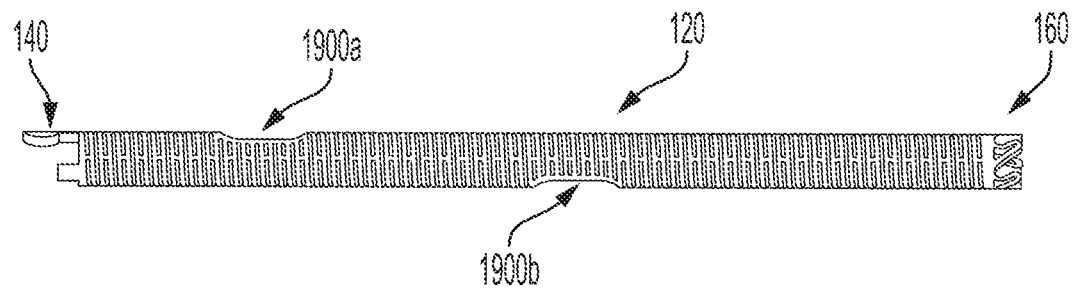
FIG. 19(d) shows a side view of a distal tubular module having side port exits according to an embodiment of the present invention.
Figure 19E:
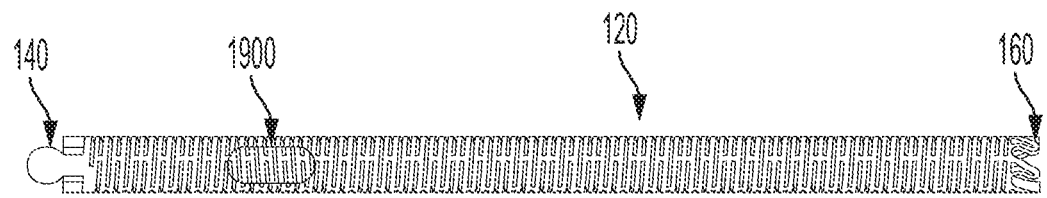
FIG. 19(e) shows a top view of the distal tubular module shown in FIG. 19(d).
Figure 19F:
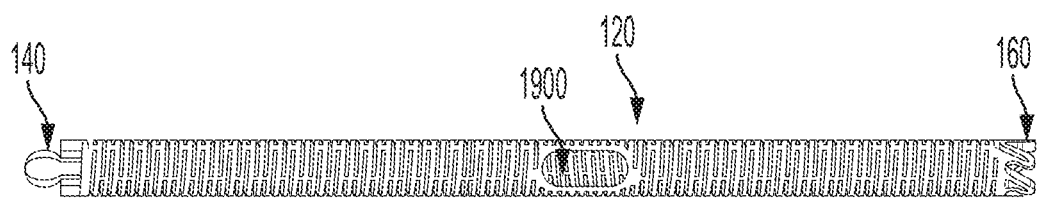
FIG. 19(f) shows a bottom view of the distal tubular module shown in FIGS. 19(d) and 19(e)
Figure 19G:
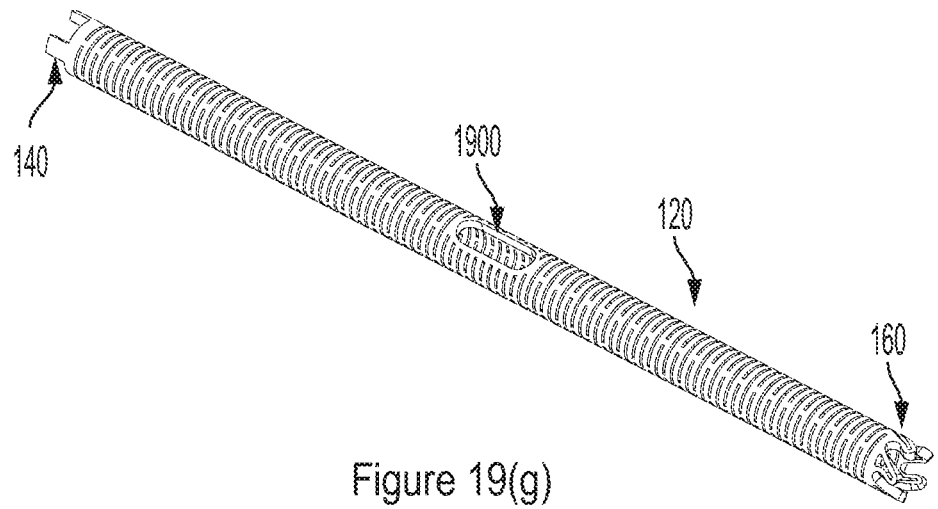
FIG. 19(g) shows a perspective view of the distal tubular module of FIGS. 19(d) to 19(f).

As shown in FIGS. 19(b)-19(c), the modular catheter system 100 can further comprise at least one side port 1900. Some embodiments, as shown in FIGS. 19(a) and 19(d), have two side ports 1900a, 1900b. More than two side ports can be used. In the embodiments having more than one side port, the side ports can all be aligned linearly down the length of the catheter system 100. In other embodiments, the side ports can be aligned around the diameter of the catheter system 100. The side ports can be evenly spaced down the length of the catheter system 100, or they can be spaced at specific locations. In another embodiment, the side ports are disposed only on the distal tubular module 120.

Referring to FIG. 19(a), side ports 1900a and 1900b can be positioned radially offset, between about 180° apart from each other, e.g., about 180° (±10°). A re-entry tip 1810 includes wings 1811, 1812 also spaced apart by approximately 180°. In general, the radial displacement of the side ports relative to the wings may range from about 0° to 90°, e.g., 10°, 20°, 300, 50°, 70° and 80°. In one embodiment, the positions of the side ports may be radially offset from the wings at about 90°. In this way, when the two wings 1811 and 1812 are positioned in a stable configuration in the subintimal space of an artery, port 1900a can be facing either toward or opposing the true lumen of the artery, and the port 1900b can face the opposite side.

The side ports may be symmetrical in shape and can be circular, semi-circular, ovoid, semi-ovoid, rectangular or semi-rectangular. The side ports may have the same shape and size (i.e., surface area) or can be different from each other and are configured to allow for passage of a re-entry wire or another medical device through the ports. The dimensions of the port may be adjusted to accommodate different types of medical devices or wires, e.g., with diameters ranging from about 0.05 mm to about 1.0 mm. Erglis et al. *Eurointervention* 2010:6, 1-8. The distal tube portion 120 can contain more than two exit ports, e.g., 3, 4, 5, 6, 7, 8 . . . n ports along its length direction and radially distributed as desired.

The side port may be beveled. The beveled configuration of the side port can facilitate a re-entry wire with a bent tip to smoothly exit and regress from the side port. The angle θ of the bevel may range from about 0° to about 90°, including, 10° to about 90°, about 20° to about 70°, or 40° to about 60°.

In one embodiment, at least two radiopaque markers and positioned along distal tubular portion 120 for aiding radiographic visualization of the positioning of the catheter 100 in the vascular lumen. The markers can include a radiopaque material, such as metallic platinum, platinum-iridium, Ta, gold, etc., in the form of wire coil or band, vapor deposition deposits, as well as radiopaque powders or fillers, e.g., barium sulfate, bismuth trioxide, bismuth sub carbonate, etc., embedded or encapsulated in a polymer matrix. Alternatively, the markers can be made from radiopaque polymers, such as radiopaque polyurethane. The markers can be in the form of bands to encircle the outer sheath of the distal tubular portion.

The radiopaque markers configured as bands can be used to facilitate determination of the positions of the side ports while the distal tube portion 120 is maneuvered in a subject's anatomy. The markers can also be configured as a partial band or patch which forms specific alignment with a corresponding side port. For example, one marker can be axially aligned with side port 1900*a*, whereas a second marker can be axially aligned with side port 1900*b*. Thus, like the radially opposite configuration of the side ports 1900*a* and 1900*b*, the markers are also radially opposite to each other. In this manner, visualization of the markers can be used to determine the orientation of the respective side ports. The markers can be configured in different shapes, e.g., partial circumferential bands, or any other desired shapes, to facilitate determination of orientation of the ports.

The markers can also be configured as surface patches that enclose the circumferences of the respective side ports 1900*a* and 1900*b*. In such an embodiment, the marker positions that can be visualized directly correspond to the side port positions.

The markers should have sufficient size and suitable configuration/construction (e.g., the type of radiopaque material, load amount of radiopaque material, etc.) such that they can be visualized with the proper radiographic aid.

The variable flexibility of the sections of the tubular modules also facilitates surgical procedures in which side-branch access is required or where tortuous vasculature is encountered such as in the central nervous system. Given the ability to use a wide variety of combinations from the base tube's material mechanical properties, the tubing dimensions (OD/ID), wall thickness, cut tubing's mechanical properties resulting from the cut pattern along the tube's (material composition, UTS, % Elongation modulus of Elasticity, and other combinations of material and mechanical properties (UTS, formulas defining cut pitch angle, cut width, helical cut arc length and uncut helical space between next helical arc cut), all enable the designer to tailor a variety of mechanical properties defined throughout the running length of the cut tube. Such resulting properties such as stiffness, flexibility and using the shape memory properties define a preset curvilinear shape are programmable and changeable.

Additionally, such an induced shape memory form would require a greater force to straighten or diminish and maintain via a resistive load force along the cut and shape treated portion of the distal tubular segment, to orient the shape set portion of the tube to revert back into a straight linear concentric coaxial configuration, which would enable the catheter to be advanced to the vascular target.

Such variables assembled together, to create a wide variety of structural shape combinations of tubular modules. These structural shapes can easily be temporarily diminished inline by advancing the tubular modules over a wire track, e.g., a guidewire, which exhibits mechanical properties of deformation that exceed the curvilinear shape's spring constant. This temporary deformation enables advancement of the catheter, the tubular modules, over the guidewire through the vascular anatomy. Simply put, the spring constant of the shaped curve portion is less than that of the wire segment it is tracking over. Once the retaining guidewire segment's spring constant is less than that of the set curvilinear shape, the cut shaped tube segment will revert back to its preset shape, unless acted upon by an additional other external forces or vascular confinement.

The distal modules of the present invention can include portions that bend or hook or are set in-place in a curvilinear shape through the application of shape memory. As noted above, super-elastic alloys including Nitinol have this property, which can be modified by heating. FIGS. 20(*a*) and 20(*b*) depict a side view and an end view, respectively of a distal end of a catheter according to the present invention that includes this feature. As shown in the side view, a portion of a distal tubular module 2020 includes at its distal end a curvilinear section 2030 that bends. The bend can be at least one of: a curve, a sinusoidal curve, a non-linear section, an angulation, a peak, a valley, a squiggle, curvilinear, and helical. The bend can have a variable stiffness. The bend can have a stiffness coefficient greater than the remaining portion of the elongated member.

The curvilinear section can bend from about 0° to about 180° with respect to the longitudinal axis (L, FIG. 21(*a*)) of the tubular module. The curvilinear shapes of the section can vary and include, flush, simple curves, complex curves, reverse curves or double curves. The length of the curvilinear section can vary and may encompass only a portion or the entire length of the tubular module. In the embodiment shown in FIG. 20(*a*), the curvilinear section 2030 assumes the 45° unless a force, e.g., a guidewire, is applied to straighten or otherwise alter its configuration. Force may be applied through a variety of means, such as a guidewire which is inserted into the lumen of the tubular module and is co-axial with the lumen of the tubular module. The end view in FIG. 20(*b*) shows a lumen 2050 of the distal tubular module. This cross-section of the lumen remains constant during bending of the curvilinear section 2030. This constant cross-sectional lumen facilitates passage of wires and other devices through the vasculature.

The catheter can include a guidewire which can be passed through the lumen of the tubular modules. The tubular modules can be passed over the guidewire into an artery. Guidewires are typically comparatively thin, having a diameter in the order of about 0.254 mm to 0.457 mm. Guidewires are capable of transmitting rotation from the proximal end of the guidewire to the distal end of the guidewire. This transmission allows the physician to controllably steer the guidewire through the branches of the patient's arteries and manipulate the catheter to the intended target site in the coronary artery. Additionally, the distal end of the guidewire should be sufficiently flexible to allow the distal portion of the guidewire to pass through sharply curved, tortuous coronary anatomy.

Among the common guidewire configurations used in angioplasty is the type of guidewire illustrated in U.S. Pat. No. 4,545,390. Such a wire includes an elongate flexible shaft, typically formed from stainless steel, having a tapered distal portion and a helical coil mounted to and about the tapered distal portion. The generally tapering distal portion of the shaft acts as a core for the coil and results in a guidewire having a distal portion of increasing flexibility that is adapted to follow the contours of the vascular anatomy while still being capable of transmitting rotation from the proximal end of the guidewire to the distal end so that the physician can controllably steer the guidewire through the patient's blood vessels. The characteristics of the guidewire are affected significantly by the details of construction as the distal tip of the guidewire. For example, in one type of tip construction, the tapering core wire extends fully through the helical coil to the distal tip of the coil and is attached directly to a smoothly rounded tip weld at the distal tip of the coil. Such a construction typically results in a relatively stiff tip suited particularly for use when attempting to push the guidewire through a tight stenosis. In addition to a high degree of column strength, such a tip also displays excellent torsional characteristics.

In another type of tip construction, the tapered core wire terminates short of the tip weld. It is common in such a construction to attach a very thin metallic ribbon at one (proximal) end to the core wire and at its other (distal) end to the tip weld. The ribbon serves as a safety element to maintain the connection between the core wire and the distal tip weld in the event of coil breakage. It also serves to retain a bend formed in the ribbon to maintain the tip in a bent configuration as is desirable when manipulating and steering the guidewire. Additionally, by terminating the core wire short of the tip weld, the segment of the helical coil between the distal end of the core wire and the tip weld is very flexible and floppy. The floppy tip is desirable in situations where the vasculature is highly tortuous and in which the guidewire must be capable of conforming to and following the tortuous anatomy with minimal trauma to the blood vessel. In another type of tip construction, the distal-most segment of the core wire is hammered flat (flat-dropped) so as to serve the same function as the shaping ribbon but as an integral unitary piece with the core wire. The tip of the flat dropped segment is attached to the tip weld. Guidewires are well known in the art and the appropriate choice of a guidewire for use the catheter of the present invention can be made by a medical professional, such as an interventional cardiologist or interventional radiologist.

FIGS. 21(a) and 21(b) depict a side view and end view of another embodiment of a distal end of a catheter according to the present invention. In this embodiment, a distal tubular module 2120 includes at its distal end a curvilinear section 2130 that naturally assumes a 90° bend from the point at which it is connects to the remainder of the distal tubular module (i.e., the horizontal axis) up to a tip 2140. The curvilinear section assumes the 90° bend unless a force is applied to straighten or otherwise alter its configuration. The end view in FIG. 21(b) shows a lumen 2150 of the distal tubular module. This lumen can maintain a constant cross-section in distal tubular module lumen is maintained within the curvilinear section 2130.

FIG. 22 shows a side view of still another embodiment of a distal end of a catheter according to the present invention. In this embodiment, the curvilinear section 2230 of a distal tubule module 2220 bends still further, to approximately 180°, such that the tip 2240 point toward the distal tubular module and aligns approximately parallel with the longitudinal axis, L, of the distal tubular module.

Figure 23:
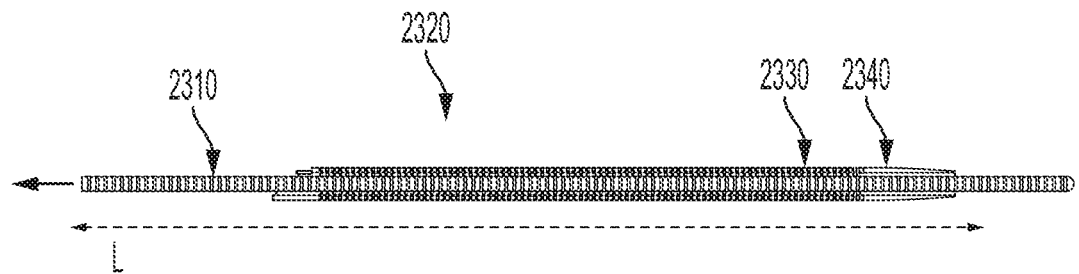
FIG. 23 is a cross-sectional view illustrating a distal tubular module having a curvilinear section that is straightened by a guidewire extending through the tubular module and tip.
Figure 24:
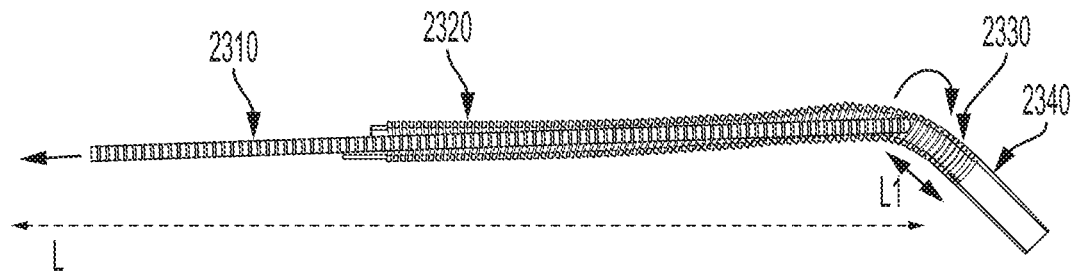
FIG. 24 is a cross-sectional view illustrating withdrawal of the guidewire, allowing the curvilinear section to begin to assume its curvilinear shape.
Figure 25:
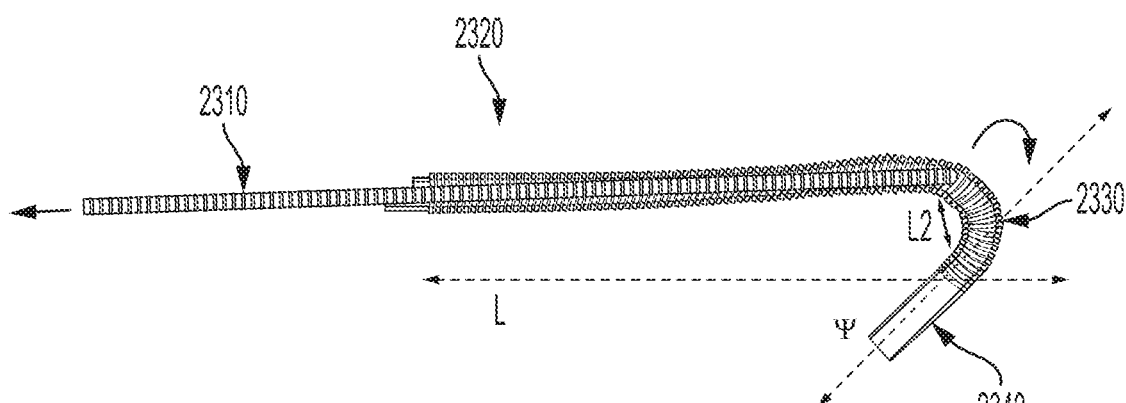
FIG. 25 is a cross-sectional view following on FIG. 24, illustrating the curvilinear section adapted for side-branch access.

FIGS. 23-25 shows three parts of a sequence in which the tubular modules, include a curvilinear section together with a guidewire. Any conventional guidewire may be used with the present invention. For example, the central core of the guidewire may be formed from Stainless steel, Durasteel™ or nitinol/Lastinite®. The guidewire may be covered with a polymer sleeve or a coil-spring tip and coated with a lubricious coating.

FIG. 23 is a cross-sectional view illustrating a distal tubular module having a curvilinear section 2330 that is straightened-out by passing the distal tubular module 2320 over a guidewire 2310 extending through the tubular module 2320 and tip 2340. As shown, the guidewire 2310 extends through the end portion of the distal tubular module 2320, passing through the shape-memory, curvilinear section 2330, past the tip 2340 of the tubular module. In this position, the guidewire 2310 keeps the curvilinear section 2330 aligned or straight with respect to the longitudinal axis (L) of the distal tubular module 2320 and prevents the curvilinear section from bending in accordance with its shape memory. In other words, the spring constant of the curvilinear section 2330 is less than that of the spring constant of the guidewire 2310 segment that the distal tubular module 2320 is tracking over. If the spring constant of the retaining guidewire 2330 segment is less than the spring constant of the curvilinear section 2330, the curvilinear section 2330 will revert back to its preset shape, unless acted upon by an additional other external forces or vascular confinement.

In FIG. 24, the guidewire 2310 has been withdrawn in the leftward direction (as shown by the arrow) from the tip 2340 and a distance (L1) within the preset curvilinear section 2330 of the distal tubular module 2320. As shown in FIG. 24, as the guidewire 2310 is withdrawn, the preset curvilinear section 2330 begins to bend and assume its preset shape as discussed above.

In FIG. 25, the guidewire 2310 has been withdrawn still further from the position shown in FIG. 24, i.e., L2>L1, within the curvilinear section 2330. As a result, the curvilinear section 2330 continues to bend in accordance with its shape memory such that the angle between the direction in which the tip 2340 faces and the longitudinal axis, L, of the distal tubular module 2320 ($\Psi$) is greater than 90°. The range of bending ranges from about 0° to about 180° with respect to the longitudinal axis, L. In this embodiment, the distal end of the distal tubular module in this position is configured in the shape of a "Shepherd's Hook" and is better adapted, in this configuration, to access side-branches in the arterial system or for access into tortuous vasculature.

Figure 26:
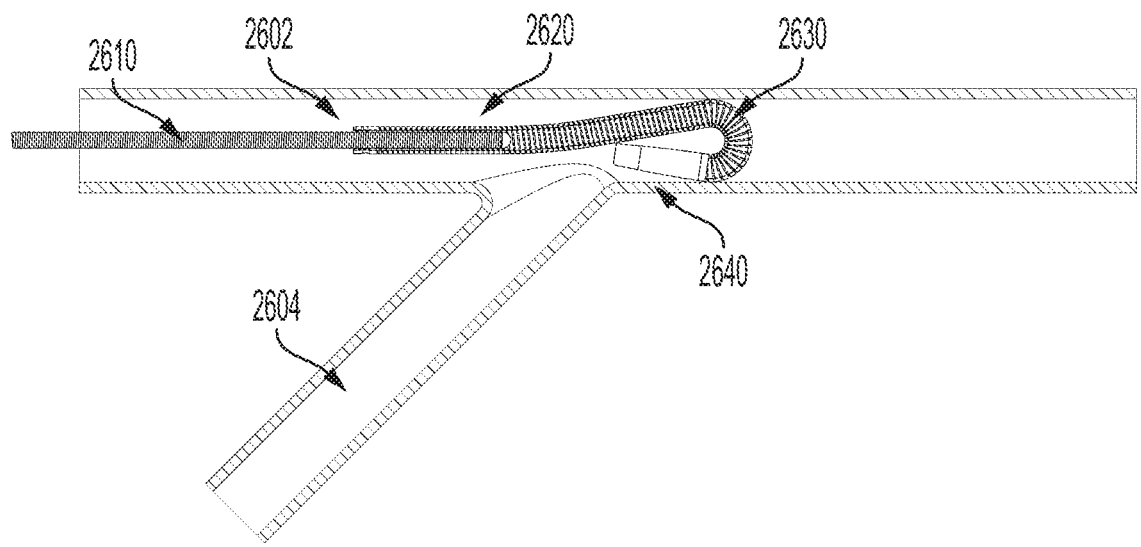
FIG. 26 is cross-sectional view showing a portion of the distal tubular module according to an embodiment of the present invention within an artery, with a shape-memory curvilinear section accessing a side branch.
Figure 27:
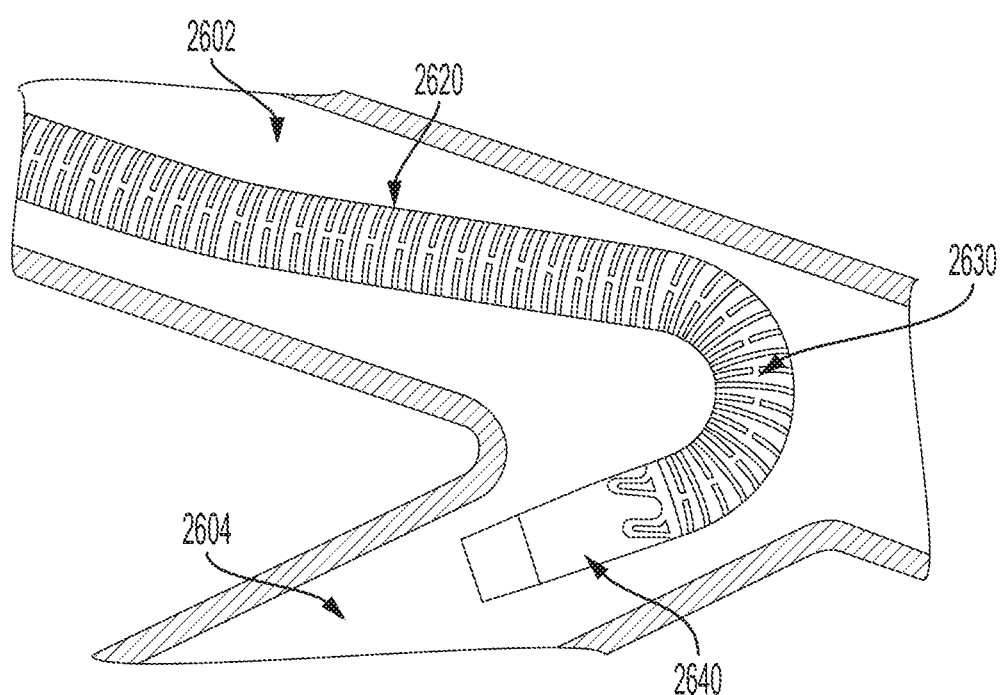
FIG. 27 is cross-sectional view of the artery showing a portion of the distal tubular module according to an embodiment of the present invention within an artery, with a shape-memory curvilinear section accessing a side branch.

FIG. 26 shows an example of the catheter and distal tubular module with a curvilinear section with shape memory as it can be applied for side-branch artery access.

In the Figure, a main arterial branch 2602 and a side-branch artery 2604 which joins to and branches-off from the main artery 2602 are shown. The distal end of a catheter, including a distal tubular module 2620, together with a preset, curvilinear section 2630 and tip 2640 are shown. In the Figure, the guidewire 2610 has been withdrawn from the curvilinear section 2630, allowing the curvilinear section to bend to about 180° with respect to the longitudinal axis of the tubular module (see, L, FIGS. 23-25, supra.).

As the catheter, which includes the distal tubular module 2620 is moved laterally in the artery the curvilinear section 2630 can enter the side branch 2604. Note, a torquing force may be applied to the catheter by rotating the hub which can rotate the proximal and distal tubular modules about the central axis.

Figure 28A:
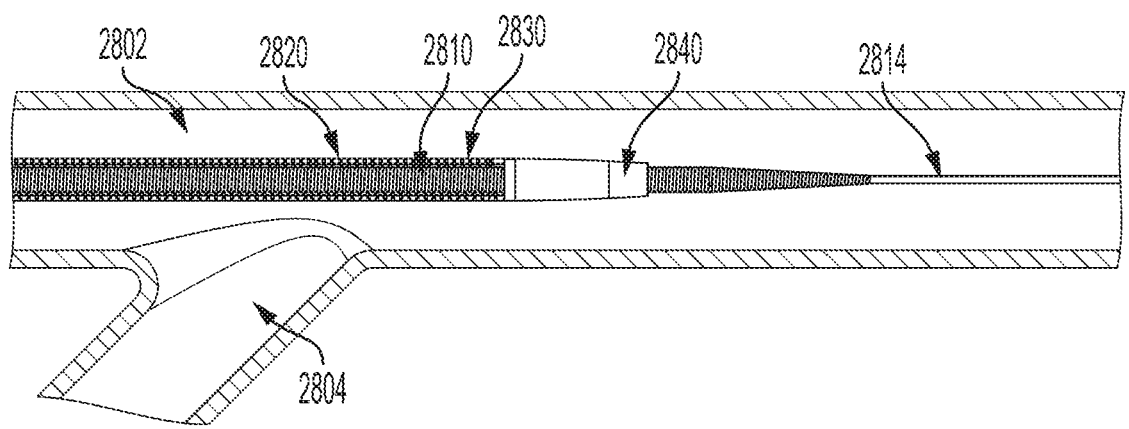
FIG. 28(a) shows a cross-section of an example section of an artery system having a main artery and a side-branch artery, a modular catheter with a shape memory curvilinear section and guidewire according to the present invention is positioned in the main artery.

FIG. 28(a) shows a cross-sectional view of an arterial system which comprises a main vessel 2802 together with a single side branch artery (also referred to as a side branch) 2804. In the example shown, the diameter of the main artery 2802 is greater than the diameter of the first side-branch 2804. A distal tubular module 2820 is shown positioned in the artery 2802 where the distal tubular module extends past the side branch artery 2804. The guidewire 2810 extends past the end of the distal tubular module 2820 and the tip 2840. The guidewire 2810 includes a tapered section 2814. As discussed above, the guidewire 2810 straightens-out the pre-set, curvilinear section 2830 of the distal tubular module 2820.

Figure 28B:
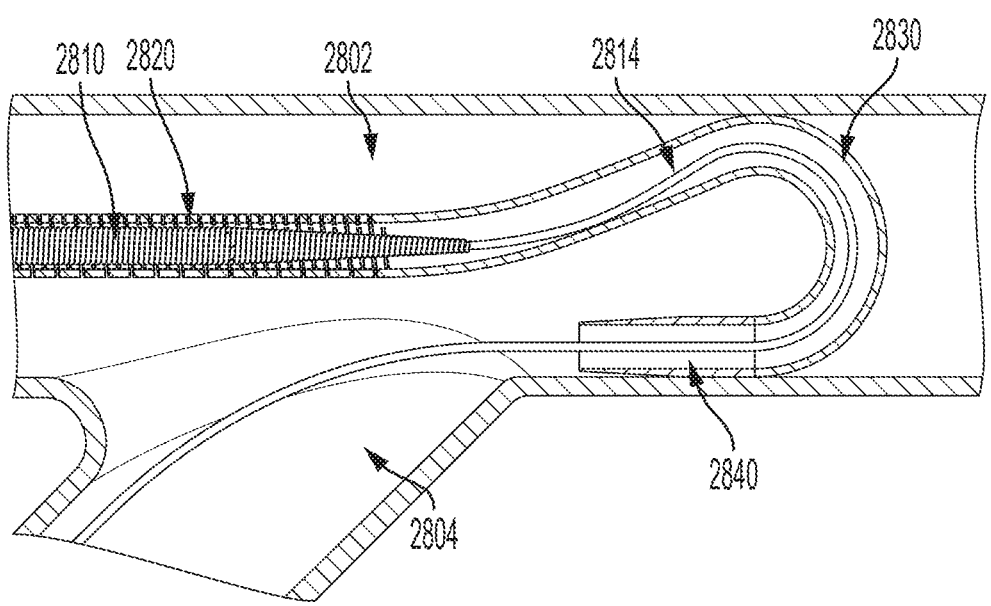
FIG. 28(b) shows the view of FIG. 28(a) in which the guidewire has been withdrawn, allowing the curvilinear section to assume a bent shape.

FIG. 28(b) shows the guidewire 2810 partially withdrawn from the distal tubular module 2820, allowing the curvilinear section 2830 to bend. The tip 2840 and the tapered end 2814 of the guidewire 2810 reposition in accordance with the bending of the curvilinear section 2830 and enter into the side branch of the artery 2804 or position the tip 2840 allowing for entry into the side branch 2804.

Figure 28C:
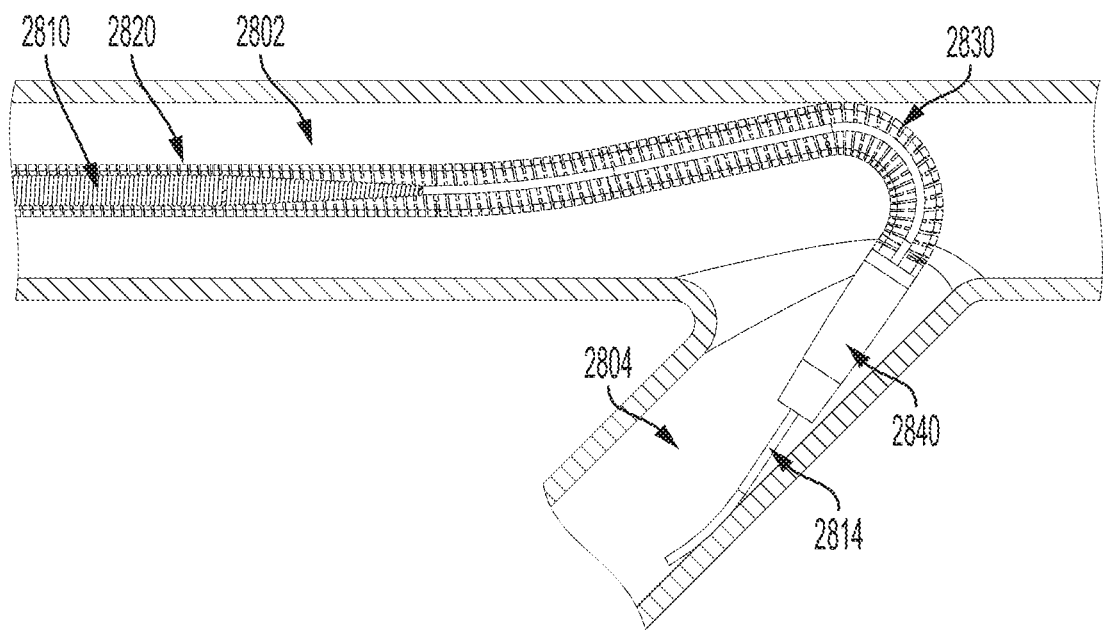
FIG. 28(c) shows the view of FIG. 28(b) with the guide wire and tip aligning for access into the side branch.

In FIG. 28(c), the guidewire 2810 is withdrawn further from the distal tubular module 2820. The tip 2840 and the tapered end of the guidewire 2814 are aligned with the axis of the side branch 2804.

Figure 28D:
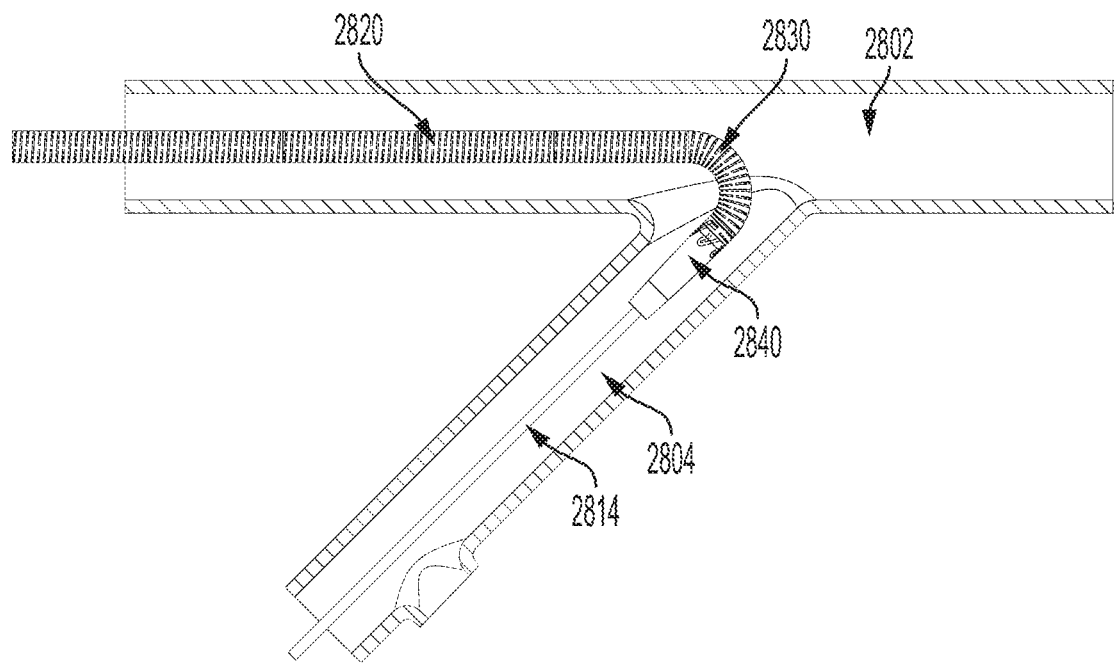
FIG. 28(d) shows as side view of the tip of the catheter inserted into the side branch and the guidewire extended out of the tip of the catheter through the side branch.
Figure 28E:
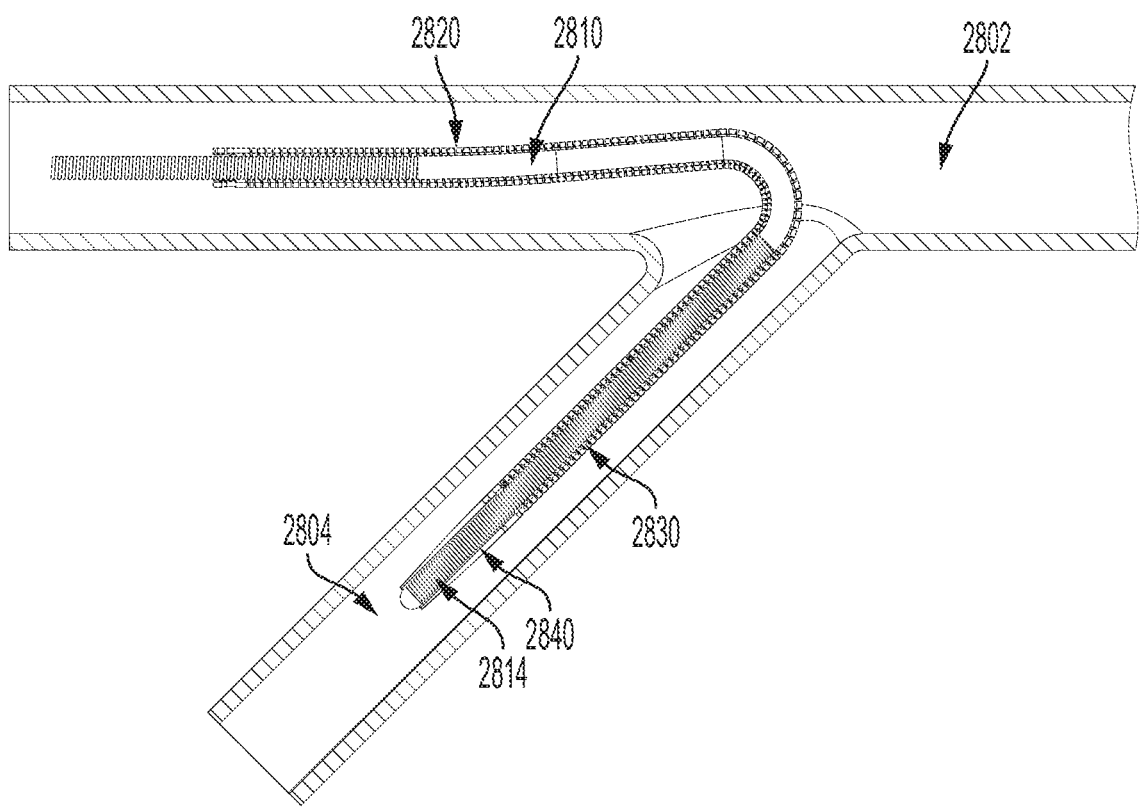
FIG. 28(e) shows the view of FIG. 28(d) with the catheter advanced through the side branch over the guidewire.

In FIG. 28(d), the tapered end of the guidewire 2814 is extended past the tip 2840 into the side branch 2804. Then, in FIG. 28(e), the distal tubular module 2820 is advanced over the guidewire 2810 down through the side branch 2804.

Figure 29A:
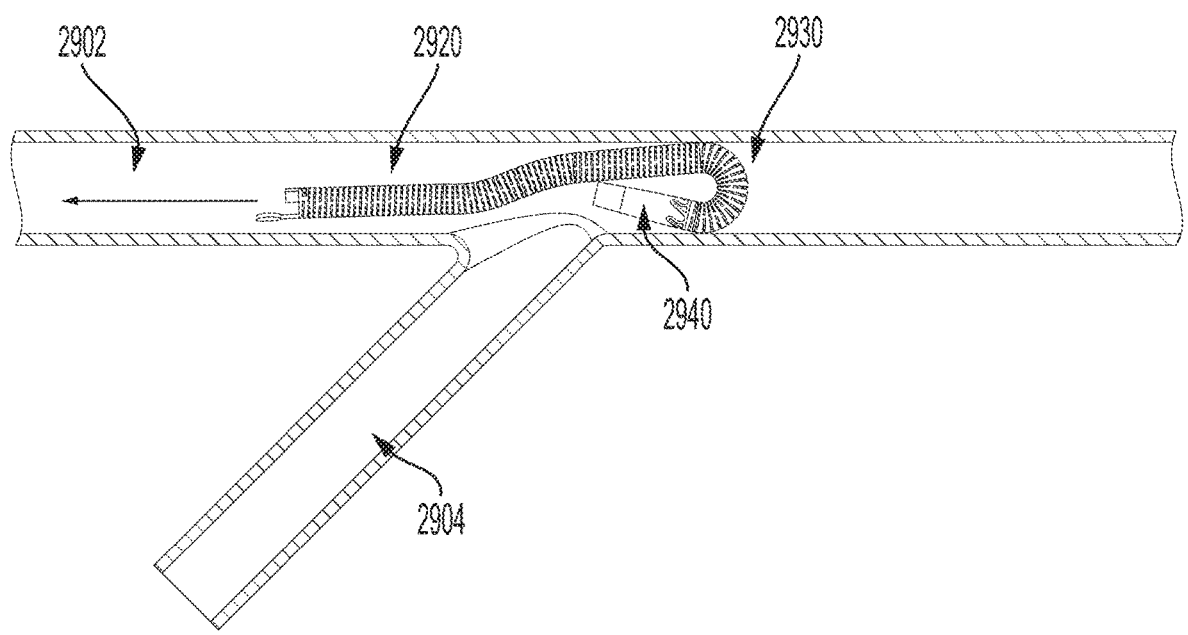
FIG. 29(a) shows a cross-section of an example section of an artery system having a main artery and a side-branch artery, a modular catheter with a shape memory curvilinear section in a bent shape and guidewire according to the present invention is positioned in the main artery.

FIG. 29(a) shows another method for enabling access to arterial side branches. As depicted, a distal tubular module 2920, including a preset, curvilinear section 2930 and tip 2940 are positioned in a main artery 2902 with a guidewire having been withdrawn. The preset, curvilinear section 2930 and tip 2940 are positioned past (in the forward movement direction) the junction of the main artery 2902 with a side branch 2904. Because of shape memory in the preset curvilinear section 2930, this section and the tip are in shown in a bent or Shepherd's Hook position. In the example shown, the tip is bent 180° in the reverse movement direction, parallel to the longitudinal axis. The preset bend can also be at other angles (e.g., 45°, 90°, 120°, etc.). From this position, as the distal tubular module 2920 is withdrawn, a torque force 2945 can be applied to rotate the distal tubular module 2920 clockwise or counterclockwise. The distal tubular module 2920 can then be inserted into the side branch 2904.

Figure 29B:
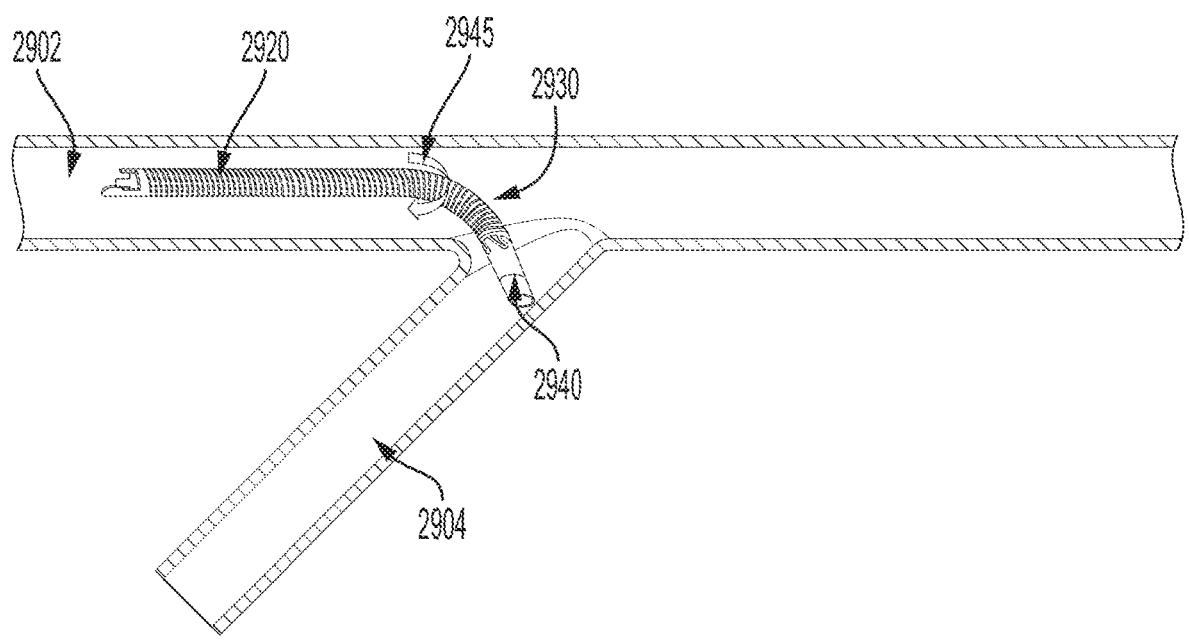
FIG. 29(b) shows the view of FIG. 29(a) after the catheter has been withdrawn backwards and torqued to angle the tip toward the opening of the side branch.
Figure 29C:
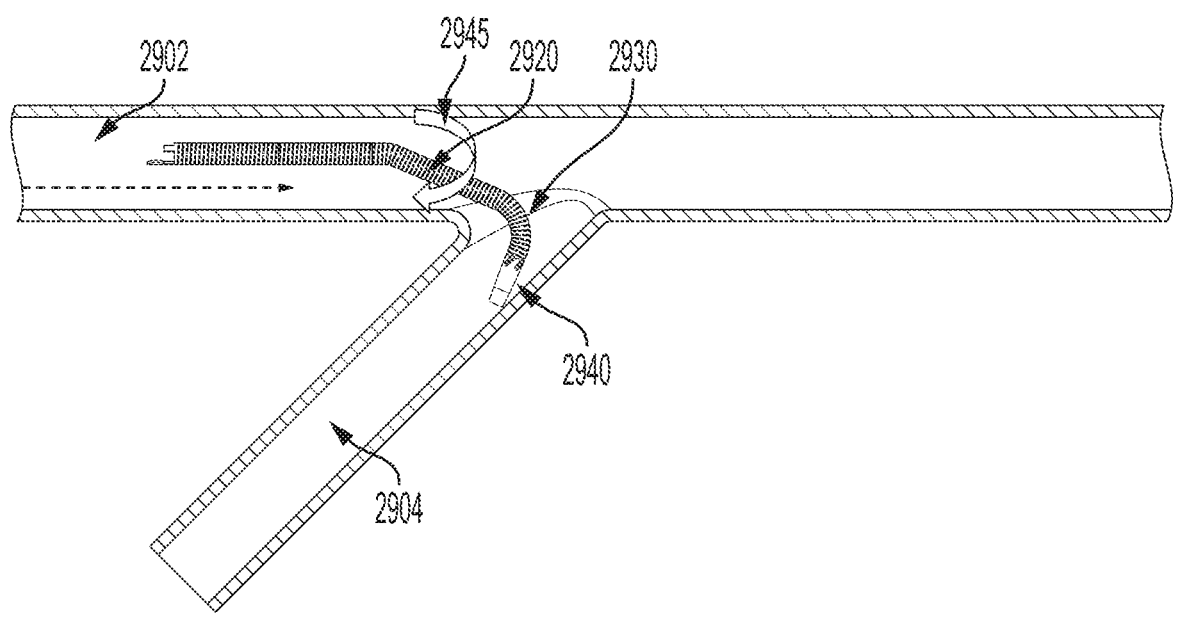
FIG. 29(c) shows the view of FIG. 29(b) with the tip of the catheter further advanced into the side branch.

FIG. 29(c) shows the distal tubular module 2920 and tip 2940 having entered further into the side branch 2904 from the position shown in FIG. 29(b). In FIG. 29(c) the tip approaches alignment with the axis of the side branch 2904.

Figure 29D:
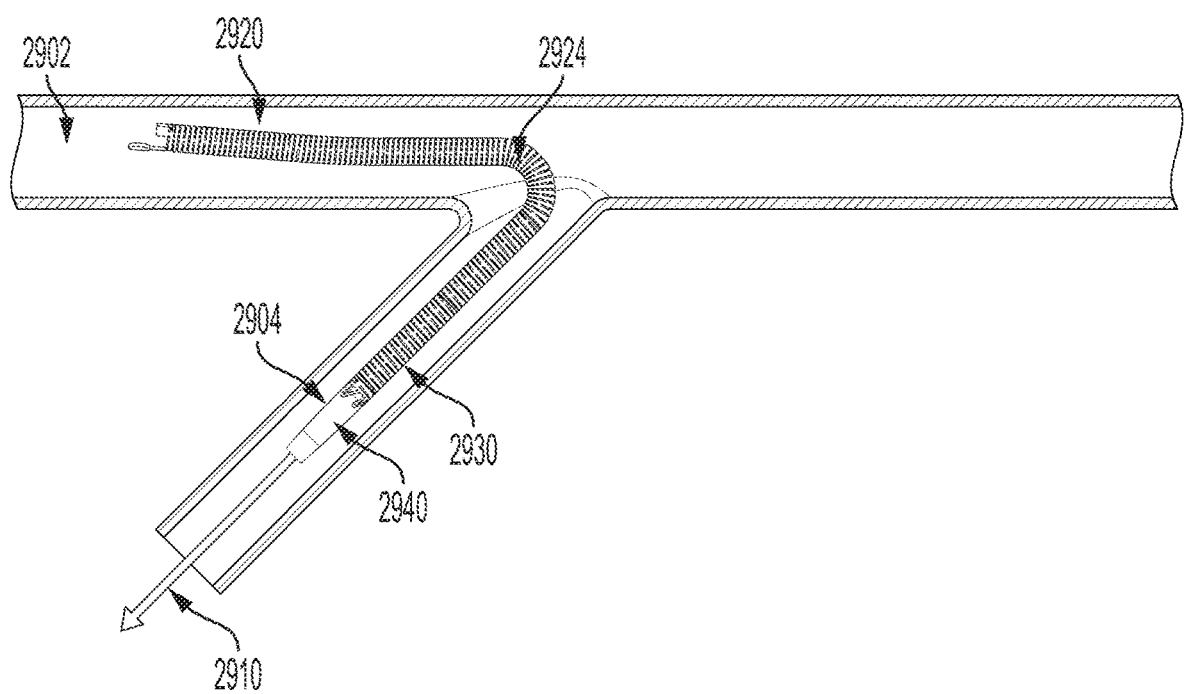
FIG. 29(d) shows the view of FIG. 29(c) after a guidewire has been inserted and the catheter has advanced through the side branch over the guidewire.

FIG. 29(d) shows the continued advancement of the distal tubular module 2920 through a first side branch 2904. A guidewire 2910 can be used to straighten the curvilinear section 2930 to enable the catheter to proceed through the lumen of the side branch 2804. Because of the engineered flexibility of the distal tubular module, the distal tubular modules can bend to accommodate sharp turning angles 2924.

In short, in both single side branch access methods, the preset, curvilinear section of the distal tubular module is used in the manner of a hook to create a secure anchor for advancement into side branches, ultimately allowing advancement of the catheter through multiple arterial vessel and side branches.

Figure 30A:
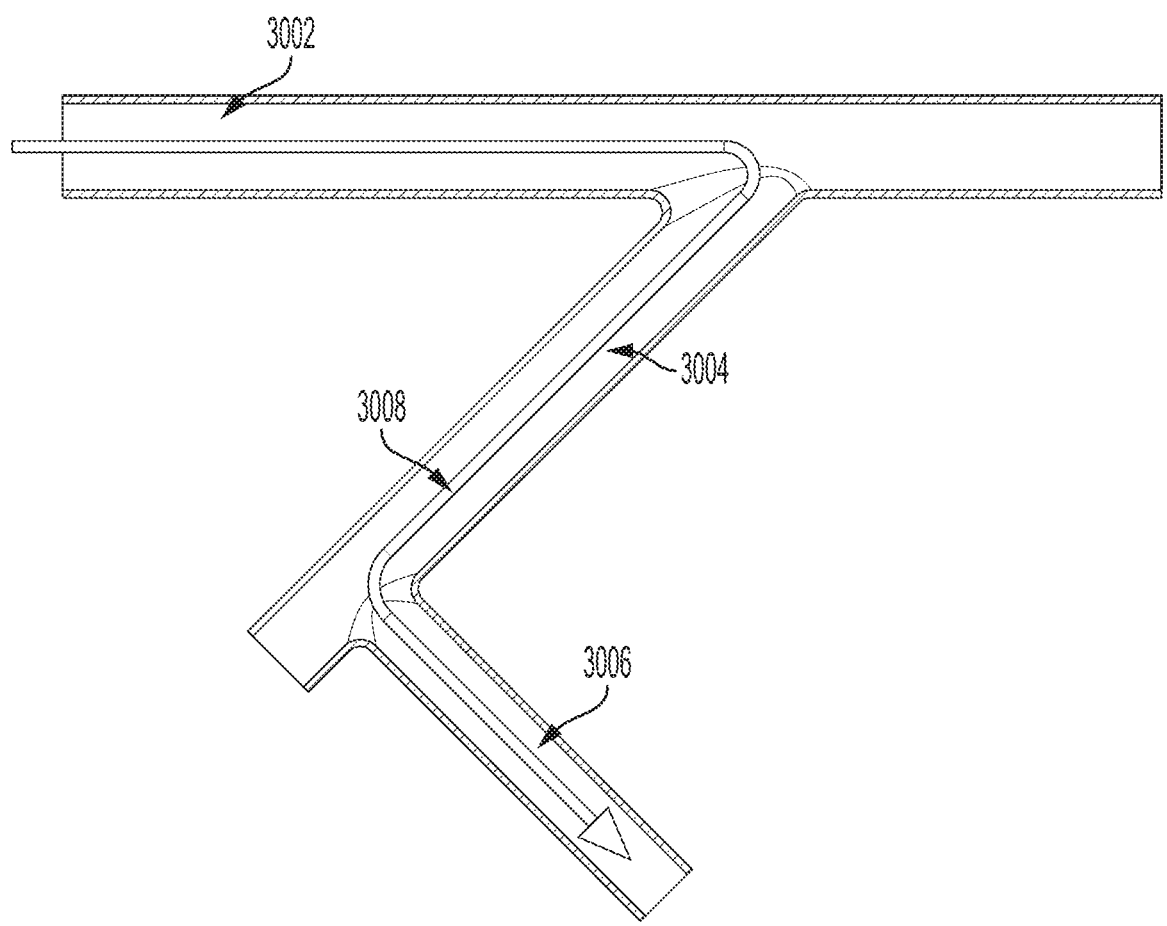
FIG. 30(a) shows a cross-section of an example section of an artery system having a main artery, a side-branch artery off of the main artery, and a second side branch off of the first side branch. A pathway for a catheter through the system is shown.
Figure 30B:
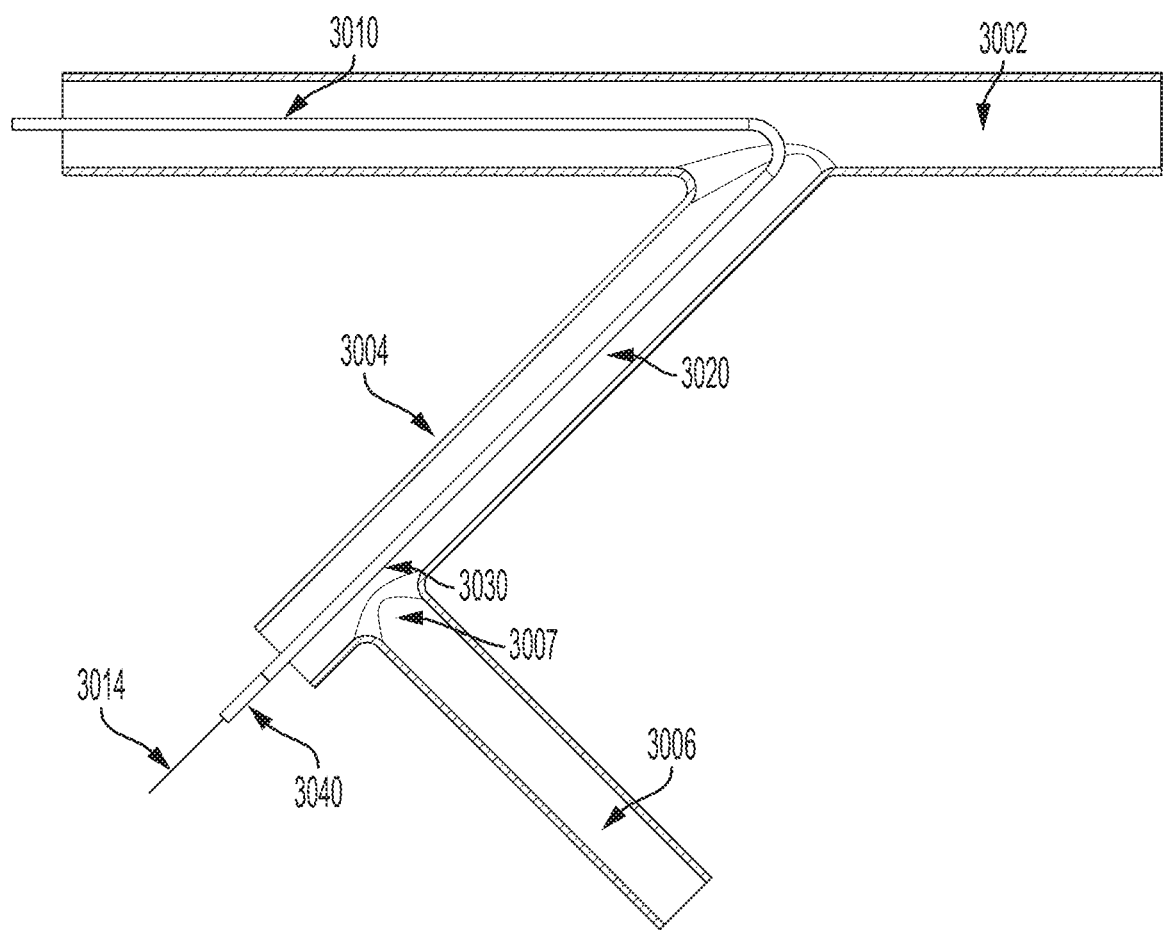
FIG. 30(b) shows a cross-section view of FIG. 30(a) shows the view of 30(a) in which a modular catheter according to the present invention has advanced through the first side branch past the opening of the second side branch.
Figure 30C:
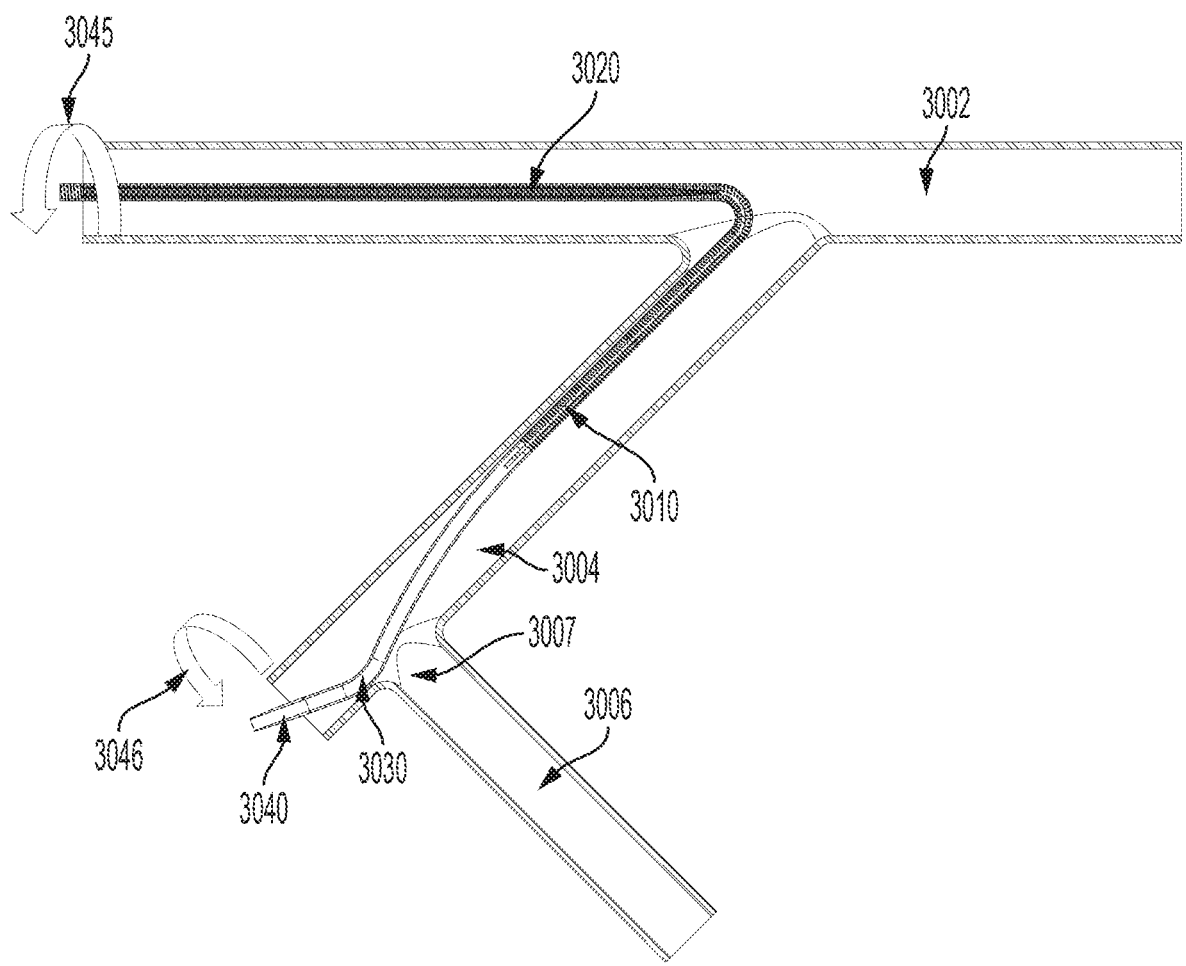
FIG. 30(c) shows a cross-section view of FIG. 30(b) after the guidewire has been withdrawn allowing the curvilinear section of the distal tubular module to bend.
Figure 30D:
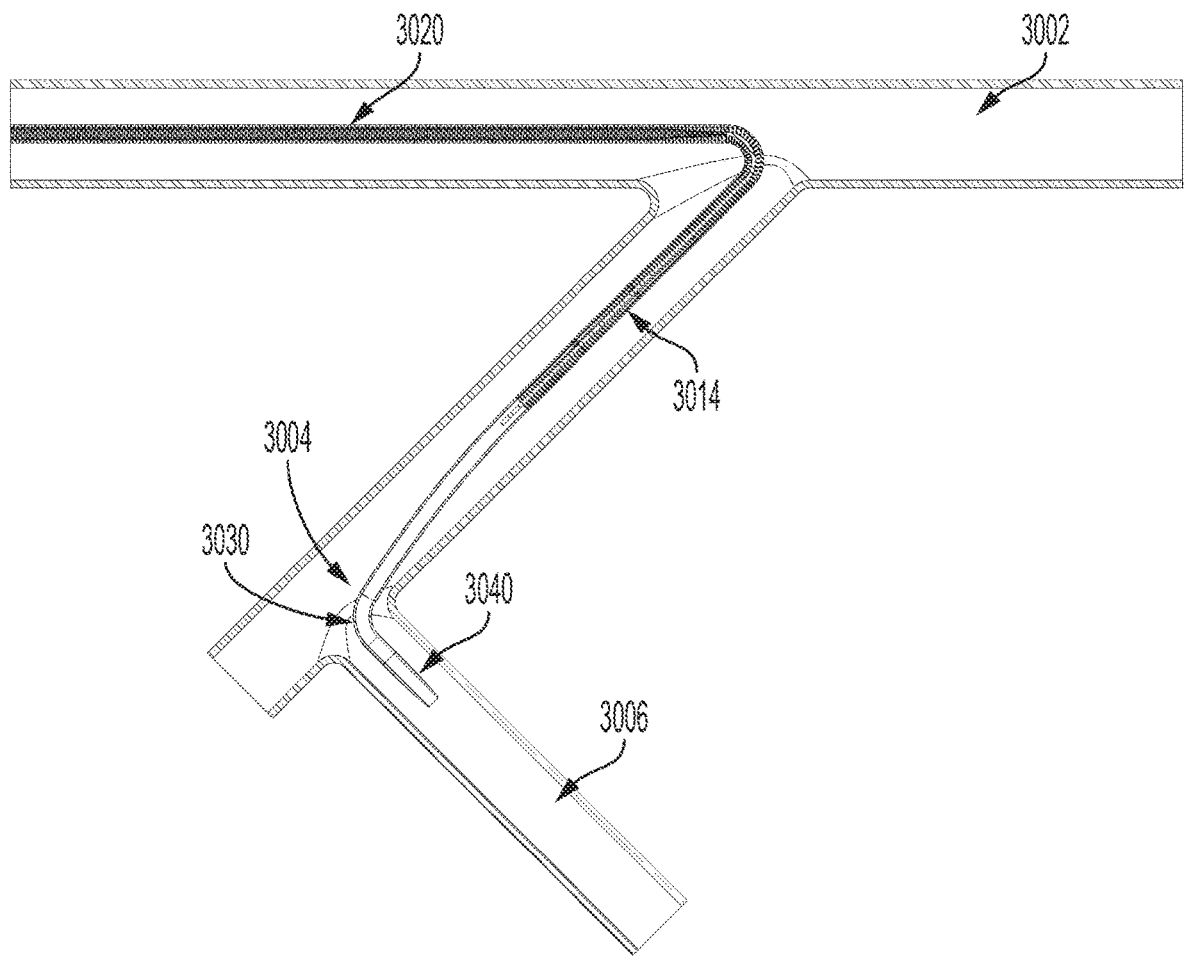
FIG. 30(d) shows a cross-section view of the entry of the tip and portion of the curvilinear section of the modular catheter in the second branch.

FIG. 30(a) shows an arterial system including a main artery 3002, a side branch artery 3004, and a secondary side branch 3006 coming off of the side branch 3004. A path 3008 for advancing a catheter through the main artery 3002 and the two side branches 3004, 3006 is shown. FIG. 30(b) shows a distal tubular module 3020 extended through a side branch 3004 in a manner discussed above with respect to FIGS. 28(a) to 28(e) and FIGS. 29(a) to 29(d). The tip 3040 and the tapered end of the guidewire 3014 extend at an approximately right angle to the axis of the second branch 3006. In FIG. 30(c), the guidewire 3010 has been partially withdrawn and a torquing force, 3045, 3046, has been applied to the distal tubular module 3020. Because of the construction of the catheter, the torque is transmitted to the tip 3040 and curvilinear portions 3030 (as shown by the curved arrows 3046). The torquing force angles the tip 3040 away from the axis of the first branch 3004. A combination of torquing force and lateral movement enable the tip 3040 to access second side branch 3006 as shown in FIG. 30(d).

Figure 30E:
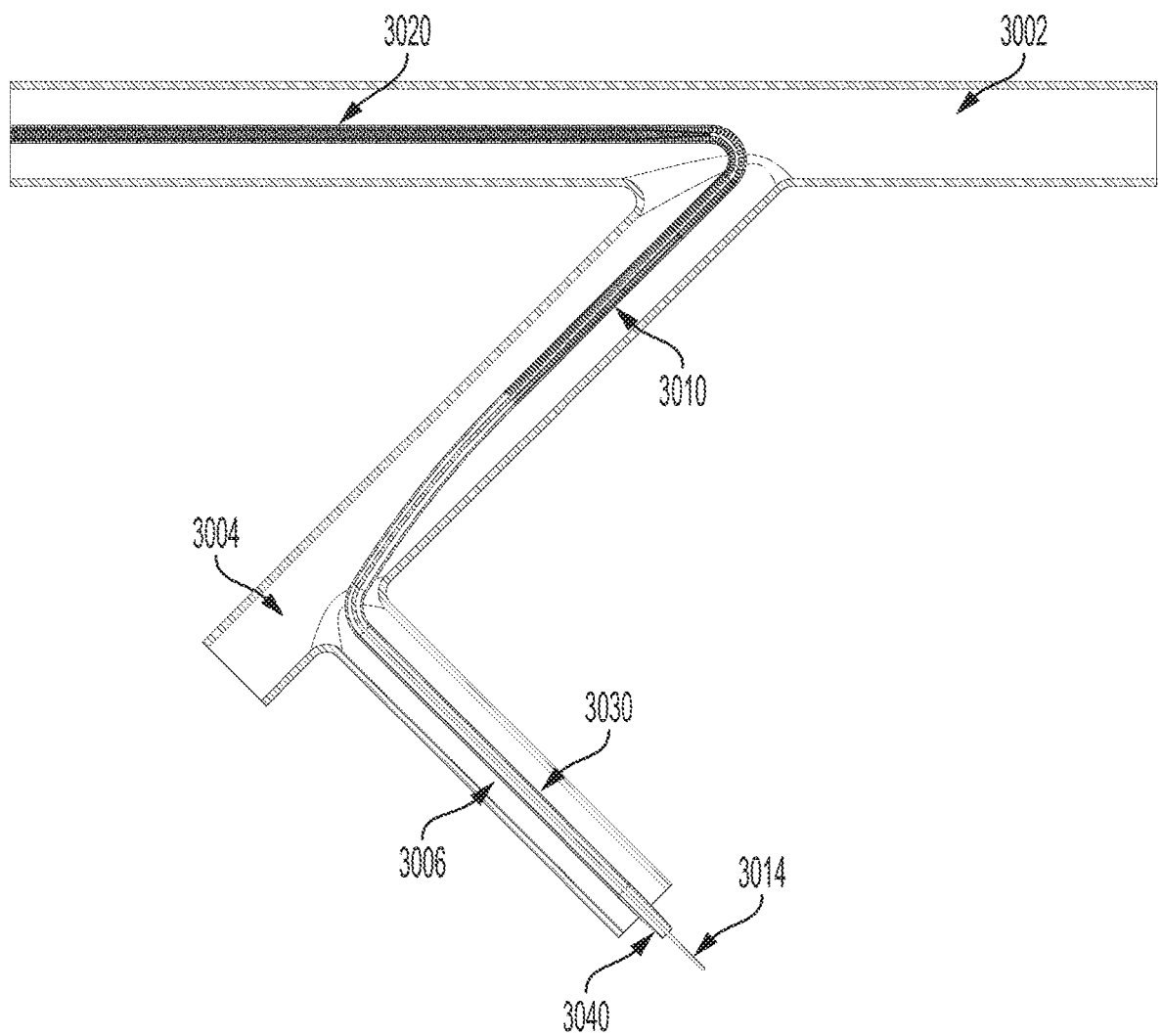
FIG. 30(e) shows the catheter advanced over a guidewire through the second branch.

In FIG. 30(e), the guidewire 3010 is advanced through the distal tubular module 3020 and tip 3040, allowing the distal tubular module 3020 to be transported over the path defined by the guidewire 3010.

Because of the modular construction of the catheter system according to the present invention, a family of microcatheters can be created by varying the distal tubular module of the catheter system for use in different procedures. A microcatheter is typically a single-lumen device that can be loaded on a guidewire in order to track it to the target lesion. The typical outer diameter (OD) ranges from about 1.30 mm on the proximal portion of the shaft to about 0.70 mm on the distal portion or tip of the shaft. The internal diameter of the lumen of the distal tubular module can vary and when used as a microcatheter can taper. The trackability and pushability of the distal tubular module can be varied as described above. The distal tubular module can be designed to address specific anatomical challenges, such as for use in antegrade procedures or retrograde procedures, for use in peripheral vascular access procedures, or for use as a re-entry catheter. The distal tubular module and the proximal tubular module can be preassembled with the proximal tubular module being attached to one of a variety of distal tubular modules. Or the distal tubular module and the proximal tubular module can be separate and assembled immediately prior to use.

The design of the distal tubular module can be varied such as by using different materials for fabrication. The in-line stacked variable wall thickness can also be varied, such as by simple inline stepped reduction in outer diameter while maintaining a constant inner diameter, by machining or grinding the tubular module material to vary the wall thickness along the length of the tubular module, or by laser cutting, ablating, machining, or grinding the tubular module material to create specific design features along the tubular module surface, such as a screw thread design carved out of the tubular module material at a specific location or along a defined length. The design of the distal tubular module 120 can also be varied through the use of stacked interrupted spiral-cut patterns along the length of the tubular module. These interrupted spiral-cut patterns formula variables could include the cut pitch angle, laser cut path width, or stacked variable cut patterns along the length of the tubular module, for example having a formula for interrupted spiral-cut pattern of cut and non-cut degrees along the helical cut.

Another specific example of a use for the modular catheter system would be for creating a microcatheter device. Such micro catheter could comprise a base micro catheter as one of the tubular modules. This base microcatheter could be used for an antegrade approach, having tight lesion access and backup wire support. The second tubular module can be one of a variety of microcatheters. These devices could have peripheral vascular and neuro vascular arterial access and can be used in many disease management applications and should not be limited to only the example provided herewith.

EXAMPLES

Testing Methodology:

The proximal tubular module and the distal tubular module can have different flexibility, kinkability, torque to failure, torqueability, trackability, pushability, crossability, and rotational response. A variety of different tests are available for testing flexibility, kinkability, torque to failure, torqueability, trackability, pushability, crossability, and rotational response. Various standard tests for these properties are known in the art.

The proximal tubular module and the distal tubular module can have the same flexibility or different flexibilities. Flexibility is the quality of bending without breaking. The flexibility of the tubular module is dependent on the material used, the interrupted spiral pattern, the wall thickness, the inner diameter and the outer diameter, and other variables. Flexibility can be determined by one of the following testing methods. One method of testing flexibility uses a proximal load cell to measure the ability of the device to advance and withdraw, with no loss of function or damage to the tortuous anatomy, over a specific bend angle. Alternatively, a roller system can be used to determine the smallest radius of curvature that the device can withstand without kinking. Additionally, tests can be performed by a cantilever beam to measure force and bending angle by calculating $F=[M\times(\% SR)]/(S\times100)$ with angularity at 50° where F=flexibility, M=total bending moment, % SR=scale reading average, and S=span length. Another method of testing flexibility is to use one- and four-point bending tests to evaluate flexibility under displacement control using a ZWICK 005 testing machine which detects the force F and the bending deflection f when one end of a device is grilled and the other end pressed with a plate moving at a constant speed. The highest measured data describes the flexibility as determined by the equation $E\times I=(F\times L^3)/(3\times f)$ ($Nmm^2$) where I=moment of inertia, E=Young modulus, L=bending length, f=bending deflection, and F=point force and E×I=flexibility.

The proximal tubular member and the distal tubular member can have the same or different torque to failure or torque to break. Torque to failure is the amount of twisting or rotational force the tubular member can withstand before a plastic deformation of the catheter components, a fracture or break occurs. One method for testing torque to failure is through the use of proximal and distal torque sensors which measure the amount of torque and the number of revolutions until device failure by rotating the device at a more proximal location and fixing the distal end while the device is routed through tortuous anatomy. Another testing method for calculating torque to failure is by testing torque strength immediately following submersion in 37±2° C. water for a set period of time. With a guidewire in place, the device can be inserted into a compatible guiding catheter which is constrained in a two dimensional shape to replicate access into the coronary anatomy until the distal most 10 cm of the catheter is exposed beyond the guiding tip and is attached to a torque gauge to prevent rotation. The remainder of the catheter body is rotated in 360° increments until distortion, failure, breaks, fractures, kinks, or other damage occurs along the catheter or at the catheter tip, or for a set number of rotations.

The proximal tubular member and the distal tubular member can have the same or different torqueability. Torqueability is the amount of torque, or rotation, lost from one end of the tubular module to the other end of the tubular module when a rotational force is exerted on one end. One method for testing torqueability is by using a proximal and distal torque sensor to measure the amount of torque transmitted through the device by rotating the device at a more proximal location and fixing the distal end while the device is routed through tortuous anatomy. Another method for testing torqueability is by using an artery simulating device for PTCA training, such as the PTCA trainer, T/N: T001821-2, designed by Shinsuke Nanto, M.D., which simulates a clinical tortuous path. An indicator attached to the catheter tip and inserted through the hole of a dial. The catheter body is connected to a rotator, for example T/N: T001923, and rotated clockwise in 90° increments to 1080°. The angle measured by dial attached to the indicator on the catheter tip is used to calculate the ratio of the angle of rotation of the body to the angle of rotation of the tip, which corresponds with the amount of torque lost during rotation.

The proximal tubular module and the distal tubular module can have the same trackability or different trackabilities. One method for testing trackability is to use a proximal load cell to measure the force to advance the device through a tortous anatomy with or without the aid of a guiding accessory.

The proximal tubular module and the distal tubular module can have the same or different pushability. One method for testing pushability is to use a proximal and distal load cell to measure the amount of force the distal tip of the device sees when a known force is being applied to on the proximal end.

The proximal tubular module and the distal tubular module can have the same or different crossability. One method for testing crossability is to use a proximal load cell to measure the ability of the catheter device to advance and withdraw over a specific lesion site without loss of function or damage to the tortuous anatomy. Additionally, a roller system can determine the worst lesion that the device can withstand without damage.

The proximal tubular module and the distal tubular module can have the same or different rotational response. One method for testing rotational response is by using proximal and distal rotation encoders to measure the amount of rotation transmitted through the device by rotating the device at a more proximal location and keeping the distal end free while the device is routed through tortuous anatomy.

The scope of the present invention is not limited by what has been specifically shown and described hereinabove. Those skilled in the art will recognize that there are suitable alternatives to the depicted examples of configurations, constructions, and dimensions, and materials. The citation and discussion of any references in the application is provided merely to clarify the description of the present invention and is not an admission that any reference is prior art to the invention described herein. All references cited and discussed in this specification are incorporated herein by reference in their entirety. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed:

1. A catheter comprising: a first tubular module and a second tubular module coupled to the first tubular module by a joint, the joint comprising: (a) at least one snap-fit connector on the first tubular module and a snap-fit acceptor positioned on the second tubular module, wherein the snap-fit connector and snap-fit acceptor are level with inner and outer surfaces of the first tubular module and the second tubular module when coupled together to define a continuous lumen with a uniform diameter therethrough, and wherein the snap-fit connector includes a cantilever joint; and (b) at least one stabilizing element including a tongue element positioned on the first tubular module and a groove element positioned on the second tubular module, wherein the stabilizing element does not include a cantilever joint, and wherein the stabilizing element prevents the first and second tubular modules from rotating circumferentially at the joint; and wherein the joint prevents the first and second tubular modules from pivoting with respect to each other.

2. The catheter of claim 1, wherein at least one section of the first or second tubular module comprises a plurality of interrupted spiral cuts.

3. The catheter of claim 1, wherein the second tubular module is formed from Nitinol.

4. The catheter of claim 3, wherein the first tubular module is formed from stainless steel of SAE grade selected from 304, 316, 402, and 440, 17-7 precipitation hardened stainless steel (PH), or Nickel Cobalt Alloy (MP35N).

5. The catheter of claim 1, wherein at least a portion of the joint is enclosed with a tubular cover.

6. The catheter of claim 1, further comprising at least two cut openings, a first and a second cut opening, wherein the cut openings are positioned on at least one of the first or second tubular modules.

7. The catheter of claim 6, wherein a filament is treaded in a spiral configuration around the first or second tubular modules and wherein one end of the filament is positioned in the first cut opening and an other end of the filament is positioned in the second cut opening.

8. The catheter of claim 7, wherein the filament is threaded in a clockwise spiral configuration.

9. The catheter of claim 8, wherein the filament is fixed on the first or second tubular modules by at least one ring.

10. The catheter of claim 7, wherein the filament is threaded in a counterclockwise spiral configuration.

11. The catheter of claim 1, comprising 2-20 tubular modules.

12. The catheter of claim 11, wherein at least a portion of one or more of the at least one tubular module is covered with a polymer forming a jacket.

13. The catheter of claim 12 wherein the polymer jacket is formed from nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone).

14. The catheter of claim 1, wherein at least a portion of the inner lumen is coated with a lining.

15. The catheter of claim 14, wherein the lining is formed from nylon, polyether block amide, PTFE (polytetrafluoroethylene), FEP (fluorinated ethylene propylene), PFA (perfluoroalkoxy alkane), PET (polyethylene terephthalate) or PEEK (polyether ether ketone).

16. The catheter of claim 11, wherein the first tubular module is formed from stainless steel and the second tubular module is formed from Nitinol.

17. The catheter of claim 11, wherein at least one edge of the snap-fit connector and snap-fit acceptor are beveled at an angle ranging from about 5° to about 90°.

18. The catheter of claim 1, wherein the at least one snap-fit connector extends from the first tubular module and has a same wall thickness as the first tubular module.

19. The catheter of claim 1, wherein the stabilizing element is level with inner and outer surfaces of the first tubular module and the second tubular module when coupled together.

20. The catheter of claim 19, wherein the tongue element has a rectangular shape.

21. A catheter comprising: a first tubular module and a second tubular module coupled by a joint, the joint comprising: (a) at least one snap-fit connector on the first tubular module and a snap-fit acceptor positioned on the second tubular module wherein the snap-fit connector and snap-fit acceptor are level with inner and outer surfaces of the first tubular module and the second tubular module when coupled together to define a continuous lumen with a uniform diameter therethrough, and wherein the snap-fit connector includes a cantilever joint; and (b) at least one stabilizing element including a tongue element positioned on the first tubular module and a groove element positioned on the second tubular module, wherein the stabilizing element does not include a cantilever joint; wherein the stabilizing element prevents the first and second tubular modules from rotating circumferentially at the joint; wherein the joint prevents the first and second tubular modules from pivoting with respect to each other; and wherein the first tubular module is formed from nitinol and the second tubular module is formed from stainless steel.

22. The catheter of claim 21, wherein at least one edge of the snap-fit connector and snap-fit acceptor are beveled at an angle ranging from about 5° to about 90°.

23. The catheter of claim 21, wherein the diameter of the continuous lumen is maintained around a central luminal axis when the first or second tubular module form a curvilinear shape.

24. A catheter comprising: a first tubular module and a second tubular module coupled to the first tubular module by a joint, the joint comprising:(a) at least one snap-fit connector on the first tubular module and a snap-fit acceptor positioned on the second tubular module, wherein the snap-fit connector and snap-fit acceptor are level with inner and outer surfaces of the first tubular module and the second tubular module when coupled together to define a continuous lumen with a uniform diameter therethrough, and wherein the snap-fit connector includes a cantilever joint; and (b) at least one stabilizing element including a tongue element positioned on the first tubular module and a groove element positioned on the second tubular module, wherein the tongue element has a rectangular shape, wherein the stabilizing element does not include a cantilever joint, and wherein the stabilizing element prevents the first and second tubular modules from rotating circumferentially at the joint; and wherein the joint prevents the first and second tubular modules from pivoting with respect to each other.

25. The catheter of claim 24, wherein the stabilizing element is level with inner and outer surfaces of the first tubular module and the second tubular module when coupled together.

* * * * *